(12) United States Patent
Shepherd et al.

(10) Patent No.: US 8,148,387 B2
(45) Date of Patent: Apr. 3, 2012

(54) AKT AND P70 S6 KINASE INHIBITORS

(75) Inventors: Timothy Alan Shepherd, Indianapolis, IN (US); Robert Dean Dally, Carmel, IN (US); Sajan Joseph, Bangalore (IN)

(73) Assignee: Eli Lilly and Company, Indianapolis, IN (US)

( * ) Notice: Subject to any disclaimer, the term of this patent is extended or adjusted under 35 U.S.C. 154(b) by 199 days.

(21) Appl. No.: 12/611,139

(22) Filed: Nov. 3, 2009

(65) Prior Publication Data

US 2010/0120801 A1    May 13, 2010

Related U.S. Application Data

(60) Provisional application No. 61/113,273, filed on Nov. 11, 2008.

(51) Int. Cl.
| | | |
|---|---|---|
| *A01N 43/90* | (2006.01) | |
| *A61K 31/519* | (2006.01) | |
| *C07D 487/00* | (2006.01) | |

(52) U.S. Cl. ..................... 514/262.1; 544/262
(58) Field of Classification Search .................. None
See application file for complete search history.

(56) References Cited

FOREIGN PATENT DOCUMENTS

| WO | WO 2005/117909 | 12/2005 |
|---|---|---|
| WO | WO 2006/046024 | 5/2006 |
| WO | WO 2006/071819 | 7/2006 |
| WO | WO 2007/003960 | 1/2007 |
| WO | WO 2007/125310 | 11/2007 |
| WO | WO 2007/125321 | 11/2007 |
| WO | WO 2008/012635 | 1/2008 |
| WO | WO 2008/075109 | 6/2008 |
| WO | WO 2008/140947 | 11/2008 |

*Primary Examiner* — Jeffrey Murray
(74) *Attorney, Agent, or Firm* — Tina M. Tucker; Danica Hostettler

(57) ABSTRACT

The present invention provides AKT and p70 S6 kinase inhibitors of the formula:

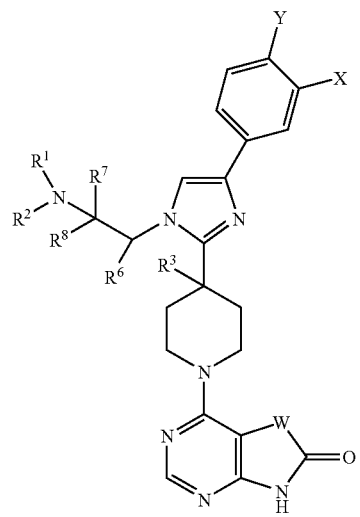

Formula I

The present invention also provides pharmaceutical compositions comprising compounds of Formula I, uses of compounds of Formula I and methods of using compounds of Formula I.

17 Claims, No Drawings

AKT AND P70 S6 KINASE INHIBITORS

This application claims the priority of U.S. Provisional Application No. 61/113,273 filed 11 Nov. 2008.

BACKGROUND OF THE INVENTION

The phosphotidylinositol-3-kinase (PI3K)/AKT/mammalian target of rapamycin (mTOR) pathway encompasses a number of signaling points which are critical in the control of cell growth and survival. AKT, also known as protein kinase B, is a serine-threonine protein kinase which has a key role in this pathway. Activation of AKT is mediated by PI3K. PI3K generates phospholipids which bind to AKT. Upon binding, AKT is recruited to the plasma membrane and is activated through phosphorylation. AKT activation and signaling promotes cell survival, growth and proliferation. Increased AKT activation has been implicated in a wide variety of cancers. P70 S6 kinase is a serine-threonine protein kinase which is a downstream effector of the PI3K/AKT/mTOR signaling pathway. P70 S6 kinase phosphorylates the ribosomal protein S6 in cells and regulates ribosome biogenesis, cell growth and cell cycle progression in response to mitogenic stimulation. P70 S6 kinase is commonly activated in many solid tumors.

A series of substituted piperidine compounds having AKT inhibitory activity are disclosed in WO 2008/075109. These compounds are disclosed for use in the treatment of diseases or conditions comprising or arising from abnormal cell growth or abnormally arrested cell death, including cancer. There remains a need to provide alternative AKT inhibitors which can be used in the treatment of proliferative disorders such as cancer. The present invention provides alternative AKT inhibitors. Preferred compounds of the present invention are more potent AKT inhibitors than those known in the art.

Additionally, there is a need to provide alternative p70 S6 kinase inhibitors which can be used in the treatment of proliferative disorders such as cancer. The present invention provides alternative p70 S6 kinase inhibitors. Preferred compounds of the present invention are more potent p70 S6 kinase inhibitors than those known in the art.

Preferred compounds of the present invention are inhibitors of both AKT and p70 S6 kinase. More preferred compounds of the present invention are more potent AKT inhibitors than known AKT inhibitors and more potent p70 S6 kinase inhibitors than known p70 S6 kinase inhibitors.

Certain compounds of the present invention have lower hERG activity than AKT and/or p70 S6 kinase inhibitors known in the art.

BRIEF SUMMARY OF THE INVENTION

The present invention provides compounds of the formula:

Formula I

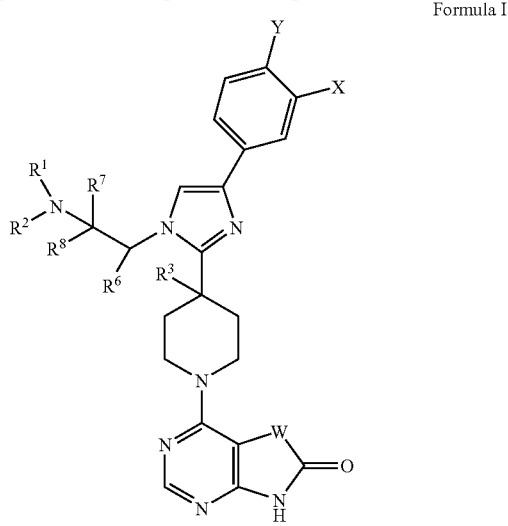

wherein:
X is F, Cl, $CF_3$, CN or H;
Y is F, H or Cl;
$R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position, or an azetidine ring substituted with hydroxy at the 3-position;
$R^3$ is H or OH;
$R^6$ is H; or $R^6$ and $R^2$ together with the nitrogen atom to which $R^2$ is attached form a piperidine ring;
$R^7$ and $R^8$ are independently H or $CH_3$; or $R^7$ and $R^1$ together with the nitrogen atom to which $R^1$ is attached form a pyrrolidine ring;
W is $CR^4R^5$, $NR^{10}$, C=O or C=CH—$R^9$;
$R^4$ and $R^5$ are independently H, $CH_3$, or $CH_2CH_3$; $R^4$ and $R^5$ together with the carbon atom to which they are attached form a cyclopentane ring; or one of $R^4$ or $R^5$ is benzyl and the other is H;
$R^9$ is 2-thiazolyl, 4-pyridyl, 2-methyl-4-thiazolyl, 2-imidazolyl, 5-thiazolyl, or 4-imidazolyl; and
$R^{10}$ is H or $C_1$-$C_3$ alkyl; or a pharmaceutically acceptable salt thereof.

The present invention provides a pharmaceutical formulation comprising a compound of the present invention, or a pharmaceutically acceptable salt thereof, and a pharmaceutically acceptable carrier, diluent, or excipient.

The present invention provides a compound of the present invention, or a pharmaceutically acceptable salt thereof, for use in therapy.

The present invention provides a compound of the present invention, or a pharmaceutically acceptable salt thereof, for use in treatment of glioblastoma multiforme. This invention further provides a method of treating glioblastoma multiforme in a mammal comprising administering to a mammal in need of such treatment an effective amount of a compound of the present invention, or a pharmaceutically acceptable salt thereof. Additionally, this invention provides the use of a compound of the present invention, or a pharmaceutically acceptable salt thereof, for the manufacture of a medicament for the treatment of glioblastoma multiforme. Furthermore, this invention provides a pharmaceutical composition for use in therapy comprising a compound of the present invention, or a pharmaceutically acceptable salt thereof, and provides a pharmaceutical composition for treating glioblastoma multiforme comprising a compound of the present invention, or a pharmaceutically acceptable salt thereof.

DETAILED DESCRIPTION OF THE INVENTION

The general chemical terms used in the formulae above have their usual meanings. For example, the term "$C_1$-$C_4$ alkyl" refers to a straight or branched, monovalent, saturated aliphatic chain of one to four carbon atoms and includes, but is not limited to, methyl, ethyl, propyl, isopropyl, butyl, isobutyl, and t-butyl. Likewise, the term "$C_1$-$C_3$ alkyl" includes methyl, ethyl, and isopropyl. Methyl and ethyl are preferred alkyl groups.

Compounds of this invention are bases, and accordingly react with any of a number of organic and inorganic acids to form pharmaceutically acceptable salts and the present invention includes the pharmaceutically acceptable salts of the compounds of Formula I. The term "pharmaceutically acceptable salt" as used herein, refers to salts of the compounds of Formula I that are substantially non-toxic to living organisms. Such salts include the pharmaceutically acceptable salts listed in Journal of Pharmaceutical Science, 66, 2-19 (1977), which are known to the skilled artisan. The free base and the hydrochloride, tosylate, hemisuccinate and tris-trifluoromethanesulfonic acid salts are preferred. The free base is especially preferred.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention. The specific stereoisomers and enantiomers of compounds of Formula I can be prepared by one of ordinary skill in the art utilizing well known techniques and processes, such as those disclosed by J. Jacques, et al., "Enantiomers, Racemates, and Resolutions", John Wiley and Sons, Inc., 1981, and E. L. Eliel and S. H. Wilen, "Stereochemistry of Organic Compounds", (Wiley-Interscience 1994), and European Patent Application No. EP-A-838448, published Apr. 29, 1998. Examples of resolutions include recrystallization techniques or chiral chromatography.

The skilled artisan will also appreciate that compounds of Formula I exist as tautomers, for example:

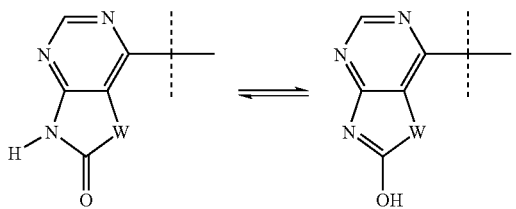

Although tautomers are structurally distinct, the skilled artisan will appreciate that they exist in equilibrium and are easily and rapidly interconvertible under ordinary conditions. (See, March, *Advanced Organic Chemistry*, Third Edition, Wiley Interscience, New York, N.Y. (1985), pages 66-70; and Allinger, *Organic Chemistry*, Second Edition, Worth Publishers, New York, N.Y., (1976), page 173). As such, the representation of a compound of Formula I in a single tautomeric form contemplates both tautomeric forms individually and mixtures thereof.

The compounds disclosed herein were named using the naming program within Chem Draw Ultra version v10 or Chem Bio Viz Ultra version v11.

In an alternative embodiment, there is provided a compound of the formula:

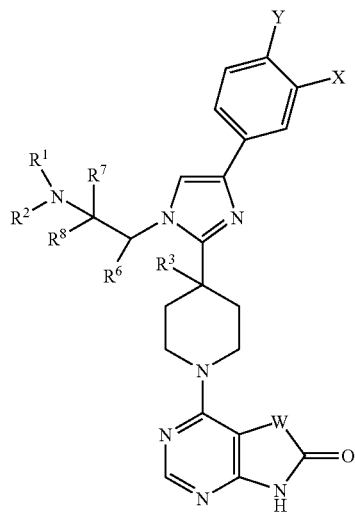

wherein:
X is F, Cl, $CF_3$, CN, H or $CHF_2$;
Y is F, H or Cl;
$R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position, or an azetidine ring substituted with hydroxy at the 3-position;
$R^3$ is H or OH;
$R^6$ is H; or $R^6$ and $R^2$ together with the nitrogen atom to which $R^2$ is attached form a piperidine ring;
$R^7$ and $R^8$ are independently H or $CH_3$; or $R^7$ and $R^1$ together with the nitrogen atom to which $R^1$ is attached form a pyrrolidine ring or a piperidine ring;
W is $CR^4R^5$, $NR^{10}$, C=O or C=CH—$R^9$;
$R^4$ and $R^5$ are independently H, $CH_3$, or $CH_2CH_3$; $R^4$ and $R^5$ together with the carbon atom to which they are attached form a cyclopentane ring; or one of $R^4$ or $R^5$ is benzyl and the other is H;
$R^9$ is 2-thiazolyl, 4-pyridyl, 2-methyl-4-thiazolyl, 2-imidazolyl, 5-thiazolyl, or 4-imidazolyl; and
$R^{10}$ is H or $C_1$-$C_3$ alkyl; or a pharmaceutically acceptable salt thereof.

In one embodiment, the present invention comprises compounds of Formula I wherein Y is F.

In another embodiment, the present invention comprises compounds of Formula I wherein X is Cl, $CF_3$ or F. In particular, X is $CF_3$.

In another embodiment, the present invention comprises compounds of Formula I wherein W is $CR^4R^5$, $NR^{10}$ or C=CH—$R^9$.

In another embodiment, the present invention comprises compounds of Formula I wherein W is $CR^4R^5$. In particular, $R^4$ and $R^5$ are independently H or $CH_3$; or $R^4$ is H and $R^5$ is $CH_2CH_3$; or $R^4$ and $R^5$ together with the carbon atom to which they are attached form a cyclopentane ring. More particularly, $R^4$ and $R^5$ are independently H or $CH_3$; or $R^4$ and $R^5$ together with the carbon atom to which they are attached form a cyclopentane ring. More particularly, $R^4$ and $R^5$ are independently H or $CH_3$. Even more particularly, $R^4$ and $R^5$ are both H.

In another embodiment, the present invention comprises compounds of Formula I wherein W is $NR^{10}$. In particular, $R^{10}$ is methyl or ethyl.

In another embodiment, the present invention comprises compounds of Formula I wherein W is C=CH—$R^9$. In particular, $R^9$ is 5-thiazolyl.

In another embodiment, the present invention comprises compounds of Formula I wherein $R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position. In particular, $R^1$ and $R^2$ are independently H or $CH_3$; or $R^1$ and $R^2$ together with the nitrogen atom to which they are attached form a pyrrolidine ring. More particularly, $R^1$ and $R^2$ are both $CH_3$.

In another embodiment, the present invention comprises compounds of Formula I wherein $R^3$ is H.

In another embodiment, the present invention comprises compounds of Formula I wherein $R^6$ is H.

In another embodiment, the present invention comprises compounds of Formula I wherein $R^7$ is H; or $R^7$ and $R^1$ together with the nitrogen atom to which $R^1$ is attached form a pyrrolidine ring. In particular, $R^7$ is H.

In yet another embodiment, the present invention comprises compounds of Formula I wherein $R^8$ is H.

In a further embodiment, the present invention comprises compounds of Formula I wherein Y is F and X is Cl, $CF_3$ or F. In particular, Y is F; X is Cl, $CF_3$ or F; and W is $CR^4R^5$. More particularly, Y is F; X is Cl, $CF_3$ or F; W is $CR^4R^5$; and $R^4$ and $R^5$ are independently H or $CH_3$, or $R^4$ and $R^5$ together with the carbon atom to which they are attached form a cyclopentane ring. Even more particularly, Y is F; X is Cl, $CF_3$ or F; W is $CR^4R^5$; $R^4$ and $R^5$ are independently H or $CH_3$, or $R^4$ and $R^5$ together with the carbon atom to which they are attached form a cyclopentane ring; and $R^1$ and $R^2$ are independently H, $C_1$-$C_4$ alkyl or $CH_2CH_2OH$, or $R^1$ and $R^2$ together with the nitrogen atom to which they are attached form a pyrrolidine ring optionally substituted with hydroxymethyl at the 2-position or hydroxy at the 3-position.

In a further embodiment, the present invention comprises compounds of Formula I wherein Y is F; X is Cl, $CF_3$ or F; and W is $NR^{10}$. In particular, Y is F; X is Cl, $CF_3$ or F; W is $NR^{10}$; and $R^1$ and $R^2$ are independently H, $C_1$-$C_4$ alkyl or $CH_2CH_2OH$, or $R^1$ and $R^2$ together with the nitrogen atom to which they are attached form a pyrrolidine ring optionally substituted with hydroxymethyl at the 2-position or hydroxy at the 3-position.

In a further embodiment, the present invention comprises compounds of Formula I wherein Y is F; X is Cl, $CF_3$ or F; and W is C=CH—$R^9$. In particular, Y is F; X is Cl, $CF_3$ or F; W is C=CH—$R^9$; and $R^9$ is 5-thiazolyl. More particularly, Y is F; X is Cl, $CF_3$ or F; W is C=CH—$R^9$; $R^9$ is 5-thiazolyl; and $R^1$ and $R^2$ are independently H, $C_1$-$C_4$ alkyl or $CH_2CH_2OH$, or $R^1$ and $R^2$ together with the nitrogen atom to which they are attached form a pyrrolidine ring optionally substituted with hydroxymethyl at the 2-position or hydroxy at the 3-position.

In a yet further embodiment compounds of the invention include those of the formula:

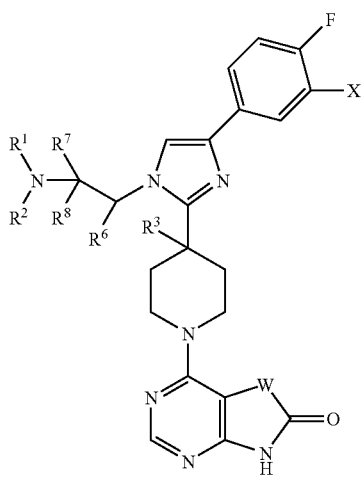

Formula II wherein:
X is F, Cl, or $CF_3$;
$R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position;
$R^3$ is H or OH;
$R^6$ is H; or $R^6$ and $R^2$ together with the nitrogen atom to which $R^2$ is attached form a piperidine ring;
$R^7$ and $R^8$ are independently H or $CH_3$; or $R^7$ and $R^1$ together with the nitrogen atom to which $R^1$ is attached form a pyrrolidine ring;

W is $CR^4R^5$, $NR^{10}$, or C=CH—$R^9$;
$R^4$ and $R^5$ are independently H or $CH_3$; or $R^4$ and $R^5$ together with the carbon atom to which they are attached form a cyclopentane ring;
$R^9$ is 5-thiazolyl; and
$R^{10}$ is H or $C_1$-$C_3$ alkyl; or a pharmaceutically acceptable salt thereof.

In one embodiment, the present invention comprises compounds of Formula II wherein X is $CF_3$.

In another embodiment, the present invention comprises compounds of Formula II wherein W is $CR^4R^5$ and $R^4$ and $R^5$ are independently H or $CH_3$. In particular, $R^4$ and $R^5$ are both H.

In another embodiment, the present invention comprises compounds of Formula II wherein W is $NR^{10}$ and $R^{10}$ is methyl or ethyl.

In another embodiment, the present invention comprises compounds of Formula II wherein $R^1$ and $R^2$ are independently H or $CH_3$; or $R^1$ and $R^2$ together with the nitrogen atom to which they are attached form a pyrrolidine ring. In particular, $R^1$ and $R^2$ are both $CH_3$.

In another embodiment, the present invention comprises compounds of Formula II wherein $R^3$ is H.

In another embodiment, the present invention comprises compounds of Formula II wherein $R^6$ is H.

In another embodiment, the present invention comprises compounds of Formula II wherein $R^7$ is H, or $R^7$ and $R^1$ together with the nitrogen atom to which $R^1$ is attached form a pyrrolidine ring. In particular, $R^7$ is H.

In another embodiment, the present invention comprises compounds of Formula II wherein $R^8$ is H.

The following compounds of the present invention, or pharmaceutically acceptable salts thereof, are preferred:

4-{4-[4-(4-Fluoro-3-trifluoromethyl-phenyl)-1-(2-methylamino-ethyl)-1H-imidazol-2-yl]-piperidin-1-yl}-5,7-dihydro-pyrrolo[2,3-d]pyrimidin-6-one;

4-{4-[1-(2-Amino-ethyl)-4-(4-fluoro-3-trifluoromethyl-phenyl)-1H-imidazol-2-yl]-piperidin-1-yl}-5,7-di-hydro-pyrrolo[2,3-d]pyrimidin-6-one;

4-{4-[4-(4-Fluoro-3-trifluoromethyl-phenyl)-1-((R)-1-methyl-piperidin-3-yl)-1H-imidazol-2-yl]-piperidin-1-yl}-5,7-dihydro-pyrrolo[2,3-d]pyrimidin-6-one;

4-{4-[1-(2-Dimethylamino-ethyl)-4-(4-fluoro-3-trifluoromethyl-phenyl)-1H-imidazol-2-yl]-piperidin-1-yl}-5,5-dimethyl-5,7-dihydro pyrrolo[2,3-d]pyrimidin-6-one;

4-{4-[4-(3,4-Difluoro-phenyl)-1-(2-pyrrolidin-1-yl-ethyl)-1H-imidazol-2-yl]-piperidin-1-yl}-5,7-dihydro-pyrrolo[2,3-d]pyrimidin-6-one;

4-{4-[4-(3-Chloro-4-fluoro-phenyl)-1-(2-pyrrolidin-1-yl-ethyl)-1H-imidazol-2-yl]-piperidin-1-yl}-5,7-dihydro-pyrrolo[2,3-d]pyrimidin-6-one;

4-{4-[1-(2-Dimethylamino-ethyl)-4-(4-fluoro-3-trifluoromethyl-phenyl)-1H-imidazol-2-yl]-piperidin-1-yl}-5H-pyrrolo[2,3-d]pyrimidin-6(7H)-one;

7-Ethyl-6-{4-[4-(4-fluoro-3-trifluoromethyl-phenyl)-1-(2-(pyrrolidin-1-yl)ethyl)-1H-imidazol-2-yl]-piperidin-1-yl}-7H-purin-8(9H)-one;

6-{4-[4-(3-Chloro-4-fluorophenyl)-1-(2-dimethylamino-ethyl)-1H-imidazol-2-yl]-piperidin-1-yl}-7-ethyl-7H-purin-8(9H)-one;

6-{4-[4-(3,4-Difluorophenyl)-1-(2-(pyrrolidin-1-yl)ethyl)-1H-imidazol-2-yl]-piperidin-1-yl}-7-ethyl-7H-purin-8(9H)-one;

6-{4-[4-(3-Chloro-4-fluorophenyl)-1-(2-dimethylamino-ethyl)-1H-imidazol-2-yl]-piperidin-1-yl}-7-isopropyl-7H-purin-8(9H)-one;

6-{4-[1-(2-Dimethylamino-ethyl)-4-(4-fluoro-3-trifluoromethyl-phenyl)-1H-imidazol-2-yl]-piperidin-1-yl}-7-ethyl-7H-purin-8(9H)-one;

6-{4-[4-(3,4-Difluoro-phenyl)-1-(2-dimethylamino-ethyl)-1H-imidazol-2-yl]-piperidin-1-yl}-7-ethyl-7,9-dihydro-purin-8-one;

4-{4-[4-(3,4-Difluoro-phenyl)-1-(2-dimethylamino-ethyl)-1H-imidazol-2-yl]-piperidin-1-yl}-5-ethyl-5,7-dihydro-pyrrolo[2,3-d]pyrimidin-6-one;

4-{4-[4-(3,4-Difluorophenyl)-1-(2-dimethylamino-ethyl)-1H-imidazol-2-yl]-piperidin-1-yl}-5-methyl-5H-pyrrolo[2,3-d]pyrimidin-6(7H)-one;

4-{4-[4-(3-Chloro-4-fluorophenyl)-1-(2-dimethylamino-ethyl)-1H-imidazol-2-yl]-piperidin-1-yl}-5,5-dimethyl-5H-pyrrolo[2,3-d]pyrimidin-6(7H)-one; and 4-{4-[4-(3-Chloro-4-fluorophenyl)-1-(2-(pyrrolidin-1-yl)ethyl)-1H-imidazol-2-yl]-piperidin-1-yl}-5-methyl-5H-pyrrolo[2,3-d]pyrimidin-6(7H)-one.

The compound 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, or a pharmaceutically acceptable salt thereof, is especially preferred.

In a preferred embodiment, the compound 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, or a pharmaceutically acceptable salt thereof, is crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate. Crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate is characterised by an X-ray powder diffraction pattern comprising at least one of the following peaks; 7.4, 14.9, 21.1, 19.8 or 10.5 (±0.1° 2θ). Preferably, characterized by an X-ray powder diffraction pattern comprising peaks at 7.4, 14.9, 21.1, 19.8 and 10.5 (±0.1° 2θ). Crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate may also be characterised by an SSNMR spectrum comprising at least one of the following resonances; 179.8, 156.9, 151.9, 137.5 or 33.8 ppm. Preferably, characterized by an SSNMR spectrum comprising resonances at 179.8, 156.9, 151.9, 137.5 and 33.8 ppm.

In another embodiment, the compound 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, or a pharmaceutically acceptable salt thereof, is 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid. 4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid is characterised by an X-ray powder diffraction pattern comprising at least one of the following peaks; 22.6, 21.7, 21.5, 21.1, 20.4, 20.2, 18.6, 18.5, 15.5, 15.0 and 13.2 (±0.1° 2θ). Preferably, characterized by an X-ray powder diffraction pattern comprising peaks at 22.6, 21.7, 21.5, 21.1, 20.4, 20.2, 18.6, 18.5, 15.5, 15.0 and 13.2 (±0.1° 2θ). 4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid may also be characterised by an SSNMR spectrum comprising at least one of the following resonances; 176.9, 155.4, 150.0, 148.0, 94.6, 57.7, 36.4, 32.0 and 27.4 ppm. Preferably, characterized by an SSNMR spectrum comprising resonances at 176.9, 155.4, 150.0, 148.0, 94.6, 57.7, 36.4, 32.0 and 27.4 ppm.

In another embodiment, the compound 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, or a pharmaceutically acceptable salt thereof, is 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate. 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate is characterised by an SSNMR spectrum comprising at least one of the following resonances; 164.9, 150.7, 138.3 and 61.6 ppm. Preferably, characterized by an SSNMR spectrum comprising resonances at 164.9, 150.7, 138.3 and 61.6 ppm.

In an alternative embodiment, there is provided a compound selected from:

5-Ethyl-4-{4-[4-(4-fluoro-3-(trifluoromethyl)phenyl)-1-((S)-piperidin-2-ylmethyl)-1H-imidazol-2-yl]-piperidin-1-yl}-5,7-dihydro-pyrrolo[2,3-d]pyrimidin-6-one tris hydrochloride;

4-{4-[4-(3-Difluoromethyl-4-fluorophenyl)-1-(((R)-1-methylpiperidin-2-yl)methyl)-1H-imidazol-2-yl]-piperidin-1-yl}-5-ethyl-5,7-dihydro-pyrrolo[2,3-d]pyrimidin-6-one; and (R)-6-{4-[4-(3-Difluoromethyl-4-fluorophenyl)-1-((1-methylpiperidin-2-yl)methyl)-1H-imidazol-2-yl]-piperidin-1-yl}-7-ethyl-7H-purin-8(9H)-one.

The compounds of the present invention are inhibitors of AKT and p70 S6 kinase and are therefore useful in the treatment of metabolic diseases and disorders such as obesity, diabetes, metabolic syndrome, insulin resistance, hyperglycemia, hyperaminoacidemia, and hyperlipidemia. The compounds of the present invention are also useful in the treatment of cancer, particularly glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma (Sodhi et al., Cancer Cell, 10: 133-143 (2006)), Hodgkin's lymphoma (Dutton et al., J. Pathol., 205: 498-506 (2005)), lymphangioleiomyomatosis (Goncharova et al., J. Biol. Chem., 277:34, 30958-30967 (2002)), Non-Hodgkin's lymphoma, sarcoma and neuroendocrine tumors, in particular neuroendocrine tumors of the pancreas or small intestine (Wong et al., 2009 Gastrointestinal Cancers Symposium, Abstract no. 174), in mammals Inhibitors of AKT and p70 S6 kinase are also useful inhibitors of angiogenesis in mammals. It is preferred that the mammal to be treated is a human.

The compounds of the present invention, or pharmaceutically acceptable salts thereof, can be used in a method of treating cancer, in particular, the cancers described above, in a mammal comprising administering to a mammal in need of such treatment an effective amount of a compound of the present invention, or a pharmaceutically acceptable salt thereof. The compounds of the present invention, or pharmaceutically acceptable salts thereof, can be used for the treatment of cancer, in particular, the cancers described above. Furthermore, the compounds of the present invention, or pharmaceutically acceptable salts thereof, can be used in the manufacture of a medicament for the treatment of cancer, in particular the cancers described above. There is also provided a pharmaceutical composition for treating cancer, in particular, the cancers described above, comprising a compound of the present invention, or a pharmaceutically acceptable salt thereof.

The compounds of the present invention, or pharmaceutically acceptable salts thereof, can be used in a method of inhibiting angiogenesis in a mammal comprising administering to a mammal in need of such treatment an effective amount of a compound of the present invention, or a pharmaceutically acceptable salt thereof. The compounds of the present invention, or pharmaceutically acceptable salts thereof, can be used in the inhibition of angiogenesis. Furthermore, the compounds of the present invention, or pharmaceutically acceptable salts thereof, can be used in the manufacture of a medicament for the inhibition of angiogenesis. There is also provided a pharmaceutical composition for inhibiting angiogenesis comprising a compound of the present invention, or a pharmaceutically acceptable salt thereof.

The compounds of the present invention may be used in combination with other therapeutic agents and in particular, mTOR (mammalian target of rapamycin) inhibitors, EGFR (epidermal growth factor receptor) inhibitors, gemcitabine (Gemzar®), cisplatin, tasisulam (sodium N-[(5-bromothiophen-2-yl)sulfonyl]-2,4-dichlorobenzamide), pemetrexed (Alimta®), docetaxel (Taxotere®), doxorubicin (Doxil®) or irinotecan (Campto®; Camptosar®). Preferred mTOR inhibitors include rapamycin (also known as sirolimus) and analogues thereof such as everolimus (42-O-(2-hydroxy)ethyl-rapamycin; disclosed in EP 1 413 581), temsirolimus (42-(3-hydroxy-2-(hydroxymethyl)-2-methyl propanoate)-rapamycin; Torisel®; disclosed in WO 95/28406) and deforolimus (42-(dimethylphosphinate)rapamycin; disclosed in WO 03/64383). Preferred EGFR inhibitors include erlotinib, cetuximab (Erbitux®; disclosed in EP 0 359 282), panitumumab (Vectibix®; disclosed in EP 0 359 282) and gefinitib (Iressa®; disclosed in EP 0 566 226).

In one embodiment, the present invention provides a product containing a compound of the present invention, or a pharmaceutically acceptable salt thereof, and a therapeutic agent selected from those listed above as a combined preparation for simultaneous, separate or sequential use in therapy. The present invention further provides a compound of the present invention, or a pharmaceutically acceptable salt thereof, for use in simultaneous, separate and sequential combination with a therapeutic agent selected from those listed above in the treatment of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma or sarcoma. The present invention further provides a method of treating a cancer selected from the group consisting of glioblastoma multiforme, adenocarcinomas of the colon, non-small-cell lung cancer, small-cell lung cancer, cisplatin-resistant small-cell lung cancer, ovarian cancer, leukemia, pancreatic cancer, prostate cancer, mammary carcinoma, renal cell carcimoma, multiple myeloma, Kaposi's Sarcoma, Hodgkin's lymphoma, lymphangioleiomyomatosis, Non-Hodgkin's lymphoma and sarcoma comprising administering to a patient in need thereof a compound of the present invention, or a pharmaceutically acceptable salt thereof, and a therapeutic agent selected from those listed above in amounts that in combination are effective.

In another embodiment, the present invention provides a pharmaceutical composition comprising a compound of the present invention together with a pharmaceutically acceptable carrier and optionally other therapeutic agents. In particular, a therapeutic agent selected from those listed above.

Oral administration of the compounds of the present invention is preferred. Intravenous administration of the compounds of the present invention is also preferred. Depending on the circumstances, other routes of administration may be used or even preferred. For example, transdermal administration may be very desirable for patients who are forgetful or petulant about taking oral medicine. Compounds of the present invention may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The compounds of Formula I can be prepared by one of ordinary skill in the art following art recognized techniques and procedures. More specifically, compounds of Formula I can be prepared as set forth in the schemes, preparations, and examples set forth below. It will be recognized by one of skill in the art that the individual steps in the following schemes may be varied to provide the compounds of Formula I. The reagents and starting materials are readily available to one of ordinary skill in the art. All substituents, unless otherwise specified, are as previously defined.

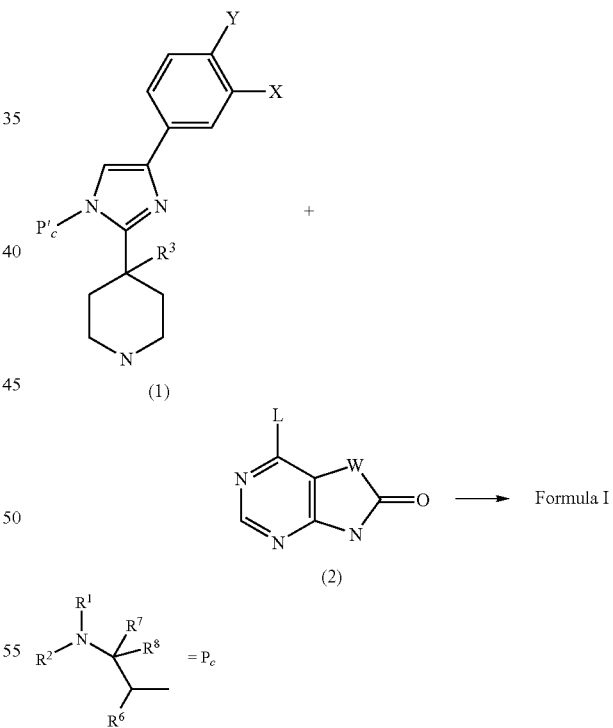

A substituted imidazole piperidine of formula (1), a substituted ketone of formula (2), and a base such as triethylamine (TEA), diisopropylethylamine (DIPEA) or 1,8-diazabicyclo[5.4.0]undec-7-ene (DBU) in a solvent, such as propanol, isopropyl alcohol (IPA), NN-dimethylformamide (DMF), methanol, N-methyl-pyrrolidene (NMP) or dimethyl sulfoxide (DMSO) are heated at an elevated temperature to form the compound of Formula I. L is a leaving group, e.g., chlorine. Alternatively, this reaction may be carried out by first combining potassium tert-butoxide, N,N'-bis(2,6-diisopropylphenyl)imidazol-2-ylidene-acetylacetonate palladium chloride [IPrPd(acac)Cl (*J. Org. Chem.* 2006, 71(10), 3816-3821)] and purging with nitrogen. Then adding anhydrous 1,2-dimethoxyethane (DME) and compounds (1) and (2) and heating to 80° C.

Compounds of Formula I wherein one of $R^4$ or $R^5$ is benzyl and the other is hydrogen may be prepared by reacting compound (1) with a compound of formula (2) which is substi- Note: in the instance of 4-(4-{4-(4-fluoro-3-trifluoromethyl-phenyl)-1-[2-(isopropyl-methyl-amino)-ethyl]-1H-imidazol-2-yl}-piperidin-1-yl)-7H-pyrrolo[2,3-d]pyrimidine-5,6-dione hydrochloride, oxidation of the 5 position methylene to the ketone can be observed under the reaction conditions.

Substituted imidazole piperidine compounds of formula (1) are prepared as illustrated in Scheme 2, where PG is a nitrogen protecting group, and all other substituents are as previously described.

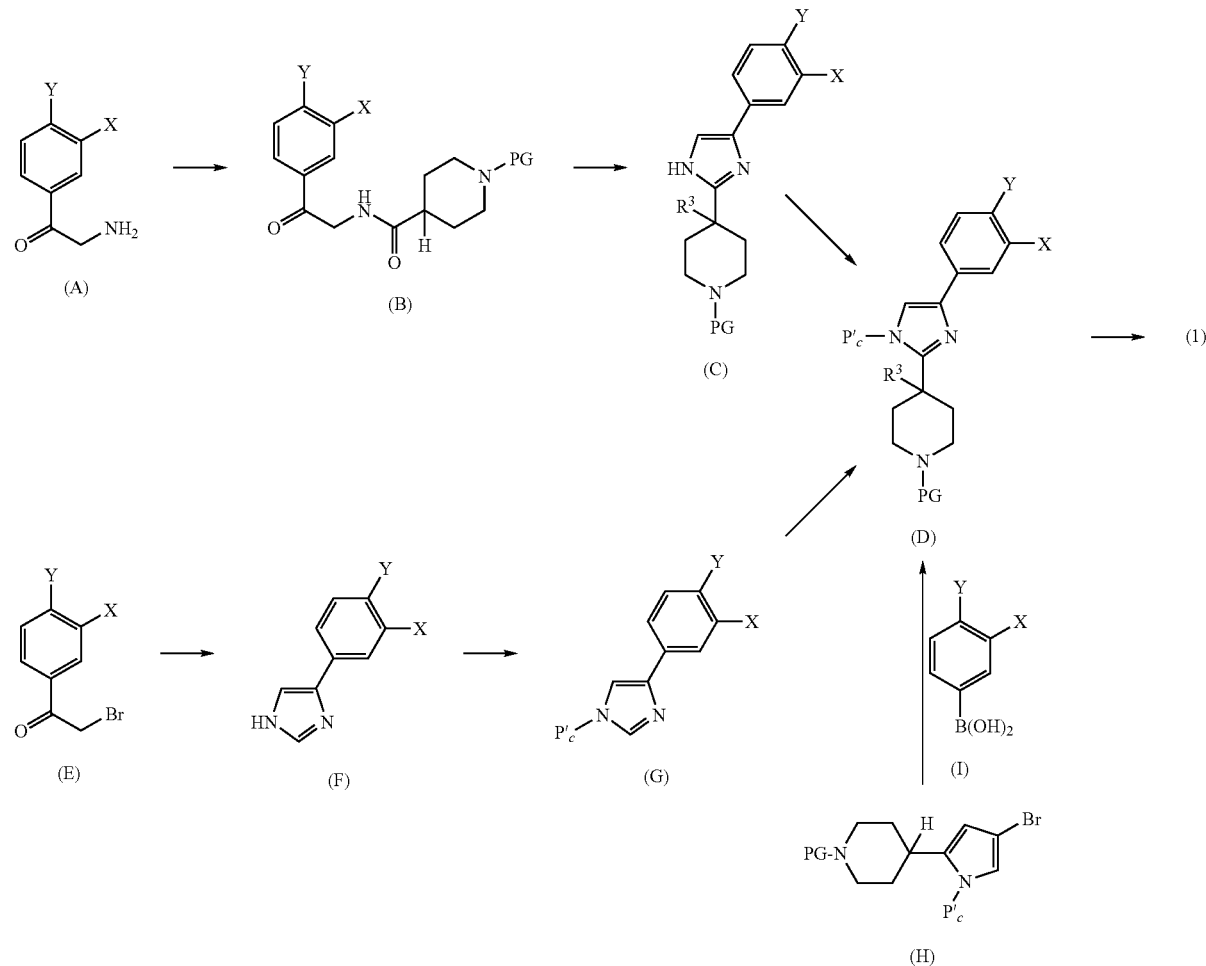

tuted with a benzylidene group and then subsequently reducing the benzylidene group to a benzyl group.

The $P'_c$ group may represent the desired final amine fragment with substitutents as defined previously ($P_c$), a precursor to $P_c$ or a protected $P_c$ fragment. All other substituents are defined previously. If the protecting group in $P'_c$ is carboxy benzyl group, deprotection to provide the desired amine may be done prior to or after reaction with compound (2). The carboxy benzyl protecting group may be removed by reaction with concentrated HCl. Alternatively, it may be removed in the presence of lithium aluminium hydride in tetrahydrofuran (THF) to provide a methyl substituted amine substituent as defined in $P_c$.

The compound of formula (A) can be prepared from the corresponding 2-bromo-phenyl ethanone compound. In the synthesis of compounds of Formula I in which $R^6$ and $R^2$ form a piperidine ring, the protected piperidine ring is present as an amine substituent in compound (A) prior to reaction to form compound (B). The amine substituted compound is synthesized by reaction of 3-amino-piperidine-1-carboxylic acid with a compound of formula (E) in the presence of a base such as TEA in a solvent such as DMF. Later in the synthesis the protecting group on the piperidin-3-yl may be removed and replaced with a methyl substituent.

Where $R^3$=H an amine of formula (A) is reacted with a nitrogen protected piperidine carboxylic acid in the presence of a coupling agent, such as, isobutyl chloroformate, 1-ethyl-3-[3-dimethylaminopropyl]-carbodiimide hydrochloride (EDC), 1-propanephosphonic acid cyclic anhydride (PPA) or thionyl chloride and an base such as N-methylmorpholine (NMM), DIPEA or TEA, in a solvent such as THF, dichloromethane (DCM), or DMF at reduced temperatures to form amide of formula (B). The imidazole piperidine of formula (C) is formed when a compound of formula (B), ammonium acetate or ammonium chloride, and a base such as TEA in a sealed vessel is exposed to microwave heat under pressure. An intermediate of compound (C) where the phenyl is unsubstituted can be prepared by condensing 2-oxo-2-phenylacetaldehyde with 4-formyl-piperidine-1-carboxylic acid tert-butyl ester in liquid ammonia overnight.

The compound of formula (C) is then alkylated to provide a compound of formula (D) where $R^3$ is hydrogen. More specifically, the compound of formula (C) is de-protonated with a base, such as, KOH or sodium hydride in a solvent such as DMSO, followed by addition of $P'_c$ with a leaving group such as halogen and in particular, chlorine. Most of the alkylating agents are commercially available or synthesized by methods known in the art. For example, the alkylating agent can be prepared from the corresponding alcohol in the presence of thionyl chloride in aqueous hydrochloric acid or phosphorus tribromide in benzene.

The amine of the alkylating agent may be further substituted by a benzyl group. The benzyl group may be subsequently replaced by a carboxy benzyl protecting group by reaction with benzylchloroformate, this can be carried out in one or two steps. The alkylating agent may, alternatively, contain a nitrile group which is reduced to form an amine The resulting amine may then be protected by a carboxy benzyl group.

The compound of formula (C) may be reacted with 2-(2-bromoethoxy)tetrahydrobo-2H-pyran or (2-bromoethoxy)-tert-butyl-dimethyl silane to form a compound of formula (D) in which $P'_c$ is a 2-(tetrahydro-pyran-2-yloxy)ethyl group or a 2-(tert-butyl-dimethyl-silanyloxy)-ethyl group, respectively. These groups are converted to a 2-hydroxy-ethyl substituent and then to a 2-methanesulfonoxy-ethyl substituent. The methansulfonyloxy(mesyl) leaving group can then be replaced by the desired amine.

Where the desired $P_c$ group is pyrrolidin-2-ylmethyl, the carboxy benzyl protected pyrrolidin-2-yl methyl is added to the compound of formula (C) by reaction with 2-(toluene-4-sulfonyloxymethyl)-pyrrolidene-1-carboxylic acid benzyl ester.

Alternately, a 4-bromo-imidazole of formula (H) undergoes coupling with a phenylboronate compound (I) in the presence of palladium (0) catalyst to form the compound of Formula (D) where $R^3$ is hydrogen. A compound of Formula (H) may be prepared from 4-(1H-imidazol-2-yl)-piperidine-1-carboxylic acid tert butyl ester. First the $P'_c$ is added, then the compound is reacted with N-bromosuccinimide to form a 4,5-disubstituted compound and finally this is converted to the 4-bromo substituted compound (H) by reaction with n-butyl lithium (nBuLi) at reduced temperatures. $P'_c$ may be converted to the desired $P_c$ group by the methods set out above.

The compound of formula (D) where $R^3$ is a hydroxy group is synthesized as shown in the middle sequence of Scheme 2. First, an imidazole compound of formula (F) is formed by reaction of an acyl bromide of formula (E) and formamide at elevated temperature. The imidazole compound of formula (F) is then alkylated under similar alkylation conditions as described above to provide a compound of formula (G). Imidazole compound (G) is treated with a metalating agent, such as nBuLi, in a solvent such as THF, under reduced temperatures and an inert atmosphere, followed by a ring nitrogen protected 4-piperdinone to give the compound of formula (D).

The piperidine protection group of formula (D) is then removed to provide a compound of formula (1).

The amine of formula (A) and acyl bromide of formula (E) are either commercially available, or are synthesized by methods known in the art.

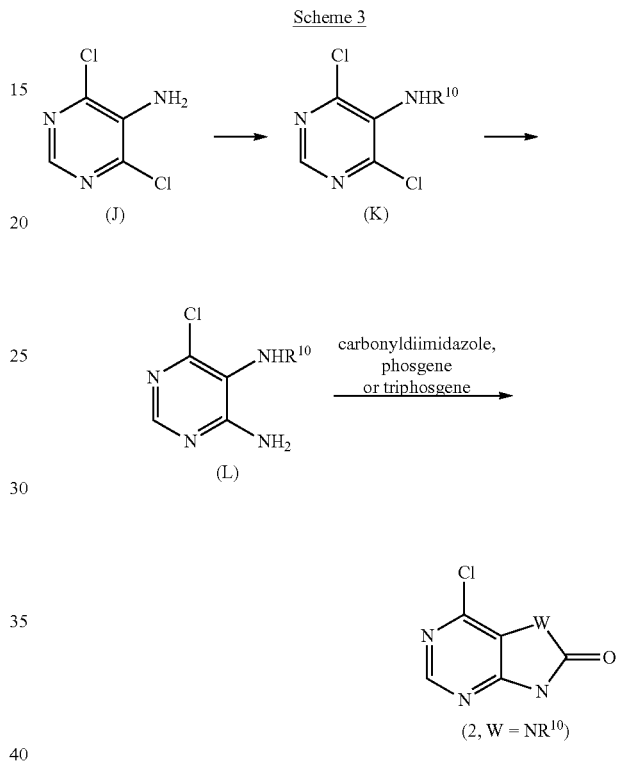

Scheme 3

The intermediates of formula (2), where W=NR$^{10}$, are either commercially available, or are synthesized by methods known to the skilled artisan. For example, 5-amino-4,6-dichloropyrimidine (J) is alkylated with an R$^{10}$-halide in the presence of a strong base to give the N-alkylated pyrimidine (K). One of the chlorides in compound (K) is displaced by ammonia by heating in a sealed vessel to give the pyrimidine diamine (L). Cyclization with phosgene, triphosgene or carbonyldiimidazole gives the intermediate (2) where W=NR$^{10}$.

Scheme 4
The intermediates of formula (2), where W = CR$^4$R$^5$ or C = CH–R$^9$, are synthesized bymethods known to the skilled artisan. For example,

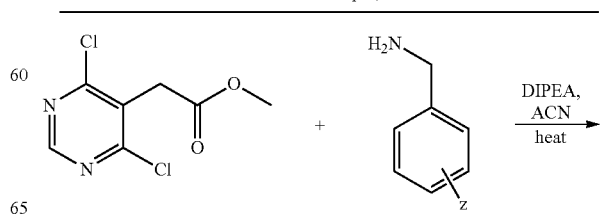

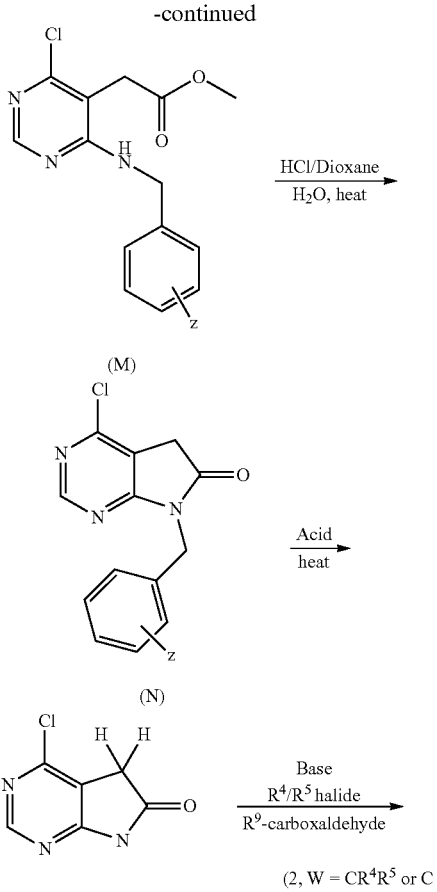

Z = 4-methoxy, 2-4-di-methoxy

Methyl 2-(4,6-dichloropyrimidin-5-yl)acetate may be prepared from methyl 2-(4,6-dihydroxypyrimidin-5-yl)acetate. The dihydroxy compound may in turn be prepared by adding 1,1,2-ethane tricarboxylic acid triethyl ester to a solution of sodium methoxide in methanol, followed by addition of formamidine hydrochloride.

Methyl 2-(4,6-dichloropyrimidin-5-yl)acetate is reacted with 4-methoxybenzylamine or 2,4-dimethoxybenzylamine in the presence of base, e.g., DIPEA and a solvent, e.g., acetonitrile (ACN) to give the benzyl protected acetate (M). Treatment of compound (M) in aqueous acid and heat gives the benzyl protected purinone (N). Compound (N) is deprotected in strong acid, e.g., trifluoroacetic acid (TFA) or 40% HBr aqueous and heat to give the known intermediate 4-chloro-5,7-dihydro-pyrrolo[2,3-d]pyrimidin-6-one.

4-Chloro-5,7-dihydro-pyrrolo[2,3-d]pyrimidin-6-one may be prepared from 5,5-dibromo-4-chloro-5,7-dihydro-pyrrolo[2,3-d]pyrimidin-6-one which is in turn prepared from 4-chloro-7H-pyrrolo[2,3-d]pyrimidine by reaction with pyridinium bromide perbromide.

4-Chloro-5,7-dihydro-pyrrolo[2,3-d]pyrimidin-6-one is either alkylated with an $R^4/R^5$-halide and base or condensed with an $R^9$-carboxaldehyde to give compound (2). The compound of formula (2) wherein $R^4$ and $R^5$ together form a cyclopentane ring is formed from 4-chloro-5,7-dihydro-pyrrolo[2,3-d]pyrimidin-6-one by reaction with 1,4-diiodobutane.

In an alternative method, the benzyl protected compound (N) is used in place of compound (2) in the coupling reactions of Scheme 1 followed by removal of the benzyl protection group.

The skilled artisan will appreciate that not all of the substituents in the compounds of Formula I will tolerate certain reaction conditions employed to synthesize the compounds. These moieties may be introduced at a convenient point in the synthesis, or may be protected and then de-protected as necessary or desired. The skilled artisan will also appreciate that the protecting groups may be removed at any convenient point in the synthesis of the compounds of the present invention. Methods for introducing and removing nitrogen protecting groups are well known in the art; see, for example, Greene and Wuts, "Protective Groups in Organic Synthesis", $3^{rd}$ Ed., John Wiley and Sons, New York, Chapter 7 (1999). Furthermore, the skilled artisan will appreciate than in many circumstances, the order in which moieties are introduced is not critical. The particular order of steps required to produce the compounds of Formula I is dependent upon the particular compound being synthesized, the starting compound and the relative liability of the substituted intermediates and products.

Preparation 1

2-Amino-1-(4-fluoro-3-(trifluoromethyl)phenyl)ethanone, 4-methylbenzenesulfonate Add sodium azide (1.76 g; 1.05 equivalents (equiv)) in one portion to a solution of 2-bromo-1-(4-fluoro-3-(trifluoromethyl)phenyl)ethanone (9.19 g; 1.00 equiv) in THF (50 mL). Stir the mixture at room temperature (RT) overnight. Filter the solids and wash with THF. Add the crude azide to a solution of triphenylphosphine (1.06 equiv; 8.64 g) and p-toluenesulfonic acid (2.2 equiv; 12.0 g) in THF (50 mL) under 20° C. Stir the mixture overnight. Filter the solid, and then wash with THF to obtain 5.5 g of the title compound. MS(ES): m/z=217.2 [M+H].

Prepare the following intermediates in a manner similar to that described in preparation 1:

| Preparation | Compound Name | Physical Chemistry Data |
|---|---|---|
| 2 | 2-Amino-1-(3-chloro-4-fluorophenyl)ethanone 4-methylbenzenesulfonate | $^1$H NMR (DMSO-$d_6$, 300 MHz): δ: 8.25 (m, 4H), 8.05 (ddd, J = 8.7, 4.7, 2.3 Hz, 1H), 7.66 (t, J = 8.9 Hz, 1H), 7.48-7.46 (m, 2H), 7.11 (d, J = 8.0 Hz, 2H), 4.62 (s, 2H), 2.28 (s, 3H). |
| 3 | 2-Amino-1-(3,4-difluorophenyl)ethanone 4-methylbenzenesulfonate | $^1$H NMR (DMSO-$d_6$, 300 MHz): δ: 8.25 (s, 3H), 8.11 (ddd, J = 11.0, 7.9, 2.3 Hz, 1H), 7.95-7.90 (m, 1H), 7.70 (dt, J = 10.4, 8.4 Hz, 1H), 7.47 (d, J = 8.0 Hz, 2H), 7.11 (d, J = 7.7 Hz, 2H), 4.60 (s, 2H), 2.28 (s, 3H). |

Preparation 4

2-Amino-1-(4-fluoro-3-(trifluoromethyl)phenyl)ethanone, hydrochloride

To a solution of 2-bromo-1-(4-fluoro-3-(trifluoromethyl)phenyl)ethanone (60.00 g 1.00 equiv; 210.50 mmoles (mmol)) in ethylacetate (EA) (450 mL; 4.60 moles (mol)), add 1,3,5,7-tetraazatricyclo-[3.3.1.13,7]decane (Methenamine, 1.10 equiv; 231.55 mmol; 32.46 g) and stir at RT overnight. Remove the solvent in vacuo and triturate the solid with methyl-t-butylether (MTBE), filter and dry in vacuo. Add ethanol (450 mL; 7.73 mol) followed by hydrogen chloride (36.5 wt/wt % in water) (150 mL; 8.30 equiv; 1.75 mol) and stir the mixture overnight. Remove the solvent in vacuo and dry the solid in vacuo at 50° C. for 1 week to give the title compound (54.23 g; 100% yield) as a white solid with some amount of ammonium salt. $^1$H NMR (300 MHz, DMSO): 8.69-8.59 (m, 4H), 8.07-8.01 (m, 1H), 4.95 (d, J=5.2 Hz, 2H). Use the solid as is.

Preparation 5

4-(2-(4-Fluoro-3-(trifluoromethyl)phenyl)-2-oxoethylcarbamoyl)piperidine-1-carboxylic acid tert-butyl ester To a solution of piperidine-1,4-dicarboxylic acid mono-tert-butyl ester (1.20 equiv; 252.61 mmol; 57.92 g) in THF (400 mL), add NMM (3 equiv; 631.52 mmol; 69.66 mL). Cool to −10° C. with a dry ice-acetone bath. Add isobutyl chloroformate (1.1 equiv; 231.56 mmol; 30.26 mL) dropwise maintaining the temperature below −5° C. After 30 min at from −5 to 10° C., add 2-amino-1-(4-fluoro-3-(trifluoromethyl)-phenyl)-ethanone hydrochloride (54.23 g; 1.00 equiv; 210.51 mmol) suspended in THF (300 mL) and stir the mixture in the bath at −5° C. for 20 min and then 1 h at RT. Partition between water and EA; wash the organic layer with water then saturated NaCl aqueous (brine), dry over anhydrous MgSO$_4$, filter and concentrate in vacuo. Suspend the crude in MTBE and stir for 2 h. Filter the solid and dry in vacuo to give the title compound (64.44 g; 70.79%). $^1$H NMR (300 MHz, DMSO): 8.37-8.26 (m, 3H), 7.74-7.68 (m, 1H), 4.61 (d, J=5.5 Hz, 2H), 3.91 (d, J=12.9 Hz, 2H), 2.75-2.64 (m, 2H), 2.46-2.37 (m, 1H), 1.69-1.60 (m, 2H), 1.39 (s, 12H).

Prepare the following intermediates in a manner similar to that described in preparation 5:

| Preparation | Compound Name | MS (ES): m/z (M + H − tBu) |
|---|---|---|
| 6 | 4-(2-(3-Chloro-4-fluorophenyl)-2-oxoethylcarbamoyl)piperidine-1-carboxylic acid tert-butyl ester | 343.1 |
| 7 | 4-(2-(3,4-Difluorophenyl)-2-oxoethylcarbamoyl)piperidine-1-carboxylic acid tert-butyl ester | 327.1 |

Preparation 8

4-[4-(4-Fluoro-3-trifluoromethyl-phenyl)-1H-imidazol-2-yl]-piperidine-1-carboxylic acid tert-butyl ester

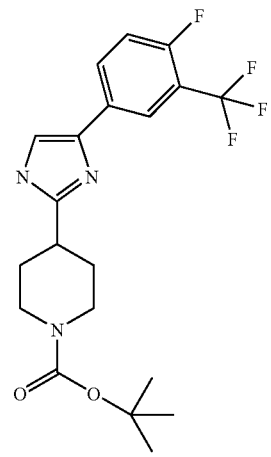

To a solution of 4-(2-(4-fluoro-3-(trifluoromethyl)phenyl)-2-oxoethylcarbamoyl)piperidine-1-carboxylic acid tert-butyl ester (29.4 g; 1.00 equiv; 67.99 mmol) in 1-butanol (150 mL; 1.64 mol), add ammonium acetate (15 equiv; 1.02 mol; 78.61 g) followed by TEA (1 equiv; 67.99 mmol; 9.48 mL). Stir the mixture at 160° C. in a sealed tube. After 3 h, cool to RT and partition between EA and water and wash the organic layer with water and brine. Concentrate in vacuo. Triturate the residue in MTBE, filter and dry in vacuo to give the title compound (18.23 g; 44.10 mmol; 64.86%) as a white solid. $^1$H NMR (300 MHz, DMSO): 12.01 (s, 1H), 8.08-8.04 (m, 2H), 7.70 (d, J=1.4 Hz, 1H), 7.49-7.43 (m, 1H), 3.99 (d, J=12.6 Hz, 2H), 2.92-2.85 (m, 3H), 1.91-1.87 (m, 2H), 1.64-1.51 (m, 2H), 1.41 (s, 9H).

Prepare the following intermediates in a manner similar to that described in preparation 8:

| Preparation | Compound Name | MS (ES): m/z [M + H] |
|---|---|---|
| 9 | 4-[4-(3-Chloro-4-fluoro-phenyl)-1H-imidazol-2-yl]-piperidine-1-carboxylic acid tert-butyl ester | 380.1 |
| 10 | 4-[4-(3,4-Difluoro-phenyl)-1H-imidazol-2-yl]-piperidine-1-carboxylic acid tert-butyl ester | 364.2 |

Preparation 11

2-Oxo-2-phenylacetaldehyde

Add SeO$_2$ (4.6 g; 0.042 mol; 1.0 equiv), acetic acid (1.2 mL; 0.021 mol; 0.5 equiv), water (1.5 mL; 0.083 mol; 2.0 equiv) in 1,4-dioxane (15 mL) and stir at 80° C. until the solution becomes clear. Cool the reaction to RT, add acetophenone (5.0 g; 0.042 mol; 1.0 equiv) and stir at 80° C. for 18 h. Cool the reaction to RT, filter through Celite®, wash the residue with EA, and dry over anhydrous sodium sulfate.

Evaporate the organic layer, purify over 50 g silica using EA in hexane to produce the title compound (4.0 g, 72.7%). MS (ES+): m/z=135 (M+H)

Preparation 12

4-(4-Phenyl-1H-imidazol-2-yl)-piperidine-1-carboxylic acid tert-butyl ester

Combine 4-formyl-piperidine-1-carboxylic acid tert-butyl ester (3.8 g; 0.017 mol; 0.6 equiv) and 2-oxo-2-phenylacetaldehyde (4.0 g; 0.29 mol; 1.0 equiv) in methanol (40 mL). Cool the reaction from 0 to 10° C. Add ammonium hydroxide solution (25% solution, 40 mL) slowly. Stir the reaction at RT for 16 h. Concentrate the reaction under vacuum, quench with water and extract with diethyl ether. Concentrate the organic layer and filter the solids, wash with hexane and dry under vacuum to give the title compound (3.0 g, 51.7%). MS (ES+): m/z=328 (M+H)

Preparation 13

4-[4-(3-Chloro-4-fluoro-phenyl)-1-(2-dimethylamino-ethyl)-1H-imidazol-2-yl]-piperidine-1-carboxylic acid tert-butyl ester Add (2-chloro-ethyl)-dimethyl-amine hydrochloride (1.10 equiv; 579 µmol; 83 mg) in one portion to a mixture of 4-[4-(3-chloro-4-fluoro-phenyl)-1H-imidazol-2-yl]-piperidine-1-carboxylic acid tert-butyl ester (1 equiv; 526 µmol; 200 mg) and powdered KOH (2.5 equiv; 1.316 mmol; 73.8 mg) in DMSO (3 mL). Warm to 50° C. and stir for 2 h. Dilute with DCM, wash with water, brine, dry over MgSO$_4$, filter, evaporate and purify on 40 g silica gel with 10% methanol/ACN to provide the title compound (194 mg; 0.43 mmol; 82%). MS (ES+): m/z=451 (M+H).

Prepare the following intermediates in a manner similar to that described in preparation 13:

| Preparation | Compound Name | MS (ES): m/z (M + H) |
|---|---|---|
| 14 | 4-[1-(2-Dimethylamino-ethyl)-4-(4-fluoro-3-trifluoromethyl-phenyl)-1H-imidazol-2-yl]-piperidine-1-carboxylic acid tert-butyl ester | 485 |
| 15 | 4-[4-(3-Chloro-4-fluoro-phenyl)-1-(2-pyrrolidin-1-yl-ethyl)-1H-imidazol-2-yl]-piperidine-1-carboxylic acid tert-butyl ester | 476 |
| 16 | 4-[4-(4-Fluoro-3-trifluoromethyl-phenyl)-1-(2-pyrrolidin-1-yl-ethyl)-1H-imidazol-2-yl]-piperidine-1-carboxylic acid tert-butyl ester | 511 |
| 17 | 4-[1-(2-Dimethylamino-2-methyl-propyl)-4-(4-fluoro-3-trifluoromethyl-phenyl)-1H-imidazol-2-yl]-piperidine-1-carboxylic acid tert-butyl ester | 513 |
| 18 | 4-(1-(2-(Dimethylamino)ethyl)-4-phenyl-1H-imidazol-2-yl)piperidine-1-carboxylic acid tert-butyl ester | 399 |

Preparation 19

4-[4-(3,4-Difluoro-phenyl)-1-(2-dimethylamino-ethyl)-1H-imidazol-2-yl]-piperidine-1-carboxylic acid tert-butyl ester Add 4-[4-(3,4-difluoro-phenyl)-1H-imidazol-2-yl]-piperidine-1-carboxylic acid tert-butyl ester (500 mg; 1.38 mmol) to a solution of NaH (110 mg; 2.76 mmol) in DMSO (50 mL) at 0° C., and stir for 1 h at RT. Add (N,N-dimethyl) ethyl chloride hydrochloride (238 mg; 1.65 mmol) to the resulting mixture and allow to stir at RT for 18 h. Monitor the reaction by thin layer chromatography (TLC). Quench the reaction mixture with ice water and extract with EA. Separate the organic layer, wash twice with brine (2×50 mL), dry over anhydrous Na$_2$SO$_4$ and evaporate under reduced pressure. Purify the residue by column chromatography on silica gel (60/120 mesh) using DCM:Methanol (98:2) as eluent to give 0.5 g (86%) of the title compound. LCMS=484(M+H).

Prepare the following intermediate in a manner similar to that described in preparation 19:

| Preparation | Compound Name | MS (ES): m/z (M + H) |
|---|---|---|
| 20 | 4-[4-(3,4-Difluoro-phenyl)-1-(2-(pyrrolidin-1-yl)ethyl)-1H-imidazol-2-yl]piperidine-1-carboxylic acid tert-butyl ester | 462 |

Preparation 21

4-{4-(3-Chloro-4-fluoro-phenyl)-1-[2-(tetrahydropyran-2-yloxy)-ethyl]-1H-imidazol-2-yl}-piperidine-1-carboxylic acid tert-butyl ester Dissolve 4-[4-(3-chloro-4-fluoro-phenyl)-1H-imidazol-2-yl]-piperidine-1-carboxylic acid tert-butyl ester (5.29 g; 13.93 mmol); powdered KOH (111.46 mmol; 6.95 g) in DMSO (69 mL) and heat to 40° C. for 10 min. Add 2-(2-bromoethoxy)tetrahydro-2H-pyran (34.83 mmol; 5.48 mL) dropwise over 45 min, then stir for 30 min. Cool and dilute with EA and wash with 3×300 mL saturated sodium bicarbonate, brine, dry over MgSO$_4$, filter and evaporate. Purify on 400 g silica gel with 0-10% EA/DCM to provide the title compound (6.848 g, 97%). MS (ES): m/z=508 (M+H).

Prepare the following intermediate in a manner similar to that described in preparation 21:

| Preparation | Compound Name | MS (ES): m/z (M + H) |
|---|---|---|
| 22 | 4-{4-(4-Fluoro-3-trifluoromethyl-phenyl)-1-[2-(tetrahydro-pyran-2-yloxy)-ethyl]-1H- | 542 |

| Preparation | Compound Name | MS (ES): m/z (M + H) |
|---|---|---|
| | imidazol-2-yl}-piperidine-1-carboxylic acid tert-butyl ester | |

Preparation 23

4-[4-(3-Chloro-4-fluoro-phenyl)-1-(2-hydroxy-ethyl)-1H-imidazol-2-yl]-piperidine-1-carboxylic acid tert-butyl ester Dissolve 4-{4-(3-chloro-4-fluoro-phenyl)-1-[2-(tetrahydro-pyran-2-yloxy)-ethyl]-1H-imidazol-2-yl}-piperidine-1-carboxylic acid tert-butyl ester (6.85 g; 13.48 mmol) in THF (200 mL) and add 1M aqueous hydrogen chloride (20 mL) and stir 18 h at RT. Dilute with EA, wash with saturated sodium bicarbonate, brine, dry with anhydrous $MgSO_4$, filter, and evaporate. Purify the residue on 330 g silica gel with 2:1 DCM/EA to provide the title compound (5.07 g; 89%) as a white crystalline solid. MS (ES): m/z=424 (M+H).

Prepare the following intermediates in a manner similar to that described in preparation 23:

| Preparation | Compound Name | MS (ES): m/z (M + H) |
|---|---|---|
| 24 | 4-[4-(4-Fluoro-3-trifluoromethyl-phenyl)-1-(2-hydroxy-ethyl)-1H-imidazol-2-yl]-piperidine-1-carboxylic acid tert-butyl ester | 458 |
| 25 | 4-[4-(3,4-Difluoro-phenyl)-1-(2-hydroxy-ethyl)-1H-imidazol-2-yl]-piperidine-1-carboxylic acid tert-butyl ester | 408 |

Preparation 26

4-[4-(3-Chloro-4-fluoro-phenyl)-1-(2-methanesulfonyloxy-ethyl)-1H-imidazol-2-yl]-piperidine-1-carboxylic acid tert-butyl ester Suspend 4-[4-(3-chloro-4-fluoro-phenyl)-1-(2-hydroxy-ethyl)-1H-imidazol-2-yl]-piperidine-1-carboxylic acid tert-butyl ester (5.07 g; 11.96 mmol) and TEA (35.88 mmol; 5.0 mL) in DCM (50 mL) and cool in ice bath. Add methanesulfonyl chloride (14.35 mmol; 1.1 mL) dropwise over 9 min and stir for 30 additional min. Quench with saturated sodium bicarbonate, dry over $MgSO_4$, filter and evaporate to provide the title compound (6.246 g; 104%) as a foam. MS (ES): m/z=502 (M+H).

Prepare the following intermediates in a manner similar to that described in preparation 26:

| Preparation | Compound Name | MS (ES): m/z (M + H) |
|---|---|---|
| 27 | 4-[4-(4-Fluoro-3-trifluoromethyl-phenyl)-1-(2-methanesulfonyloxy-ethyl)-1H-imidazol-2-yl]-piperidine-1-carboxylic acid tert-butyl ester | 536 |
| 28 | 4-[4-(3,4-Difluoro-phenyl)-1-(2-methanesulfonyloxy-ethyl)-1H-imidazol-2-yl]-piperidine-1-carboxylic acid tert-butyl ester | 486 |

Preparation 29

4-{4-(4-Fluoro-3-trifluoromethyl-phenyl)-1-[2-((R)-2-hydroxymethyl-pyrrolidin-1-yl)-ethyl]-1H-imidazol-2-yl}-piperidine-1-carboxylic acid tert-butyl ester Add 4-[4-(4-fluoro-3-trifluoromethyl-phenyl)-1-(2-methanesulfonyloxy-ethyl)-1H-imidazol-2-yl]-piperidine-1-carboxylic acid tert-butyl ester (500 mg; 1 equiv; 933 μmol); D-prolinol (3.00 equiv; 2.80 mmol; 283 mg); DMF (1 mL) and heat at 50° C. for 18 h in a sealed vessel. Dilute with EA, wash with saturated sodium bicarbonate, brine, dry $MgSO_4$, filter and purify on 40 g silica gel with 1-10% MeOH/DCM to provide the title compound (506.9 mg; 0.94 mmol; 100%). MS (ES+): m/z=541 (M+H).

Prepare the following intermediates in a manner similar to that described in preparation 29:

| Preparation | Compound Name | MS (ES): m/z (M + H) |
|---|---|---|
| 30 | 4-{4-(4-Fluoro-3-trifluoromethyl-phenyl)-1-[2-(isopropyl-methyl-amino)-ethyl]-1H-imidazol-2-yl}-piperidine-1-carboxylic acid tert-butyl ester | 513 |
| 31 | 4-{4-(3-Chloro-4-fluoro-phenyl)-1-[2-(isopropyl-methyl-amino)-ethyl]-1H-imidazol-2-yl}-piperidine-1-carboxylic acid tert-butyl ester | 479 |
| 32 | 4-[1-(2-tert-Butylamino-ethyl)-4-(4-fluoro-3-trifluoromethyl-phenyl)-1H-imidazol-2-yl]-piperidine-1-carboxylic acid tert-butyl ester | 513 |
| 33 | 4-[1-(2-tert-Butylamino-ethyl)-4-(3-chloro-4-fluoro-phenyl)-1H-imidazol-2-yl]-piperidine-1-carboxylic acid tert-butyl ester | 479 |
| 34 | 4-{4-(3-Chloro-4-fluoro-phenyl)-1-[2-(ethyl-isopropyl-amino)-ethyl]-1H-imidazol-2-yl}-piperidine-1-carboxylic acid tert-butyl ester | 493 |

Preparation 35

4-[1-[2-(tert-Butyl-dimethyl-silanyloxy)-ethyl]-4-(3,4-difluoro-phenyl)-1H-imidazol-2-yl]-piperidine-1-carboxylic acid tert-butyl ester Combine 4-[4-(3,4-difluoro-phenyl)-1H-imidazol-2-yl]-piperidine-1-carboxylic acid tert-butyl ester (10.0 g; 0.028 mol; 1.0 equiv), (2-bromo-ethoxy)-tert-butyl-dimethyl-silane (13.16 g; 0.055 mol; 2.0 equiv), powdered KOH (7.72 g; 0.14 mol; 5.0 equiv) in THF (100 mL) and stir at 40° C. for 16 h. Quench the reaction with water and extract with EA. Evaporate to give the title compound (14.3 g, crude). MS (ES+): m/z=522 (M+H)

Preparation 36

4-[4-(3,4-Difluoro-phenyl)-1-(2-hydroxy-ethyl)-1H-imidazol-2-yl]-piperidine-1-carboxylic acid tert-butyl ester Combine 4-[1-[2-(tert-butyl-dimethyl-silanyloxy)-ethyl]-4-(3,4-difluoro-phenyl)-1H-imidazol-2-yl]-piperidine-1-carboxylic acid tert-butyl ester (18.3 g; 0.035 mol; 1.0 equiv), tetrabutylammonium fluoride (20.3 g; 0.07 mol; 2.0 equiv) in THF (100 mL) and stir at RT for 3 h. Concentrate, quench the reaction with water and extract with EA. Evaporate the organic layer to give the title compound (3.5 g; 24.49%). MS (ES+): m/z=408(M+H).

Preparation 37

4-(4-(3,4-Difluoro-phenyl)-1-{2-[(2-hydroxy-ethyl)-methyl-amino]-ethyl}-1H-imidazol-2-yl)-piperidine-1-carboxylic acid tert-butyl ester Combine 4-[4-(3,4-difluoro-phenyl)-1-(2-methanesulfonyloxy-ethyl)-1H-imidazol-2-yl]-piperidine-1-carboxylic acid tert-butyl ester (3.0 g; 0.0061 mol; 1.0 equiv), 2-methylamino-ethanol (1.48 g; 0.031 mol; 5.0 equiv) in DMF (30 mL) and stir at 40-50° C. for 16 h. Quench with water and extract with diethyl ether. Evaporate the organic layer, purify over 50 g silica gel with 0 to 10% MeOH/DCM. Pool fractions to produce the title compound (1.5 g; 52.2%) MS (ES+): m/z=465 (M+H).

Prepare the following intermediates in a manner similar to that described in preparation 37:

| Preparation | Compound Name | MS (ES): m/z (M + H) |
|---|---|---|
| 38 | 4-(4-(3,4-Difluorophenyl)-1-(2-(3-hydroxypyrrolidin-1-yl)ethyl)-1H-imidazol-2-yl)piperidine-1-carboxylic acid tert-butyl ester | 477 |
| 39 | 4-(1-(2-(3-(tert-Butyl-dimethyl-silanyloxy)azetidin-1-yl)ethyl)-4-(3,4-difluorophenyl)-1H-imidazol-2-yl)piperidine-1-carboxylic acid tert-butyl ester | 577 |

Preparation 40

Benzyl-(2-chloro-ethyl)-methylamine, hydrochloride

Combine hydrogen chloride (50 mL; 4M in dioxane), N-benzyl-N-methylethanolamine (61.12 mmol; 10 g), thionyl chloride (73.30 mmol; 5.34 mL) and heat to 90° C. Stir for 2 h, evaporate and crush the solids under ether, sonicate 15 min, filter, wash with ether, dry under vacuum to provide the title compound (10.75 g; 80%). MS (ES): m/z=184 (M+H).

Prepare the following intermediate in a manner similar to that described for benzyl-(2-chloro-ethyl)-methylamine, hydrochloride from 1-phenylmethyl-(2R)-pyrrolidinemethanol:

| Preparation | Compound Name | MS (ES): m/z (M + H) |
|---|---|---|
| 41 | (R)-1-Benzyl-2-chloromethyl-pyrrolidine hydrochloride | 210 |

Preparation 41a

(R)-1-Benzyl-2-(bromomethyl)piperidine hydrochloride

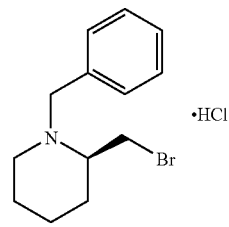

Charge (R)-(1-benzylpiperidin-2-yl)methanol (30.0 g, 0.146 mol, ~1.0 eq., crude) in 350 mL benzene and add a solution of phosphorus tribromide (20.6 mL, 0.219 mol, 1.5 eq) in benzene at 0° C. under nitrogen atmosphere. Heat the reaction mass at 70° C. for 16 h. After completion of reaction, quench the reaction with saturated solution of sodium carbonate (100 mL) and extract the compound in EA (3×100 mL). Wash the organic layer with brine and dry over anhydrous sodium sulfate. Concentrate under reduced pressure and dissolve the solid residue in diethyl ether. Filter the dissolved portion and add slowly HCl (1.2 eq, 2 N in diethyl ether) and stir for 30 minutes at RT. Filter the precipitated salt and wash with EA followed by hexane. Dry under high vacuum to get 13.2 g of (R)-1-benzyl-2-(bromomethyl)piperidine as hydrochloride salt. MS(ES): m/z=268, 270 (M+H).

Prepare the following intermediate in a manner similar to that described in preparation 41a:

| Preparation | Compound Name | MS (ES): m/z (M + H) |
|---|---|---|
| 41b | (S)-1-Benzyl-2-(bromomethyl)-piperidine hydrochloride | 268, 270 |

Preparation 42

4-[1-[2-(Benzyl-methyl-amino)-ethyl]-4-(3-chloro-4-fluoro-phenyl)-1H-imidazol-2-yl]-piperidine-1-carboxylic acid tert-butyl ester Add powdered KOH (283 mg; 5.05 mmol) and 4-[4-(3-chloro-4-fluoro-phenyl)-1H-imidazol-2-yl]-piperidine-1- carboxylic acid tert-butyl ester (2.02 mmol; 768 mg) to DMSO (6 mL). Then add benzyl-(2-chloro-ethyl)-methylamine hydrochloride (2.22 mmol; 0.49 mL) in one portion and heat to 40° C. for 18 h. Cool, dilute with DCM/water, add brine and separate layers. Wash the organic phase with water, brine, dry over MgSO₄, filter and evaporate. Purify on 120 g silica gel with 1% MeOH/DCM to provide the title compound (840.5 mg; 79%). MS (ES): m/z=527 (M+H).

Prepare the following intermediates in a manner similar to that described in preparation 42:

| Preparation | Compound Name | MS (ES): m/z (M + H) |
|---|---|---|
| 43 | 4-[1-[2-(Benzyl-methyl-amino)-ethyl]-4-(4-fluoro-3-trifluoromethyl-phenyl)-1H-imidazol-2-yl]-piperidine-1-carboxylic acid tert-butyl ester | 561 |
| 44 | 4-[1-[2-(Benzyl-methyl-amino)-ethyl]-4-(3,4-difluoro-phenyl)-1H-imidazol-2-yl]-piperidine-1-carboxylic acid tert-butyl ester | 511 |
| 45 | 4-[1-((S)-1-Benzyl-pyrrolidin-2-ylmethyl)-4-(3-chloro-4-fluoro-phenyl)-1H-imidazol-2-yl]-piperidine-1-carboxylic acid tert-butyl ester | 553 |
| 46 | 4-[1-(R)-1-Benzyl-pyrrolidin-2-ylmethyl)-4-(3-chloro-4-fluoro-phenyl)-1H-imidazol-2-yl]-piperidine-1-carboxylic acid tert-butyl ester | 553 |

Preparation 46a (R) 4-(1-((1-Benzylpiperidin-2-yl)methyl)-4-(4-fluoro-3-trifluoromethyl-phenyl)-1H-imidazol-2-yl) piperidine-1-carboxylic acid tert-butyl ester

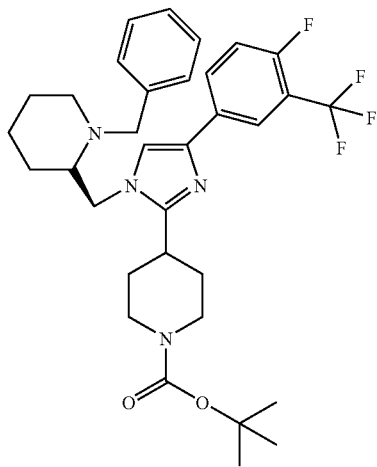

To a solution of 4-[4-(4-fluoro-3-trifluoromethyl-phenyl)-1H-imidazol-2-yl]-piperidine-1-carboxylic acid tert-butyl ester (4.5 g, 0.011 mol, 1.0 eq) in DMSO (100 mL) and add powdered KOH (3.0 g, 0.055 mol, 5.0 eq) at RT under nitrogen atmosphere and stir for 30 minutes. To the resulting solution add (R)-1-benzyl-2-(bromomethyl)piperidine hydrochloride (5.0 g, 0.0165 mol, 1.5 eq) and stir the reaction mass at RT for 16 h. After completion, dilute the reaction with water (100 mL) and extract the compound in EA (3×100 mL). Wash the organic layer with brine (2×50 mL) and dry over anhydrous sodium sulfate. Concentrate the organic layer under reduced pressure and purify on silica (100-200 mesh) using 2% acetone-DCM to get 3.0 g (46%) of the title compound. (ES+): m/z=601 (M+H).

Prepare the following intermediate in a manner similar to that described in preparation 46a:

| Preparation | Compound Name | MS (ES): m/z (M + H) |
|---|---|---|
| 46b | (S) 4-(1-((1-Benzylpiperidin-2-yl)methyl)-4-(4-fluoro-3-trifluoromethyl-phenyl)-1H-imidazol-2-yl)piperidine-1-carboxylic acid tert-butyl ester | 601 |

Preparation 47

4-[4-(3-Chloro-4-fluoro-phenyl)-1-(2-methylamino-ethyl)-1H-imidazol-2-yl]-piperidine-1-carboxylic acid tert-butyl ester Dissolve 4-[1-[2-(benzyl-methyl-amino)-ethyl]-4-(3-chloro-4-fluoro-phenyl)-1H-imidazol-2-yl]-piperidine-1-carboxylic acid tert-butyl ester (1.47 mmol; 775 mg); 1,8-naphthalenediamine, N,N,N',N'-tetramethyl-(0.044 mmol; 9.4 mg) in 1,2-dichloroethane (DCE 20 mL) and cool in an ice bath. Add 1-chloroethyl chloroformate (4.41 mmol; 0.48 mL) dropwise over a couple of min to give a colorless solution; stir 15 min; then remove ice bath and heat to 70° C. for 2 h. Cool to RT and evaporate. Dissolve the residue in methanol (20 mL) and heat to reflux for 40 min, evaporate and dissolve the residue in DCM, wash with sodium bicarbonate, brine, dry over MgSO₄, filter, evaporate to provide the title compound (681 mg; 106%). MS (ES): m/z=437 (M+H).

Prepare the following intermediates in a manner similar to that described in preparation 47:

| Preparation | Compound Name | MS (ES): m/z (M + H) |
|---|---|---|
| 48 | 4-[4-(4-Fluoro-3-trifluoromethyl-phenyl)-1-(2-methylamino-ethyl)-1H-imidazol-2-yl]-piperidine-1-carboxylic acid tert-butyl ester | 471 |
| 49 | 4-[4-(3-Chloro-4-fluoro-phenyl)-1-(S)-1-pyrrolidin-2-ylmethyl-1H-imidazol-2-yl]-piperidine-1-carboxylic acid tert-butyl ester | 463 |
| 50 | 4-[4-(3-Chloro-4-fluoro-phenyl)-1-(R)-1-pyrrolidin-2-ylmethyl-1H-imidazol-2-yl]-piperidine-1-carboxylic acid tert-butyl ester | 463 |

Preparation 51

4-[1-[2-(Benzyloxycarbonyl-methyl-amino)-ethyl]-4-(3-chloro-4-fluoro-phenyl)-1H-imidazol-2-yl]-piperidine-1-carboxylic acid tert-butyl ester Dissolve 4-[4-(3-chloro-4-fluoro-phenyl)-1-(2-methylamino-ethyl)-1H-imidazol-2-yl]-piperidine-1-carboxylic acid tert-butyl ester (1.56 mmol; 680 mg) in DCM (10 mL) and add benzyl chloroformate (1.56 mmol; 0.23 mL) and DIPEA (3.11 mmol; 0.54 mL). Stir 15 min and evaporate. Purify the residue on 120 g silica gel with DCM to 20% EA/DCM to provide the title compound (741 mg; 83%). MS (ES): m/z=571 (M+H).

Prepare the following intermediates in a manner similar to that described in preparation 51:

| Preparation | Compound Name | MS (ES): m/z (M + H) |
|---|---|---|
| 52 | 4-[1-[2-(Benzyloxycarbonyl-methyl-amino)-ethyl]-4-(4-fluoro-3-trifluoromethyl-phenyl)-1H-imidazol-2-yl]-piperidine-1-carboxylic acid tert-butyl ester | 605 |
| 53 | 4-[1-((S)-1-Benzyloxycarbonyl-pyrrolidin-2-ylmethyl)-4-(3-chloro-4-fluoro-phenyl)-1H-imidazol-2-yl]-piperidine-1-carboxylic acid tert-butyl ester | 597 |
| 54 | 4-[1-((R)-1-Benzyloxycarbonyl-pyrrolidin-2-ylmethyl)-4-(3-chloro-4-fluoro-phenyl)-1H-imidazol-2-yl]-piperidine-1-carboxylic acid tert-butyl ester | 597 |

Preparation 55

4-[1-[2-(Benzyloxycarbonyl-methyl-amino)-ethyl]-4-(3,4-difluoro-phenyl)-1H-imidazol-2-yl]-piperidine-1-carboxylic acid tert-butyl ester Charge 4-[1-[2-(benzyl-methyl-amino)-ethyl]-4-(3,4-difluoro-phenyl)-1H-imidazol-2-yl]-piperidine-1-carboxylic acid tert-butyl ester (1.8 g; 0.0035 mol; 1.0 equiv) in ACN (40 mL) under nitrogen and add benzyl chloroformate drop wise at 0° C. Stir the reaction for 30 min and bring to RT. Stir at RT for 1.5 h. After completion, quench the reaction with saturated sodium bicarbonate solution and extract in EA. Wash with water and brine, dry over anhydrous sodium sulfate and evaporate off the solvent under vacuum. Purify on silica column using 15% EA/hexane to get the title compound (1.6 g; 82%). (ES+): m/z=555 (M+H).

Preparation 55a (R)-Benzyl 2-((2-(1-(tert-butoxycarbonyl)piperidin-4-yl)-4-(4-fluoro-3-(trifluoromethyl)phenyl)-1H-imidazol-1-yl)methyl)piperidine-1-carboxylate

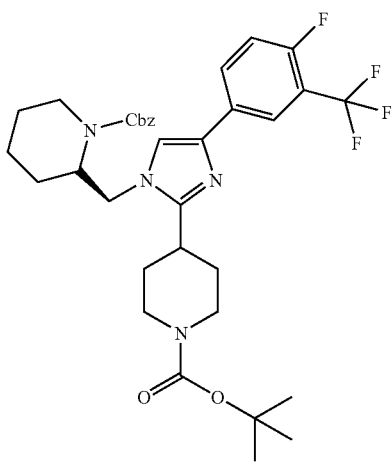

Dissolve (R) 4-(1-((1-benzylpiperidin-2-yl)methyl)-4-(4-fluoro-3-trifluoromethyl phenyl)-1H-imidazol-2-yl)piperidine-1-carboxylic acid tert-butyl ester (3.0 g, 0.005 mol, 1.0 eq) in toluene (15 mL) and add benzyl chloroformate (8.5 mL, 50% in toluene, 0.025 mol, 5.0 eq) at 0° C. under nitrogen atmosphere. Stir the reaction mass at RT for 16 h. After completion, quench the reaction mass with aqueous sodium bicarbonate solution and extract in EA (3×100 mL) and wash the organic layer with aqueous sodium bicarbonate solution (3×50 mL) and dry over anhydrous sodium sulfate. Concentrate under reduced pressure and purify the crude compound on silica gel (100-200 mesh) column using 2.5% acetone-DCM as eluent to get 2.6 g (81%) of the title compound as greenish-yellow gummy liquid. (ES+): m/z=645 (M+H).

Prepare the following intermediate in a manner similar to that described in preparation 55a:

| Preparation | Compound Name | MS (ES): m/z (M + H) |
|---|---|---|
| 55b | (S)-Benzyl 2-((2-(1-(tert-butoxycarbonyl)-piperidin-4-yl)-4-(4-fluoro-3-(trifluoromethyl)-phenyl)-1H-imidazol-1-yl)methyl)piperidine-1-carboxylate | 645 |

Preparation 56

4-[1-(1-Benzyloxycarbonyl-pyrrolidin-2-ylmethyl)-4-(4-fluoro-3-trifluoromethyl-phenyl)-1H-imidazol-2-yl]-piperidine-1-carboxylic acid tert-butyl ester In a dry round bottom flask, charge 4-[4-(4-fluoro-3-trifluoromethyl-phenyl)-1H-imidazol-2-yl]-piperidine-1-carboxylic acid tert-butyl ester (1.5 g; 0.0036 mol; 1.0 equiv) in dry DMF (30 mL) and cool to 0° C. Add NaH (0.26 g; 0.011 mol; 3.0 equiv) in portions under nitrogen and stir at RT for 30 min. Add 2-(toluene-4-sulfonyloxymethyl)-pyrrolidine-1-carboxylic acid benzyl ester (2.46 g; 0.0072 mol; 2.0 equiv) at RT and heat at 40° C. overnight. Quench with cold water and extract in EA. Wash the organic layer with water and brine. Dry over anhydrous sodium sulfate and concentrate. Purify the crude residue on silica (100-200 mesh) with 10 to 20% EA/hexanes to give the title compound (1.14 g; 51.6%). (ES+): m/z=631 (M+H).

Prepare the following intermediate in a manner similar to that described in preparation 56:

| Preparation | Compound Name |
|---|---|
| 57 | 4-[1-(1-Benzyloxycarbonyl-pyrrolidin-2-yl-methyl)-4-(3,4-difluorophenyl)-1H-imidazol-2-yl]-piperidine-1-carboxylic acid tert-butyl ester |

Reference Preparation 58

4-[1-(2-Benzyloxycarbonylamino-ethyl)-4-(3-chloro-4-fluoro-phenyl)-1H-imidazol-2-yl]-piperidine-1-carboxylic acid tert-butyl ester Dissolve 4-[1-(2-amino-ethyl)-4-(3-chloro-4-fluoro-phenyl)-1H-imidazol-2-yl]-piperidine-1-carboxylic acid tert-butyl ester (0.94 mmol; 396.7 mg) in DCM (20 mL) and add DIPEA (1.41 mmol; 0.25 mL) and benzyl chloroformate (0.94 mmol; 0.14 mL). Stir 20 min and wash with saturated sodium bicarbonate, dry over MgSO$_4$, filter and evaporate.

Purify over 40 g silica gel with 0-40% EA/DCM to provide the title compound (222 mg; 42%). MS (ES): m/z=557 (M+H).

Prepare the following intermediate in a manner similar to that described in reference preparation 58:

| Preparation | Compound Name |
|---|---|
| 59 | 4-[1-(2-Benzyloxycarbonylamino-ethyl)-4-(4-fluoro-3-trifluoromethyl-phenyl)-1H-imidazol-2-yl]-piperidine-1-carboxylic acid tert-butyl ester |

Reference Preparation 60

4-[4-(3-Chloro-4-fluoro-phenyl)-1-cyanomethyl-1H-imidazol-2-yl]-piperidine-1-carboxylic acid tert-butyl ester Combine 4-[4-(3-chloro-4-fluoro-phenyl)-1H-imidazol-2-yl]-piperidine-1-carboxylic acid tert-butyl ester (2.55 mmol; 969 mg), tetra-N-butylammonium bromide (0.26 mmol; 82 mg), 50 wt % aq sodium hydroxide (8.42 mmol; 0.45 mL) and DCM (25 mL). Add bromoacetonitrile (5.11 mmol; 0.36 mL) dropwise over 10 min. Stir 45 min and dilute with DCM, wash with brine, 50% saturated aqueous sodium chloride solution, dry over $MgSO_4$, filter and evaporate. Purify over 150 g silica gel with 20% EA/DCM to provide the title compound (812 mg; 76%). MS (ES): m/z=419 (M+H).

Prepare the following intermediate in a manner similar to that described in reference preparation 60:

| Preparation | Compound Name |
|---|---|
| 61 | 4-(1-(Cyanomethyl)-4-(4-fluoro-3-(trifluoro-methyl)-phenyl)-1H-imidazol-2-yl)piperidine-1-carboxylic acid tert-butyl ester |

Reference Preparation 62

4-[1-(2-Amino-ethyl)-4-(3-chloro-4-fluoro-phenyl)-1H-imidazol-2-yl]-piperidine-1-carboxylic acid tert-butyl ester Dissolve 4-[4-(3-chloro-4-fluoro-phenyl)-1-cyanomethyl-1H-imidazol-2-yl]-piperidine-1-carboxylic acid tert-butyl ester (0.94 mmol; 392.9 mg) in methanol (20 mL). Add nickel dichloride (1.03 mmol; 135 mg). Add sodium tetrahydroborate (18.8 mmol; 717 mg) portion-wise. Evaporate and partition between water/DCM and stir 20 min. Add Celite®, stir 30 min and filter. Rinse solids with DCM, 10% MeOH/DCM. Add 2 mL 2M $NH_3$-MeOH to organic layer and evaporate. Dissolve the residue in DCM, wash with brine, dry over $MgSO_4$, filter through Celite® and evaporate to provide the title compound (498 mg; 125%). MS (ES): m/z=423 (M+H).

Prepare the following intermediate in a manner similar to that described in reference preparation 62:

| Preparation | Compound Name | MS (ES): m/z (M + H) |
|---|---|---|
| 63 | 4-(1-(2-Aminoethyl)-4-(4-fluoro-3-(trifluoromethyl)phenyl)-1H-imidazol-2-yl)-piperidine-1-carboxylic acid tert-butyl ester | 457 |

Preparation 64

4-(4-Fluoro-3-(trifluoromethyl)phenyl)-1H-imidazole

Charge 2-bromo-1-(4-fluoro-3-trifluoromethyl-phenyl)-ethanone (40.0 g; 0.14 mol; 1.0 equiv) and formamide (175 mL; 4.38 mol; 31.3 equiv) in a pressure vessel. Heat at 180° C. for 3 h. Quench with saturated sodium bicarbonate solution and filter through Celite®. Extract with EA and wash the organic layer with water and brine. Concentrate and purify on silica column with 0-10% MeOH-EA to give the title compound. (15.2 g; 47.0%). (ES+): m/z=231 (M+H).

Prepare the following intermediate in a manner similar to that described in preparation 64:

| Preparation | Compound Name | MS (ES): m/z (M + H) |
|---|---|---|
| 65 | 4-(3-Chloro-4-fluoro-phenyl)-1H-imidazole | 197 |

Preparation 66

{2-[4-(3-Chloro-4-fluoro-phenyl)-imidazol-1-yl]-ethyl}-dimethylamine

Charge a round bottom flask with 4-(3-chloro-4-fluoro-phenyl)-1H-imidazole (1.85 g; 1.00 equiv; 9.41 mmol), KOH (3.00 equiv; 28.23 mmol; 1.58 g, crushed to a fine powder), in DMSO (281.56 mmol; 20.00 mL). Add 2-dimethylaminoethyl chloride hydrochloride (1.20 equiv; 11.29 mmol; 1.63 g) in one portion and the solution becomes yellow. Heat at 45° C. for 2 days. Dilute the reaction with EA and wash with water, brine and dry the organics over $MgSO_4$; filter, and concentrate to an orange oil. Purify the crude with ISCO chromatography over a Biotage 40M column eluting with a gradient of 5% MeOH/DCM to 10% MeOH/DCM at a flow rate of 40 mL/min to give the title compound (1.09 g; 4.07 mmol; 43.27%) as a light orange oil. MS(ES): (m/z)=268.0 (M+H).

Prepare the following intermediates in a manner similar to that described in preparation 66:

| Preparation | Compound Name | MS (ES): (m/z) [M + H] |
|---|---|---|
| 67 | 4-(3-Chloro-4-fluoro-phenyl)-1-(2-pyrrolidin-1-yl-ethyl)-1H-imidazole | 294 |
| 68 | 4-(4-Fluoro-3-(trifluoromethyl)phenyl)-1-(2-(pyrrolidin-1-yl)ethyl)-1H-imidazole | 328 |
| 69 | 2-(4-(4-Fluoro-3-(trifluoromethyl)phenyl)-1H-imidazol-1-yl)-N,N-dimethylethanamine | 302 |

Preparation 70

4-[4-(3-Chloro-4-fluoro-phenyl)-1-(2-dimethylamino-ethyl)-1H-imidazol-2-yl]-4-hydroxy-piperidine-1-carboxylic acid tert-butyl ester Dissolve {2-[4-(3-chloro-4-fluoro-phenyl)-imidazol-1-yl]-ethyl}-dimethylamine (1.00 equiv; 4.07 mmol; 1.09 g) in anhydrous THF (15 mL; 184.33 mmol) and cool the mixture to −78° C. Slowly add n-butyl lithium (1.40 equiv; 5.70 mmol; 3.56 mL) (1.6M Aldrich), and stir at −78° C. for 30 min, then add a THF (10 mL) solution of N-t-butoxycarbonyl-4-piperidone (1.20 equiv; 4.89 mmol; 973.43 mg) dropwise over 10 min. After 20 min, warm the reaction to RT and stir 3 h. Partition between EA and water. Wash the organic layer with brine, NaCl aq (50/50) and dry over MgSO$_4$. Filter and concentrate. Purify the residue by ISCO chromatography over a Biotage 40M column eluting with 100% DCM to 10% MeOH/DCM to give 785 mg (41%) of the title compound as a white solid. ES(MS): (m/z)=467.0 (M+H).

Prepare the following intermediates in a manner similar to that described in preparation 70:

| Preparation | Compound Name | MS (ES): (m/z) (M + H) |
|---|---|---|
| 71 | 4-[4-(3-Chloro-4-fluoro-phenyl)-1-(2-pyrrolidin-1-yl-ethyl)-1H-imidazol-2-yl]-4-hydroxy-piperidine-1-carboxylic acid tert-butyl ester | 493 |
| 72 | 4-(4-(4-Fluoro-3-(trifluoromethyl)phenyl)-1-(2-(pyrrolidin-1-yl)ethyl)-1H-imidazol-2-yl)-4-hydroxypiperidine-1-carboxylic acid tert-butyl ester | 527 |
| 73 | 4-(1-(2-(Dimethylamino)ethyl)-4-(4-fluoro-3-(trifluoromethyl)phenyl)-1H-imidazol-2-yl)-4-hydroxypiperidine-1-carboxylic acid tert-butyl ester | 501 |

Preparation 74

4-[4-(3-Chloro-4-fluoro-phenyl)-1-(2-dimethylamino-ethyl)-1H-imidazol-2-yl]-piperidin-4-ol dihydrochloride Dissolve 4-[4-(3-chloro-4-fluoro-phenyl)-1-(2-dimethylamino-ethyl)-1H-imidazol-2-yl]-4-hydroxy-piperidine-1-carboxylic acid tert-butyl ester (1.00 equiv; 1.68 mmol; 785.00 mg) in 5 mL DCM and slowly add hydrogen chloride (24.00 mmol; 6.00 mL of 4M in dioxane) at RT. After 5 min, the solution becomes cloudy then an oily white solid comes out of solution. Add 2 mL methanol to get the solid back in solution. At 30 min, HPLC shows 25% starting material. Add 1 mL additional HCl solution. After total of 2 h stirring at RT, concentrate under vacuum. Re-dissolve in DCM and evaporate under vacuum to a white solid; Dry the white solid in a vacuum oven at 45° C. to 900 mg of the title compound. ES(MS): (m/z)=367.0 (M+H).

Prepare the following intermediates in a manner similar to that described in preparation 74:

| Preparation | Compound Name | MS (ES): m/z (M + H) |
|---|---|---|
| 75 | 4-[4-(3-Chloro-4-fluoro-phenyl)-1-(2-pyrrolidin-1-yl-ethyl)-1H-imidazol-2-yl]-piperidin-4-ol dihydrochloride | 393.2 |
| 76 | 4-(4-(4-Fluoro-3-(trifluoromethyl)phenyl)-1-(2-(pyrrolidin-1-yl)ethyl)-1H-imidazol-2-yl)-piperidin-4-ol dihydrochloride | 427 |
| 77 | 4-(1-(2-(Dimethylamino)ethyl)-4-(4-fluoro-3-(trifluoromethyl)phenyl)-1H-imidazol-2-yl)-piperidin-4-ol dihydrochloride | 401 |

Preparation 78

2-(4-(4-Chlorophenyl)-2-(piperidin-4-yl)-1H-imidazol-1-yl)-N,N-dimethylethanamine tris hydrochloride

A. 4-(1-(2-(Tetrahydro-2H-pyran-2-yloxy)ethyl)-1H-imidazol-2-yl)piperidine-1-carboxylic acid tert-butyl ester Add 4-(1H-imidazol-2-yl)-piperidine-1-carboxylic acid tert-butyl ester (40 g; 0.16 mol; 1.0 equiv), powdered KOH (35.6 g; 0.64 mol; 4.0 equiv), 2-(2-bromo-ethoxy)-tetrahydropyran (66.2 g; 0.32 mol; 2.0 equiv) to DMSO (250 mL) and stir at RT for 2 h. Quench the reaction with water and extract with EA. Evaporate the organic layer to give the title compound (58 g; 97%).

B. 4-(4,5-Dibromo-1-(2-(tetrahydro-2H-pyran-2-yloxy)ethyl)-1H-imidazol-2-yl)piperidine-1-carboxylic acid tert-butyl ester Add 4-{1-[2-(tetrahydro-pyran-2-yloxy)-ethyl]-1H-imidazol-2-yl}-piperidine-1-carboxylic acid tert-butyl ester (58.2 g; 0.15 mol; 1.0 equiv) in DCM (500 mL) and cool to −10° C. Add N-bromosuccinimide (54.6 g; 0.31 mol; 2.0 equiv) and allow the reaction to come to RT. Quench the reaction with water and extract with DCM. Evaporate the organic layer to give the title compound (78.2 g; 95%).

C. 4-(4-Bromo-1-(2-(tetrahydro-2H-pyran-2-yloxy)ethyl)-1H-imidazol-2-yl)piperidine-1-carboxylic acid tert-butyl ester Add 4-{4,5-dibromo-1-[2-(tetrahydro-pyran-2-yloxy)-ethyl]-1H-imidazol-2-yl}-piperidine-1-carboxylic acid tert-butyl ester (39.0 g; 0.073 mol; 1.0 equiv) to THF (600 mL) and cool to −78° C. under an argon atmosphere. Add n-BuLi solution (1.6 M in cyclohexane) (53.7 mL; 0.087 mol; 1.2 equiv) drop-wise in 1 h and allow to come to −30° C. in 2 h. Quench the reaction with saturated ammonium chloride solution and extract with EA. Evaporate the organic layer and purify the residue with silica gel chromatography to give the title compound (13.2 g; 39%).

D. 4-(4-Bromo-1-(2-hydroxyethyl)-1H-imidazol-2-yl)piperidine-1-carboxylic acid tert-butyl ester Add 4-{4-bromo-1-[2-(tetrahydro-pyran-2-yloxy)-ethyl]-1H-imidazol-2-yl}-piperidine-1-carboxylic acid tert-butyl ester (13.2 g; 0.029 mol; 1.0 equiv), p-toluene sulphonic acid (6.5 g; 0.034 mol; 1.2 equiv) to methanol (200 mL) and stir at RT for 30 min. Concentrate and partition between saturated NaHCO$_3$ aqueous and EA. Evaporate the organic layer to give the title compound (10.0 g; 93%).

E. 4-(4-Bromo-1-(2-(methylsulfonyloxy)ethyl)-1H-imidazol-2-yl)piperidine-1-carboxylic acid tert-butyl ester Add 4-[4-bromo-1-(2-hydroxy-ethyl)-1H-imidazol-2-yl]-piperidine-1-carboxylic acid tert-butyl ester (10.0 g; 0.027 mol; 1.0 equiv), TEA (11.6 mL; 0.080 mol; 3.0 equiv) to DCM (150 mL) and cool to 0° C. Add drop-wise mesyl chloride (2.6 mL; 0.032 mol; 1.2 equiv) and stir for 30 min. Quench the reaction with saturated NaHCO$_3$ aqueous and extract with DCM. Evaporate the organic layer to give the title compound (10.2 g; 84%).

F. 4-(4-Bromo-1-(2-(dimethylamino)ethyl)-1H-imidazol-2-yl)piperidine-1-carboxylic acid tert-butyl ester Add 4-[4-bromo-1-(2-methanesulfonyloxy-ethyl)-1H-imidazol-2-yl]-piperidine-1-carboxylic acid tert-butyl ester (10.2 g; 0.023 mol; 1.0 equiv), dimethyl amine (40% aqueous solution, 22 mL; 0.18 mol; 8.0 equiv) in ACN (100 mL) and stir at 100° C. for 3 h. Concentrate, quench the reaction with saturated NaHCO$_3$ solution and extract with EA. Concentrate the organic layer; purify over a silica gel column with EA/hexane to give the title compound (7.5 g; 83.33%).

G. 4-(4-(4-Chlorophenyl)-1-(2-(dimethylamino)ethyl)-1H-imidazol-2-yl)piperidine-1-carboxylic acid tert-butyl ester Add 4-[4-bromo-1-(2-dimethylamino-ethyl)-1H-imidazol-2-yl]-piperidine-1-carboxylic acid tert-butyl ester (1.0 g; 0.0024 mol; 1.0 equiv), 4-chloro phenyl boronic acid (0.58 g; 0.0037 mol; 1.5 equiv), 3M Na$_2$CO$_3$ solution (0.79 g; 0.0074 mol; 3.0 equiv) to ethanol (5 mL) and toluene (5 mL) and degas the reaction with argon. Add Pd(PPh$_3$)$_4$ (0.29 g; 0.00024 mol; 0.1 equiv) and microwave at 110° C. for 20 min. Add EA and filter through a Celite® bed. Add saturated NaHCO$_3$ aqueous and extract with EA. Evaporate the organic layer, and purify the residue over a silica gel column with methanol in DCM to give the title compound (0.8 g; crude).

H. 2-(4-(4-Chlorophenyl)-2-(piperidin-4-yl)-1H-imidazol-1-yl)-N,N-dimethylethanamine tris hydrochloride Add 4M HCl in 1,4-dioxane (2 mL) to 4-[4-(4-chlorophenyl)-1-(2-dimethylamino-ethyl)-1H-imidazol-2-yl]-piperidine-1-carboxylic acid tert-butyl ester (0.8 g; 0.0018 mol; 1.0 equiv), in DCM and stir at RT for 6 h. Concentrate the reaction, crystallize from diethyl ether and filter to get the title compound (0.6 g; 74.07%). MS (ES+): m/z=333 (M+H)

Prepare the following intermediates in a manner similar to that described in the preparation of 2-(4-(4-chlorophenyl)-2-(piperidin-4-yl)-1H-imidazol-1-yl)-N,N-dimethylethanamine tris hydrochloride A. through to H.:

| Preparation | Compound Name | MS (ES+): m/z |
|---|---|---|
| 79 | 2-(4-(3-Chlorophenyl)-2-(piperidin-4-yl)-1H-imidazol-1-yl)-N,N-dimethylethanamine tris hydrochloride | 333 (M + H) |
| 80 | N,N-Dimethyl-2-(2-(piperidin-4-yl)-4-(3-(trifluoromethyl)phenyl)-1H-imidazol-1-yl)ethanamine tris hydrochloride | 367 (M + H) |
| 81 | 3-(1-(2-(Dimethylamino)ethyl)-2-(piperidin-4-yl)-1H-imidazol-4-yl)benzonitrile tris hydrochloride | 324 |
| 82 | 2-(4-(4-Fluorophenyl)-2-(piperidin-4-yl)-1H-imidazol-1-yl)-N,N-dimethylethanamine dihydrochloride | 317 |

Preparation 83

[4-(3-Chloro-4-fluoro-phenyl)-2-piperidin-4-yl-imidazol-1-yl]-acetonitrile bis trifluoroacetate Dissolve 4-[4-(3-chloro-4-fluoro-phenyl)-1-cyanomethyl-1H-imidazol-2-yl]-piperidine-1-carboxylic acid tert-butyl ester (399 mg; 0.95 mmol) in TFA (10 mL), stir 15 min and evaporate to provide the title compound (607 mg; 110%). MS (ES): m/z=319 (M+H).

Preparation 84

{2-[4-(3-Chloro-4-fluoro-phenyl)-2-piperidin-4-yl-imidazol-1-yl]-ethyl}-dimethyl-amine di hydrochloride Dissolve 4-(4-(3-chloro-4-fluorophenyl)-1-(2-(dimethylamino)ethyl)-1H-imidazol-2-yl)piperidine-1-carboxylic acid tert-butyl ester (194 mg; 0.43 mmol) in DCM (5 mL) and methanol (3 mL) and add 4 M hydrogen chloride in dioxane (5 mL; 20 mmol). Stir 30 min and evaporate; add DCM/MeOH and evaporate under vacuum to provide the title compound (245 mg) as a white solid. MS (ES): m/z=351 (M+H).

Prepare the following intermediates in a manner similar to that described in preparation 84:

| Preparation | Compound Name | MS (ES): m/z (M + H) |
|---|---|---|
| 85 | {2-[4-(4-Fluoro-3-trifluoromethyl-phenyl)-2-piperidin-4-yl-imidazol-1-yl]-ethyl}-dimethyl-amine dihydrochloride | 385 |
| 86 | 4-[4-(3-Chloro-4-fluoro-phenyl)-1-(2-pyrrolidin-1-yl-ethyl)-1H-imidazol-2-yl]-piperidine dihydrochloride | 376 |
| 87 | 4-[4-(4-Fluoro-3-trifluoromethyl-phenyl)-1-(2-pyrrolidin-1-yl-ethyl)-1H-imidazol-2-yl]-piperidine dihydrochloride | 411 |
| 88 | {2-[4-(4-Fluoro-3-trifluoromethyl-phenyl)-2-piperidin-4-yl-imidazol-1-yl]-1,1-dimethyl-ethyl}-dimethyl-amine tris hydrochloride | 413 |

-continued

| Preparation | Compound Name | MS (ES): m/z (M + H) |
|---|---|---|
| 89 | 4-(4-(3,4-Difluorophenyl)-1-(2-(pyrrolidin-1-yl)ethyl)-1H-imidazol-2-yl)piperidine tris hydrochloride | 361 |
| 90 | Benzyl 2-(4-(4-fluoro-3-(trifluoromethyl)phenyl)-2-(piperidin-4-yl)-1H-imidazol-1-yl)ethylcarbamate hydrochloride | 491 |
| 91 | {2-[4-(3-Chloro-4-fluoro-phenyl)-2-piperidin-4-yl-imidazol-1-yl]-ethyl}-methyl-carbamic acid benzyl ester tris hydrochloride | 471 |
| 92 | {2-[4-(3,4-Difluoro-phenyl)-2-piperidin-4-yl-imidazol-1-yl]-ethyl}-methyl-carbamic acid benzyl ester tris hydrochloride | 455 |
| 93 | (S)-2-[4-(3-Chloro-4-fluoro-phenyl)-2-piperidin-4-yl-imidazol-1-ylmethyl]-pyrrolidine-1-carboxylic acid benzyl ester bis hydrochloride | 497 |
| 94 | (R)-2-[4-(3-Chloro-4-fluoro-phenyl)-2-piperidin-4-yl-imidazol-1-ylmethyl]-pyrrolidine-1-carboxylic acid benzyl ester tris hydrochloride | 497 |
| 95 | 2-[4-(4-Fluoro-3-trifluoromethyl-phenyl)-2-piperidin-4-yl-imidazol-1-ylmethyl]-pyrrolidine-1-carboxylic acid benzyl ester dihydrochloride | 531 |
| 96 | 2-((4-(3,4-Difluorophenyl)-2-(piperidin-4-yl)-1H-imidazol-1-yl)methyl)pyrrolidine-1-carboxylic acid benzyl ester dihydrochloride | |
| 97 | {2-[4-(4-Fluoro-3-trifluoromethyl-phenyl)-2-piperidin-4-yl-imidazol-1-yl]-ethyl}-methyl-carbamic acid benzyl ester dihydrochloride | 505 |
| 98 | ((R)-1-{2-[4-(4-Fluoro-3-trifluoromethyl-phenyl)-2-piperidin-4-yl-imidazol-1-yl]-ethyl}-pyrrolidin-2-yl)-methanol tris hydrochloride | 441 |
| 99 | {2-[4-(4-Fluoro-3-trifluoromethyl-phenyl)-2-piperidin-4-yl-imidazol-1-yl]-ethyl}-isopropyl-methyl-amine tris hydrochloride | 413 |
| 100 | {2-[4-(3-Chloro-4-fluoro-phenyl)-2-piperidin-4-yl-imidazol-1-yl]-ethyl}-isopropyl-methyl-amine tris hydrochloride | 379 |
| 101 | tert-Butyl-{2-[4-(4-fluoro-3-trifluoromethyl-phenyl)-2-piperidin-4-yl-imidazol-1-yl]-ethyl}-amine tris hydrochloride | 413 |
| 102 | tert-Butyl-{2-[4-(3-chloro-4-fluoro-phenyl)-2-piperidin-4-yl-imidazol-1-yl]-ethyl}-amine tris hydrochloride | 379 |
| 103 | {2-[4-(3-Chloro-4-fluoro-phenyl)-2-piperidin-4-yl-imidazol-1-yl]-ethyl}-ethyl-isopropyl-amine tris hydrochloride | 393 |
| 104 | Dimethyl-[2-(4-phenyl-2-piperidin-4-yl-imidazol-1-yl)-ethyl]-amine dihydrochloride | 299 |
| 105 | 2-({2-[4-(3,4-Difluoro-phenyl)-2-piperidin-4-yl-imidazol-1-yl]-ethyl}-methyl-amino)-ethanol tris hydrochloride | 365 |
| 106 | 2-(4-(3,4-Difluorophenyl)-2-(piperidin-4-yl)-1H-imidazol-1-yl)-N,N-dimethylethanamine dihydrochloride | 335 |
| 107 | 1-(2-(4-(3,4-Difluorophenyl)-2-(piperidin-4-yl)-1H-imidazol-1-yl)ethyl)pyrrolidin-3-ol tris hydrochloride | 377 |
| 108 | 1-(2-(4-(3,4-Difluorophenyl)-2-(piperidin-4-yl)-1H-imidazol-1-yl)ethyl)azetidin-3-ol tris hydrochloride | 363 |

Preparation 108a (R)-Benzyl 2-((4-(4-fluoro-3-(trifluoromethyl)phenyl)-2-(piperidin-4-yl)-1H-imidazol-1-yl)methyl)piperidine-1-carboxylate trihydrochloride

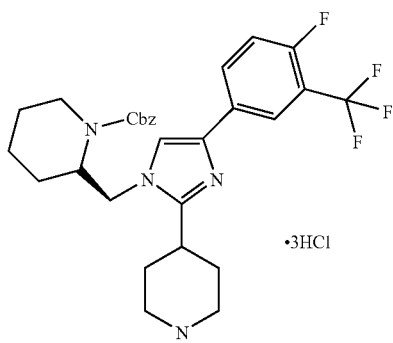

Dissolve (R)-benzyl 2-((2-(1-(tert-butoxycarbonyl)piperidin-4-yl)-4-(4-fluoro-3-(trifluoromethyl)phenyl)-1H-imidazol-1-yl)methyl)piperidine-1-carboxylate (2.6 g, 0.004 mol, 1.0 eq) in DCM (15 mL). Cool the reaction mass to 0° C. and add HCl (4.0 M in dioxane, 5 mL, 0.020 mol) drop-wise. Allow the reaction to warm up to RT and stir for 16 h. After completion, concentrate the reaction and co-evaporate with methanol (5×20 mL) under high vacuum to get 2.2 g (83.6%) of the title compound. (ES+): m/z=545 (M+H).

Prepare the following intermediate in a manner similar to that described in preparation 108a:

| Preparation | Compound Name | MS (ES): m/z (M + H) |
|---|---|---|
| 108b | (S)-Benzyl 2-((4-(4-fluoro-3-(trifluoromethyl)phenyl)-2-(piperidin-4-yl)- | 545 |

| Preparation | Compound Name | MS (ES): m/z (M + H) |
|---|---|---|
| | 1H-imidazol-1-yl)methyl)piperidine-1-carboxylate trihydrochloride | |

Preparation 108c (R)-2-((4-(3-(Difluoromethyl)-4-fluorophenyl)-2-(piperidin-4-yl)-1H-imidazol-1-yl)methyl)-1-methylpiperidine

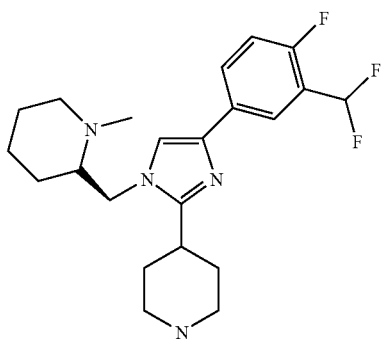

To a suspension of Lithium aluminium hydride (0.638 g, 0.0168 mol, 5.0 eq) in 20 mL THF at 0° C., add (R)-benzyl-2-((4-(4-fluoro-3-(trifluoromethyl)phenyl)-2-(piperidin-4-yl)-1H-imidazol-1-yl)methyl)piperidine-1-carboxylate in small portions (2.2 g, 0.0033 mol, 1.0 eq). Stir the reaction at RT for 4 hours. After completion, cool the reaction and quench with ice cold water followed by 10% NaOH solution and stir at RT and filter the resulting suspension through Celite®, wash the solid cake with EA. Dry the filtrate over anhydrous sodium sulfate and concentrate under reduced pressure to get 1.6 g of the title compound. (ES+): m/z 407 (M+H).

Preparation 109

4-Chloro-5-(thiazol-2-ylmethylene)-5H-pyrrolo[2,3-d]pyrimidin-6(7H)-one

Combine 4-chloro-5,7-dihydro-pyrrolo[2,3-d]pyrimidin-6-one (0.3 g; 0.0017 mol), thiazole-2-carbaldehyde (0.23 mL, 0.0026 mol) in methanol (1.5 mL). Add drop-wise pyrrolidine (0.073 mL; 0.0008 mol). Stir at RT for 15 min. Filter the solids to give the title compound (0.35 g; 76.08%).

Prepare the following intermediates in a manner similar to that described in preparation 109:

| Preparation | Compound Name | MS (ES+): m/z |
|---|---|---|
| 110 | 4-Chloro-5-(pyridin-4-ylmethylene)-5H-pyrrolo[2,3-d]pyrimidin-6(7H)-one | 259 |
| 111 | 4-Chloro-5-((2-methylthiazol-4-yl)methylene)-5H-pyrrolo[2,3-d]pyrimidin-6(7H)-one | 279 (M + 1) |
| 112 | 5-Benzylidene-4-chloro-5H-pyrrolo[2,3-d]pyrimidin-6(7H)-one | 258 (M + 1) |
| 113 | 5-((1H-Imidazol-5-yl)methylene)-4-chloro-5H-pyrrolo[2,3-d]pyrimidin-6(7H)-one | 248 (M + 1) |
| 114 | 5-((1H-Imidazol-2-yl)methylene)-4-chloro-5H-pyrrolo[2,3-d]pyrimidin-6(7H)-one | 248 (M + 1) |
| 115 | 4-Chloro-5-(thiazol-5-ylmethylene)-5H-pyrrolo[2,3-d]pyrimidin-6(7H)-one | 265 (M + 1) |

Preparation 116

5-Benzylidene-4-(4-(4-(3-chloro-4-fluorophenyl)-1-(2-(dimethylamino)ethyl)-1H-imidazol-2-yl)piperidin-1-yl)-5H-pyrrolo[2,3-d]pyrimidin-6(7H)-one Combine {2-[4-(3-chloro-4-fluoro-phenyl)-2-piperidin-4-yl-imidazol-1-yl]-ethyl}-dimethyl-amine tris hydrochloride (0.5 g; 0.0013 mol; 1.0 equiv); 5-benzylidene-4-chloro-5H-pyrrolo[2,3-d]pyrimidin-6(7H)-one (0.33 g; 0.0013 mol; 1.0 equiv); DIPEA (1.7 mL 0.0098 mol; 7.6 equiv); 2-propanol (10 mL) and microwave at 100° C. for 30 min. Cool and concentrate in vacuo. Dilute with saturated sodium bicarbonate solution and extract with DCM. Wash organic layer with water and brine and dry over anhydrous sodium sulfate. Concentrate the crude compound and purify by reverse phase HPLC to give the title compound as a mixture of E and Z isomers (0.09 g; 12.2%). MS (ES+): m/z=572 (M+H)

Prepare the following intermediates in a manner similar to that described in preparation 116:

| Preparation | Compound Name | MS (ES+): m/z |
|---|---|---|
| 117 | 5-Benzylidene-4-(4-(1-(2-(dimethylamino)ethyl)-4-(4-fluoro-3-(trifluoromethyl)phenyl)-1H-imidazol-2-yl)piperidin-1-yl)-5H-pyrrolo[2,3-d]pyrimidin-6(7H)-one | 607 |
| 118 | 5-Benzylidene-4-(4-(4-(3,4-difluorophenyl)-1-(2-(dimethylamino)ethyl)-1H-imidazol-2-yl)piperidin-1-yl)-5H-pyrrolo[2,3-d]pyrimidin-6(7H)-one | 557 |

Preparation 119

4-Chloro-5,5-dimethyl-5H-pyrrolo[2,3-d]pyrimidin-6(7H)-one

Method A: Add 4-chloro-5,7-dihydro-pyrrolo[2,3-d]pyrimidin-6-one (0.25 g; 0.0015 mol) to THF (7.5 mL). Cool to 0° C. and add portion-wise NaH (0.12 g; 0.0029 mol). Stir at 0° C. for 30 min. Add drop-wise methyl iodide (0.18 mL, 0.0029 mol). Stir at 0° C. for 30 min and then at RT for 1 h. Quench the reaction with saturated ammonium chloride aqueous and extract with EA. Evaporate the organic layer and purify the residue over a silica gel column using acetone:hexane as eluent to give the title compound (172 mg; 59.03%). MS (ES+): m/z=196 (M−H)

Method B: Add 4-chloro-5,7-dihydro-pyrrolo[2,3-d]pyrimidin-6-one (1 g; 0.0058 mol), potassium tert-butoxide (3.31 g; 0.029 mol), CuBrMe$_2$S (0.12 g; 0.00059 mol) to THF (20 mL). Cool to 0° C. and add drop-wise methyl iodide (0.99 mL; 0.016 mol). Bring the reaction to RT and stir for 10 min. Quench with saturated ammonium chloride aqueous and extract with EA. Evaporate the organic layer to give the title compound (0.91 g; 78.4%). MS (ES+): m/z=196 (M−H)

Preparation 120

4-Chloro-5-ethyl-5,7-dihydro-pyrrolo[2,3-d]pyrimidin-6-one

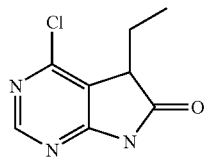

Add 4-chloro-5,7-dihydro-pyrrolo[2,3-d]pyrimidin-6-one (0.5 g; 0.0029 mol; 1.0 equiv) in THF (20 mL) and cool to −78° C. under argon atmosphere. Add drop-wise lithium hexamethyl-disilazide (5.89 mL, 0.0059 mol; 2.0 equiv; 1 M in THF). Stir at −78° C. for 30 min. Add drop-wise ethyl iodide (0.48 mL; 0.0059 mol; 2.0 equiv) and allow the reaction temperature to come to 0° C. slowly. Stir for 4 h. Quench with saturated ammonium chloride aqueous and extract with EA. Evaporate the organic layer to get the title compound (0.24 g; 41.38%).

Preparation 121

4-Chloro-5-methyl-5,7-dihydro-pyrrolo[2,3-d]pyrimidin-6-one

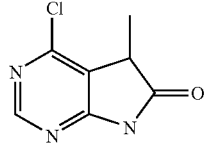

Add 4-chloro-5,7-dihydro-pyrrolo[2,3-d]pyrimidin-6-one (0.4 g; 0.0023 mol; 1.0 equiv) in THF (15 mL) and cool to −78° C. under an argon atmosphere. Add drop-wise lithium hexamethyldisilazide (4.7 mL; 0.0047 mol; 2.0 equiv; 1 M in THF). Stir the reaction at −78° C. for 30 min. Add drop-wise methyl iodide (0.29 mL; 0.0047 mol; 2.0 equiv), allow the reaction temperature to come to −20° C. slowly and stir at −20° C. for 2 h. Quench the reaction with saturated ammonium chloride aqueous and extract with EA. Evaporate the organic layer to give the title compound (0.24 g; 41.38%).

Preparation 122

4'-Chlorospiro[cyclopentane-1,5'-pyrrolo[2,3-d]pyrimidin]-6'(7'H)-one

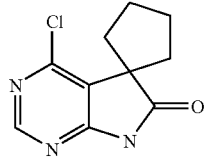

Add 4-chloro-5,7-dihydro-pyrrolo[2,3-d]pyrimidin-6-one (0.6 g; 0.0035 mol; 1.0 equiv) in anhydrous THF (20 mL) and cool the reaction to −78° C., under an inert atmosphere. Add drop-wise lithium hexamethyldisilazide (8.8 mL; 0.0088 mol; 2.5 equiv; 1M in THF). Stir at −78° C. for 30 min. Add drop-wise 1,4-diiodobutane (0.56 mL; 0.0042 mol; 1.2 equiv), allow the reaction temperature to reach 0° C. slowly, and stir for 2 h. Then allow the reaction to reach RT and stir for additional 1 h. Quench the reaction with saturated ammonium chloride solution and extract with EA. Wash the organic layer with water, brine, and dry over anhydrous sodium sulfate. Evaporate the organic layer and purify over a 10 g silica column with acetone (5%) in DCM. Pool fractions to give the title compound (0.34 g; 43.09%). H NMR (DMSO-d6): 11.68 (1H, s), 8.53 (1H, s), 2.0-2.1 (m, 2H), 1.91-1.99 (m, 6H).

Preparation 123

4,6-Dichloro-N-methylpyrimidin-5-amine

Add 5-amino-4,6-dichloropyrimidine (2 g; 0.012 mol) to THF (60 mL). Cool to 0° C. and add portion-wise NaH (0.53 g; 0.013 mol). Stir at 0° C. for 30 min. Add drop-wise methyl iodide (0.7 mL, 0.012 mol). Stir at 0° C. for 1 h and then RT for 30 min. Quench with saturated ammonium chloride aqueous and extract with EA. Evaporate the organic layer and purify the residue through a silica gel column using acetone and hexane as eluent to give the title compound (0.6 g; 27.64%).

Prepare the following intermediates as described in preparation 123:

| Preparation | Compound Name | Physical Data |
| --- | --- | --- |
| 124 | 4,6-Dichloro-N-ethylpyrimidin-5-amine | $^1$H NMR (400 MHz, DMSO): δ 8.25 (s, 1H), 5.51-5.48 (t, 1H, J = 6 Hz), 3.48-3.41 (m, 2H), 1.09-1.07 (t, 3H, J = 3.6 Hz) |
| 125 | 4,6-Dichloro-N-isopropylpyrimidin-5-amine | $^1$H NMR (400 MHz, CDCl3): δ 8.23 (s, 1H), 4.14 (m, 1H), 3.79 (m, 1H), 1.20 (d, 6H) |

Preparation 126

6-Chloro-$N^5$-methylpyrimidine-4,5-diamine

Combine 4,6-dichloro-N-methylpyrimidin-5-amine (0.6 g; 0.0034 mol), and liquid ammonia (6 mL) and stir at 80° C. for 4 h. Extract with EA and evaporate to give the title compound (0.41 g; 76.78%).

Prepare the following intermediates as described in preparation 126:

| Preparation | Compound Name | MS (ES+): m/z (M + 1) |
| --- | --- | --- |
| 127 | 6-chloro-$N^5$-ethylpyrimidine-4,5-diamine | 173 |
| 128 | 6-chloro-$N^5$-isopropylpyrimidine-4,5-diamine | 187 |

Preparation 129

6-Chloro-7-methyl-7,9-dihydro-purin-8-one

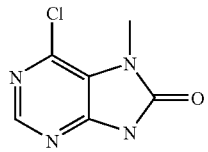

Add 6-chloro-N⁵-methyl-pyrimidine-4,5-diamine (0.41 g, 0.0025 mol) to THF (12.3 mL). Cool to 0° C., add TEA (0.51 g; 0.005 mol), triphosgene (0.92 g; 0.0031 mol) and stir at RT for 1 h. Quench with water and extract with EA. Evaporate the organic layer to give the title compound (0.2 g; 42%).

Prepare the following intermediate in a manner similar to that described in preparation 129:

| Preparation | Compound Name | Physical Data |
|---|---|---|
| 130 | 6-Chloro-7-ethyl-7H-purin-8(9H)-one | ¹H NMR (400 MHz, DMSO): δ 12.51 (s, 1H), 8.39 (s, 1H), 4.03-3.97 (q, 2H, J = 7.2 Hz), 1.27-1.23 (t, 3H, J = 7.2 Hz) |

Prepare the following intermediate in a manner similar to that described preparation 131:

| Preparation | Compound Name | MS (ES+): m/z (M + 1) |
|---|---|---|
| 132 | 6-Chloro-7-isopropyl-7H-purin-8(9H)-one | 213 |

Preparation 133

(2-{4-(4-Fluoro-3-trifluoromethyl-phenyl)-2-[1-(6-oxo-6,7-dihydro-5H-pyrrolo[2,3-d]pyrimidin-4-yl)-piperidin-4-yl]-imidazol-1-yl}-ethyl)-methyl-carbamic acid benzyl ester Combine {2-[4-(4-fluoro-3-trifluoromethyl-phenyl)-2-piperidin-4-yl-imidazol-1-yl]-ethyl}-methyl-carbamic acid benzyl ester dihydrochloride (277 μmol; 160 mg); 4-chloro-5,7-dihydro-pyrrolo[2,3-d]pyrimidin-6-one (1.30 equiv; 360 μmol; 61.1 mg); DMF (3 mL); TEA (7 equiv; 1.94 mmol; 270 μL) and heat to 160° C. in microwave for 45 min. Evaporate, dissolve the residue in DCM, wash with saturated sodium bicarbonate and evaporate the organic layer. Purify the residue on 40 g silica gel with 3% MeOH/DCM to provide the title compound (138.2 mg; 0.22 mmol; 78%). MS (ES+): m/z=638 (M+H).

Prepare the following intermediates in a manner similar to that described in preparation 133:

| Preparation | Compound Name | MS (ES+): m/z (M + H) |
|---|---|---|
| 134 | (2-{4-(3-Chloro-4-fluoro-phenyl)-2-[1-(6-oxo-6,7-dihydro-5H-pyrrolo[2,3-d]pyrimidin-4-yl)-piperidin-4-yl]-imidazol-1-yl}-ethyl)-methyl-carbamic acid benzyl ester | 604 |
| 135 | (2-{4-(3,4-Difluoro-phenyl)-2-[1-(7-ethyl-8-oxo-8,9-dihydro-7H-purin-6-yl)-piperidin-4-yl]-imidazol-1-yl}-ethyl)-methyl-carbamic acid benzyl ester | 617 |
| 136 | (S)-(2-{4-(3-Chloro-4-fluoro-phenyl)-2-[1-(7-ethyl-8-oxo-8,9-dihydro-7H-purin-6-yl)-piperidin-4-yl]-imidazol-1-ylmethyl-pyrrolidine-1-carboxylic acid benzyl ester | 659 |
| 137 | (R)-(2-{4-(3-Chloro-4-fluoro-phenyl)-2-[1-(7-ethyl-8-oxo-8,9-dihydro-7H-purin-6-yl)-piperidin-4-yl]-imidazol-1-ylmethyl-pyrrolidine-1-carboxylic acid benzyl ester | 659 |
| 138 | 2-{4-(4-Fluoro-3-trifluoromethyl-phenyl)-2-[1-(6-oxo-6,7-dihydro-5H-pyrrolo[2,3-d]pyrimidin-4-yl)-piperidin-4-yl]-imidazol-1-ylmethyl}-pyrrolidine-1-carboxylic acid benzyl ester | 664 |
| 139 | 2-((4-(3,4-Difluorophenyl)-2-(1-(6-oxo-6,7-dihydro-5H-pyrrolo[2,3-d]pyrimidin-4-yl)piperidin-4-yl)-1H-imidazol-1-yl)methyl)pyrrolidine-1-carboxylic acid benzyl ester | |
| 140 | Benzyl 2-(4-(4-fluoro-3-(trifluoromethyl)phenyl)-2-(1-(6-oxo-6,7-dihydro-5H-pyrrolo[2,3-d]pyrimidin-4-yl)piperidin-4-yl)-1H-imidazol-1-yl)ethylcarbamate | |

Preparation 131

6-Chloro-7,9-dihydro-purin-8-one

Combine 6-chloro-pyrimidine-4,5-diamine (7.46 mmol; 1.08 g); 1,1'-carbonyldiimidazole (2 equiv; 14.92 mmol; 2.42 g) and 1,4-dioxane (20 mL) and heat to reflux under nitrogen for 50 min. Evaporate the yellow solution to an oil. Add DCM (80 mL), let sit 1 h, filter and dry in vacuum oven at 45° C. to provide the title compound (1.22 g; 7.15 mmol; 96%) MS (ES+): m/z=169 (M−H).

Preparation 141

5,5-Dibromo-4-chloro-5,7-dihydro-pyrrolo[2,3-d]pyrimidin-6-one

Add pyridinium bromide perbromide (3 equiv; 70.5 g; 266 mmol) to a solution of 4-chloro-7H-pyrrolo[2,3-d]pyrimidine (66.1 mmol; 10.16 g) in t-butyl alcohol (400 mL) at 40° C. Stir 4 h, then add pyridinium bromide perbromide (1 equiv; 23.5 g) and stir 18 h. Partition 1 L EA/1.5 L water, extract three times with EA, combine organics and wash with water (3×200 mL), two times with brine, dry over MgSO₄, filter and evaporate. Suspend in hot DCM (200 mL), cool, filter and dry under vacuum to provide the title compound (13.00 g; 39.7 mmol, 60%) as a tan solid. MS (ES+): m/z=328 (M+H).

Preparation 142

4-Chloro-5,7-dihydro-pyrrolo[2,3-d]pyrimidin-6-one

Add zinc (2 equiv; 12.12 mmol; 792 mg) to a suspension of 5,5-dibromo-4-chloro-5,7-dihydro-pyrrolo[2,3-d]pyrimidin-6-one (6.06 mmol; 1.98 g) in THF (20 mL) and add saturated ammonium chloride aqueous (3 mL) at 20° C. (exothermic). Stir 20 min then filter through Celite®, rinse with THF, wash the organic phase twice with saturated ammonium chloride. Extract combined aqueous layers four times with 100 mL 1:1 THF:EA, wash the combined organic phases with saturated ammonium chloride, dry over MgSO$_4$, filter through silica gel plug, rinse with 1 L 5% MeOH/DCM and evaporate filtrates. Suspend crude solid in refluxing mixtures of DCM/EA and load onto 330 g of dry silica gel. Chromatograph with 0 to 2% MeOH/DCM to provide the title compound 3.89 g (22.93 mmol; 59%). MS (ES+): m/z=168 (M−H).

Preparation 143

(R)-3-Amino-piperidine-1-carboxylic acid benzyl ester

Add 4M HCl in dioxane (100 mL) to a solution of (R)-3-tert-butoxycarbonylamino-piperidine-1-carboxylic acid benzyl ester (71.65 mmol; 23.96 g) in DCM (100 mL) and MeOH (10 mL). Stir 60 min and evaporate. Partition solid between DCM and saturated sodium bicarbonate aqueous, extract three times with DCM, Wash extracts with brine, dry over MgSO$_4$, filter through Celite® and evaporate to give the title compound 17.39 g (74.22 mmol; 104%). MS (ES+): m/z=235 (M+H).

Preparation 144

(R)-3-[2-(4-Fluoro-3-trifluoromethyl-phenyl)-2-oxo-ethylamino]-piperidine-1-carboxylic acid benzyl ester hydrochloride Combine 2-bromo-1-(4-fluoro-3-trifluoromethyl-phenyl)-ethanone (1.00 equiv; 22.57 mmol; 6.43 g) in 15 mL DMF dropwise to a solution of (R)-3-amino-piperidine-1-carboxylic acid benzyl ester (1 equiv; 22.57 mmol; 5.29 g) and TEA (1 equiv; 22.57 mmol; 3.15 mL) in DMF (30 mL). Stir 10 min. Dilute with EA, wash 3× with brine, dry over MgSO$_4$, filter, add 1 equiv 1M HCl in ether and evaporate to give 10.56 g orange residue. Dissolve in IPA (100 mL), cool in ice bath, filter the solids, rinse with diethyl ether, dry in a vacuum oven at 40° C. to provide the title compound (3.49 g; 7.35 mmol; 33%). MS (ES+): m/z=439 (M+H).

Preparation 145

4-{((R)-1-Benzyloxycarbonyl-piperidin-3-yl)-[2-(4-fluoro-3-trifluoromethyl-phenyl)-2-oxo-ethyl]-carbamoyl}-piperidine-1-carboxylic acid tert-butyl ester Add thionyl chloride (1.2 equiv; 10.5 mmol; 765 µL) dropwise over 3 min at 20° C. to a solution of piperidine-1,4-dicarboxylic acid mono-tert-butyl ester (1.00 equiv; 8.75 mmol; 2.03 g) and pyridine (5 equiv; 43.74 mmol; 3.54 mL) in DCM (60 mL). Stir 90 min. Add (R)-3-[2-(4-fluoro-3-trifluoromethyl-phenyl)-2-oxo-ethylamino]-piperidine-1-carboxylic acid benzyl ester hydrochloride (0.80 equiv; 7.00 mmol; 3.32 g) followed by TEA (3.5 equiv; 30.62 mmol; 4.3 mL) dropwise over 3 min and stir 18 h. Wash the organic phase 3× with 1N HCl, water, brine, dry over MgSO$_4$, filter and evaporate. Purify the residue on 150 g silica gel with 20-50% EA/DCM to provide the title compound (2.86 g; 4.41 mmol; 50%). MS (ES+): m/z=672 (M+Na).

Preparation 146

4-[1-((R)-1-Benzyloxycarbonyl-piperdin-3-yl)-4-(4-fluoro-3-trifluoromethyl-phenyl)-1H-imidazol-2-yl]-piperidine-1-carboxylic acid tert-butyl ester Heat a solution of 4-{((R)-1-benzyloxycarbonyl-piperidin-3-yl)-[2-(4-fluoro-3-trifluoromethyl-phenyl)-2-oxo-ethyl]-carbamoyl}-piperidine-1-carboxylic acid tert-butyl ester (4.40 mmol; 2.86 g) in DMF (2.5 mL) and ammonium acetate saturated in acetic acid (15 mL) at 90° C. for 8 h. Dilute with EA, wash the organic phase 3× with water, saturated sodium bicarbonate, brine, dry over MgSO$_4$ and filter. Purify the residue on 80 g silica gel with 5-20% EA/DCM to provide the title compound (2.08 g; 3.30 mmol; 75%). MS (ES+): m/z=631 (M+H).

Preparation 147

4-[(R)-4-(4-Fluoro-3-trifluoromethyl-phenyl)-1-piperidin-3-yl-1H-imidazol-2-yl]-piperidine-1-carboxylic acid tert-butyl ester Hydrogenate a solution of 4-[1-((R)-1-benzyloxycarbonyl-piperdin-3-yl)-4-(4-fluoro-3-trifluoromethyl-phenyl)-1H-imidazol-2-yl]-piperidine-1-carboxylic acid tert-butyl ester (1.71 mmol; 1.08 g) in methanol (20 mL) with 10% Palladium on carbon (100 mg) and 1 atmosphere of hydrogen gas for 60 min. Add Celite® and filter, rinse with DCM and evaporate to provide the title compound (834.3 mg; 1.68 mmol; 98%). MS (ES+): m/z=497 (M+H).

Preparation 148

4-[4-(4-Fluoro-3-trifluoromethyl-phenyl)-1-((R)-1-methyl-piperidin-3-yl)-1H-imidazol-2-yl]-piperidine-1-carboxylic acid tert-butyl ester Combine 4-[(R)-4-(4-fluoro-3-trifluoromethyl-phenyl)-1-piperidin-3-yl-1H-imidazol-2-yl]-piperidine-1-carboxylic acid tert-butyl ester (1.49 mmol; 741 mg); formaldehyde (5 equiv; 7.46 mmol; 560 µL); sodium triacetoxyborohydride (2 equiv; 2.98 mmol; 632 mg) and THF (25 mL) and stir at 20° C. for 20 min. Dilute with EA, wash the organic phase 2× with saturated sodium bicarbonate, brine, dry over MgSO$_4$, filter and evaporate to provide the title compound (790.3 mg; 1.55 mmol; 104%). MS (ES+): m/z=511 (M+H).

Preparation 149

(R)-3-[4-(4-Fluoro-3-trifluoromethyl-phenyl)-2-piperidin-4-yl-imidazol-1-yl]-1-methyl-piperidine Add 4M HCl in dioxane (6 mL) to a solution of 4-[4-(4-fluoro-3-trifluoromethyl-phenyl)-1-((R)-1-methyl-piperidin-3-yl)-1H-imidazol-2-yl]-piperidine-1-carboxylic acid tert-butyl ester (1.55 mmol; 790 mg) in methanol (2 mL) and DCM (5 mL) and stir 1 h. Evaporate to provide 847 mg tris HCl salt. Partition 712 mg tris HCl salt between DCM/saturated sodium bicarbonate, dry over MgSO$_4$, filter and evaporate to provide the title compound (529.6 mg; 1.29 mmol; 94%). MS (ES+): m/z=411 (M+H).

Prepare the following intermediate in a manner similar to that described in preparation 149:

| Preparation | Compound Name | MS (ES+): m/z (M + H) |
|---|---|---|
| 150 | (R)-Benzyl 3-(4-(4-fluoro-3-(trifluoromethyl)phenyl)-2-(piperidin-4-yl)-1H-imidazol-1-yl)piperidine-1-carboxylate | 531 |

Preparation 151

(R)-2-{4-(3-Chloro-4-fluoro-phenyl)-2-[1-(6-oxo-6, 7-dihydro-5H-pyrrolo[2,3-d]pyrimidin-4-yl)-piperidin-4-yl]-imidazol-1-ylmethyl}-pyrrolidine-1-carboxylic acid benzyl ester Combine potassium tert-butoxide (1.1 equiv; 321 µmol; 36.8 mg); IPrPd(acac)Cl (0.08 equiv; 23.4 µmol; 14.8 mg) and stir bar in 25 mL 3 neck flask and purge with nitrogen for 5 min. Add anhydrous DME (3 mL) followed by 4-chloro-5, 7-dihydro-pyrrolo[2,3-d]pyrimidin-6-one (1 equiv; 292 µmol; 50 mg); (R)-2-[4-(3-chloro-4-fluoro-phenyl)-2-piperidin-4-yl-imidazol-1-ylmethyl]-pyrrolidene-1-carboxylic acid benzyl ester tris hydrochloride (1.1 equiv; 321 µmol; 159.6 mg) and 0.5 mL 1,2-DME and heat to 80° C. for 18 h. Dilute with EA, wash the organic phase with water, saturated sodium bicarbonate, brine, dry over MgSO$_4$, filter and evaporate. Purify the residue on 40 g silica gel with 5% MeOH/DCM to provide the title compound (124.7 mg; 0.198 mmol; 68%). MS (ES+): m/z=630 (M+H).

Prepare the following intermediate in a manner similar to that described in preparation 151:

| Preparation | Compound Name | MS (ES+): m/z (M + 1) |
|---|---|---|
| 152 | (R)-Benzyl 3-(4-(4-fluoro-3-(trifluoromethyl)phenyl)-2-(1-(6-oxo-6,7-dihydro-5H-pyrrolo[2,3-d]pyrimidin-4-yl)piperidin-4-yl)-1H-imidazol-1-yl)piperidine-1-carboxylate | 664 |

Preparation 153

Methyl 2-(4,6-dihydroxypyrimidin-5-yl)acetate

Add triethyl ethane-1,1,2-tricarboxylate (74.75 g; 1.00 equiv; 303.54 mmol; 69.41 mL) to a solution of sodium methoxide (139.6 mL of 25% wt in MeOH, 4.35M) (131.2 g; 2.00 equiv; 607 mmol) in methanol (224.8 mL), then add formamidine hydrochloride (25.19 g, 1.01 equiv; 306.58 mmol) at RT. Stir the mixture overnight. Acidify with 37% HCl at 0° C.; filter the solids and dry in vacuo overnight to give the title compound (55.89 g; 99.99% yield) as a white solid. $^1$H NMR (300 MHz, DMSO): 8.03 (s, 1H), 3.55 (s, 3H), 3.24-3.15 (m, 2H).

Preparation 154

Methyl 2-(4,6-dichloropyrimidin-5-yl)acetate

Add a suspension of methyl 2-(4,6-dihydroxypyrimidin-5-yl)acetate (46.65 g; 1.00 equiv; 253.33 mmol) to phosphoryl chloride (235.41 mL; 10.00 equiv; 2.53 mol) and stir at reflux 3 h. Distill under vacuum to ⅓ of the original volume and pour the mixture into a 4° C. solution of aqueous potassium phosphate, dibasic (2M) (2.53 L; 20 equiv; 5.07 mol). Extract with EA, dry over MgSO$_4$, filter and concentrate in vacuo. Purify the crude by silica plug using DCM as eluent to give the title compound (30.32 g; 137.17 mmol; 54.15% yield) as a pale yellow solid. $^1$H NMR (300 MHz, DMSO): 8.89 (s, 1H), 4.03 (s, 2H), 3.69 (s, 3H).

Preparation 155

Methyl 2-(4-chloro-6-(4-methoxybenzylamino)pyrimidin-5-yl)acetate

To a solution of methyl 2-(4,6-dichloropyrimidin-5-yl)acetate (1.00 equiv; 65.10 mmol; 14.39 g) in DMF (0.5 M; 1.68 mol; 130.20 mL), add 4-methoxybenzylamine (1.10 equiv; 71.61 mmol; 9.36 mL) and DIPEA (1.20 equiv; 78.12 mmol; 13.62 mL) and stir the mixture at 60° C. for 1 h. Quench with ice-water, extract with EA, and wash the organic layer with 1N HCl, water and brine, dry over MgSO$_4$, filter and concentrate in vacuo to the title compound (54.98 mmol; 17.69 g; 84.45%) as a yellow solid and use without further purification. $^1$H NMR (300 MHz, DMSO): 8.20 (s, 1H), 7.21-7.18 (m, 2H), 6.89-6.85 (m, 2H), 4.53 (d, J=5.8 Hz, 2H), 3.76 (s, 2H), 3.71 (s, 3H).

Prepare the following intermediate in a manner similar to that described in preparation 155:

| Preparation | Compound Name | Physical Data |
|---|---|---|
| 156 | Methyl 2-(4-chloro-6-(2,4-dimethoxybenzylamino)pyrimidin-5-yl)acetate | $^1$H NMR (400 MHz, CDCl$_3$): 8.33 (s, 1H), 7.21 (d, J = 8.4 Hz, 1H), 6.46 (d, J = 2.0 Hz, 1H), 6.42 (d, J$_1$ = 8.4 Hz, J$_2$ = 2.0 Hz, 1H), 6.07 (bs, 1H), 4.62 (d, J = 6.0 Hz, 2H), 3.84 (s, 3H), 3.79 (s, 3H), 3.67 (s, 3H), 3.61 (s, 2H), |

Preparation 157

4-Chloro-7-(4-methoxybenzyl)-5H-pyrrolo[2,3-d]pyrimidin-6(7H)-one

Add a solution of methyl 2-(4-chloro-6-(4-methoxybenzylamino)pyrimidin-5-yl)acetate (16.21 g, 1.00 equiv; 50.38 mmol) to HCl (4M in dioxane) (126 mL; 10 equiv; 503.79 mmol) and water (4.54 mL; 5 equiv; 251.89 mmol) and stir at 100° C. for 2 h. Remove dioxane in vacuo and extract with EA. Wash the organic layer with saturated NaHCO$_3$, water, then brine. Dry over MgSO$_4$, filter and concentrate in vacuo. Purify the residue by ISCO 330 g using EA:hex 20 to 70% as eluent to obtain the title compound (11.15 g; 38.49 mmol;

76.39%) as a yellow solid. $^1$H NMR (300 MHz, DMSO): 8.65 (s, 1H), 7.29-7.26 (m, 2H), 6.89-6.85 (m, 2H), 4.79 (s, 2H), 3.80 (s, 2H), 3.71 (s, 3H).

Preparation 158

4-Chloro-7-(2,4-dimethoxybenzyl)-5H-pyrrolo[2,3-d]pyrimidin-6(7H)-one

Combine a solution of methyl 2-(4-chloro-6-(2,4-dimethoxybenzylamino)pyrimidin-5-yl)acetate (1.00 equiv; 2.23 mol; 783 g) in p-toluenesulfonic acid (0.5 equiv; 1.10 mol; 212 g) with Toluene (12 L) and stir at reflux. After 1 h, remove toluene in vacuo and extract with DCM. Wash the organic layer with saturated NaHCO$_{3(aq)}$ and brine, dry over Na$_2$SO$_4$, filter and concentrated in vacuo. Slurry the residue in methanol (2 L) and concentrate in vacuo to approximately 1 L. Cool the slurry to 10° C., filter, wash with cold methanol, and dry to obtain the title compound (1.65 mol; 527 g; 74.05%) as a yellow-orange solid. $^1$H NMR (400 MHz, CDCl$_3$): 8.59 (s, 1H), 7.13 (d, J=8.4 Hz, 1H), 6.43 (d, J=2.0 Hz, 1H), 6.40 (d, J=8.5 Hz, 1H), 4.92 (d, s, 2H), 3.79 (s, 3H), 3.77 (s, 3H), 3.60 (s, 2H).

Preparation 159

4-(1-(2-(Dimethylamino)ethyl)-4-(4-fluoro-3-(trifluoromethyl)phenyl)-1H-imidazol-2-yl)piperidine-1-carboxylic acid tert-butyl ester Combine a solution of 4-[4-(4-fluoro-3-trifluoromethyl-phenyl)-1H-imidazol-2-yl]-piperidine-1-carboxylic acid tert-butyl ester (25.00 g; 1.00 equiv; 60.47 mmol) in DMSO (200.00 mL; 2.82 mol) with KOH (powder) (9.98 g; 151.18 mmol) and heat the mixture to 45° C. To this solution, add 2-chloro-N,N-dimethylethanamine hydrochloride (10.45 g; 1.20 equiv; 72.57 mmol). Stir the mixture at 45° C. for 3 h. Pour the mixture into ice-water, stir at RT and extract with EA. Wash the organic layer with water (3×) and brine; dry over MgSO$_4$, filter and concentrate in vacuo to give the title compound (28.00 g; 57.79 mmol; 95.56%) as a yellow oil and use without further purification. $^1$H NMR (300 MHz, DMSO): 8.04-8.00 (m, 2H), 7.74 (s, 1H), 7.46 (t, J=9.9 Hz, 1H), 4.06-3.99 (m, 4H), 3.03-2.93 (m, 3H), 2.57 (t, J=6.3 Hz, 2H), 2.19 (s, 6H), 1.81-1.77 (m, 2H), 1.70-1.55 (m, 2H), 1.42 (s, 9H).

Preparation 160

2-(4-(4-Fluoro-3-(trifluoromethyl)phenyl)-2-(piperidin-4-yl)-1H-imidazol-1-yl)-N,N-dimethylethanamine dihydrochloride Combine a solution of 4-(1-(2-(dimethylamino)ethyl)-4-(4-fluoro-3-(trifluoromethyl)phenyl)-1H-imidazol-2-yl)piperidine-1-carboxylic acid tert-butyl ester (28.00 g; 1.00 equiv; 57.79 mmol) in DCM (280.00 mL; 4.37 mol) with a 4 M solution of hydrogen chloride in methanol (50.56 mL; 3.50 equiv; 202.25 mmol). Stir the green suspension at RT for 3 h. Evaporate the solvent, and add EA (100 mL) and evaporate again. Add EA (200 mL) and stir the suspension for 30 m. Filter on a glass fritted funnel to obtain the title compound (26.00 g; 56.85 mmol; 98.38% yield) as a green solid. m/z (M+H): 385.2

Preparation 161

4-(4-(1-(2-(Dimethylamino)ethyl)-4-(4-fluoro-3-(trifluoromethyl)phenyl)-1H-imidazol-2-yl)piperidin-1-yl)-7-(4-methoxybenzyl)-5H-pyrrolo[2,3-d]pyrimidin-6(7H)-one Add a solution of 4-chloro-7-(4-methoxybenzyl)-5H-pyrrolo[2,3-d]pyrimidin-6(7H)-one (18.11 g; 1.05 equiv; 62.52 mmol) in NMP (156.50 mL; 1.62 mol) at RT to 2-(4-(4-fluoro-3-(trifluoromethyl)phenyl)-2-(piperidin-4-yl)-1H-imidazol-1-yl)-N,N-dimethylethanamine dihydrochloride (31.30 g; 1.00 equiv; 59.54 mmol) and DIPEA (51.92 mL; 297.71 mmol) and stir overnight at 50° C. Quench the reaction with water (900 mL) and EA (200 mL) and adjust the pH of the mixture to 1-2 with H$_3$PO$_4$ [85% aqueous (aq.)]. Stir for 15 min and separate the phases. Extract the organic phase with a H$_3$PO$_4$ solution (15% aq. 3×100 mL). Wash the combined aqueous phases with EA/tert-butylmethyl ether (tBuOMe) (4/1) (3×150 mL). Adjust the pH of the aqueous phase to 9 with solid K$_2$CO$_3$ and extract with EA (3×15 mL). Wash the combined organic phases with brine, decolor with charcoal, and filter over Celite®. Combine the filtrates and evaporate. Crystallize the residue from EA/tBuOMe to obtain the title compound (17.00 g; 26.66 mmol; 44.77% yield) as pale rose solid. $^1$H NMR (300 MHz, CDCl$_3$): 8.36 (s, 1H), 7.91-7.83 (m, 2H), 7.43-7.40 (m, 2H), 7.17-7.11 (m, 2H), 6.86-6.81 (m, 2H), 4.87 (s, 2H), 4.56 (d, J=13.4 Hz, 2H), 4.13-4.07 (m, 2H), 3.77 (s, 3H), 3.63 (s, 2H), 3.40-3.36 (m, 2H), 3.21-3.05 (m, 3H), 2.74 (t, J=6.6 Hz, 2H), 2.40-2.35 (m, 6H), 2.09-1.99 (m, 2H).

Preparation 162

4-(4-(1-(2-(Dimethylamino)ethyl)-4-(4-fluoro-3-(trifluoromethyl)phenyl)-1H-imidazol-2-yl)piperidin-1-yl)-7-(2,4-dimethoxybenzyl)-5H-pyrrolo[2,3-d]pyrimidin-6 (7H)-one Combine a mixture of 4-chloro-7-(2,4-dimethoxybenzyl)-5H-pyrrolo[2,3-d]pyrimidin-6(7H)-one (1.10 equiv; 868.3 mmol; 277.63 g) in methanol (62.44 mol; 2.53 L) at RT, a solution of 2-(4-(4-fluoro-3-(trifluoromethyl)phenyl)-2-(piperidin-4-yl)-1H-imidazol-1-yl)-N,N-dimethylethanamine dihydrochloride (1.00 equiv; 789.35 mmol; 361.0 g) and TEA (9077 mmol; 1265 mL) in methanol (62.44 mol; 2.53 L) and stir the mixture overnight at 55-60° C. Partition the reaction mixture between water (10 L) and EA (10 L). Extract the organic layer with 2 N HCl (5 L). Separate and extract the aqueous layer with EA (5 L). An oil separates in the aqueous layer. Decant the aqueous liquid and hold the oil for recovery of product. Stir the decanted aqueous layer with EA (5 L) and adjust the pH of the mixture to 10-11 with 2 N NaOH. Separate the organic layer, wash with brine, and dry over Na$_2$SO$_4$. Filter and evaporate the solvent to give the title compound (473.3 mmol; 316.0 g; 60%).

Dissolve the decanted oil in water (15 L) and wash with EA (5 L). Stir the aqueous layer with EA (5 L) and adjust the pH of the mixture to 10-11 with 2 N NaOH. Separate the organic phase, wash with brine, and dry over Na$_2$SO$_4$. Filter, and evaporate the filtrate. Crystallize the residue EA; filter and wash with MTBE. Dry to obtain additional title compound (46.42 mmol; 31.0 g; 5.88%) as pale rose solid. $^1$H NMR (400 MHz, DMSO): 8.18 (s, 1H), 7.99-7.95 (m, 2H), 7.71 (s, 1H), 7.43-7.39 (m, 2H), 6.76 (d, J=7.1 Hz 1H), 6.54 (d, J=2 Hz 1H), 6.38-6.35 (m, 1H), 4.67 (s, 2H), 4.49 (d, J=13.1 Hz, 2H), 4.03 (t, J=6.52, 2H), 3.89 (s, 2H), 3.78 (s, 3H), 3.69 (s, 3H), 3.15-3.09 (m, 3H), 2.57 (t, J=6.6 Hz, 2H), 2.18 (s, 6H), 1.89-1.74 (m, 4H).

Preparation 162a (2S)-Benzyl 2-((2-(1-(5-ethyl-6-oxo-6,7-dihydro-5H-pyrrolo[2,3-d]pyrimidin-4-yl)piperidin-4-yl)-4-(4-fluoro-3-(trifluoromethyl)phenyl)-1H-imidazol-1-yl)methyl)piperidine-1-carboxylate

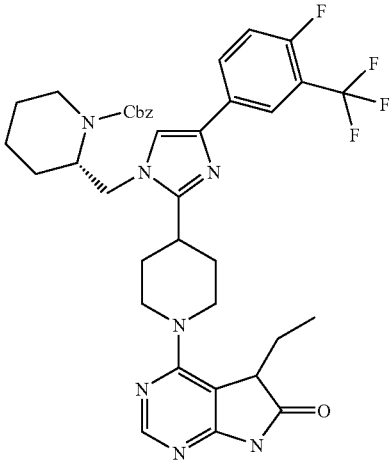

Combine (S)-benzyl 2-((4-(4-fluoro-3-(trifluoromethyl)phenyl)-2-(piperidin-4-yl)-1H-imidazol-1-yl)methyl)piperidine-1-carboxylate trihydrochloride (1.1 g, 0.00168 mol, 1.0 eq); 4-chloro-5-ethyl-5,7-dihydro-pyrrolo[2,3d]pyrimidin-6-one (0.4 g, 0.002 mol, 1.2 eq); DIPEA (2 mL, 0.011 mol, 7.0 eq) and 2-propanol (20 mL) in a pressure tube and heat at 120° C. overnight under sealed condition. Cool the reaction mass and dilute with water. Extract in EA and wash the organic layer with brine. Dry over anhydrous sodium sulfate and concentrate the crude compound. Purify on silica gel (100-200 mesh) column using 10% acetone-DCM as eluent. Pool the fractions containing the desired compound and concentrate under vacuum to the title compound. MS (ES+): m/z=706 (M+H).

Example 1

4-{4-[4-(4-Fluoro-3-trifluoromethyl-phenyl)-1-(2-methylamino-ethyl)-1H-imidazol-2-yl]-piperidin-1-yl}-5,7-dihydro-pyrrolo[2,3-d]pyrimidin-6-one tris hydrochloride

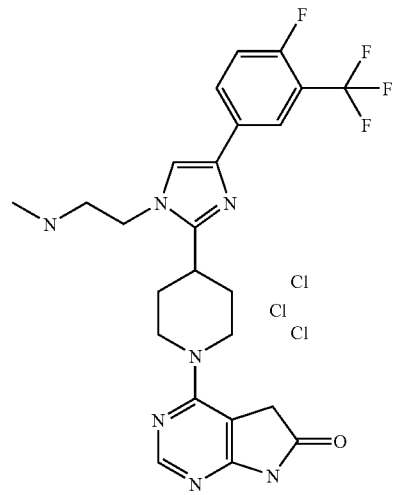

Dissolve (2-{4-(4-fluoro-3-trifluoromethyl-phenyl)-2-[1-(6-oxo-6,7-dihydro-5H-pyrrolo[2,3-d]pyrimidin-4-yl)-piperidin-4-yl]-imidazol-1-yl}-ethyl)-methyl-carbamic acid benzyl ester (213 μmol; 136 mg) in conc. HCl (8 mL) and heat to 50° C. for 60 min. Cool to RT, extract 2 times with ether, evaporate the organic layer, co-evaporate the residue 2 times with MeOH, co-evaporate the residue 2 times with DCM/MeOH to provide 129.6 mg (0.21 mmol; 99%) of the title compound. MS (ES+): m/z=504 (M+H).

Prepare the following examples essentially as described for 4-{4-[4-(4-fluoro-3-trifluoromethyl-phenyl)-1-(2-methylamino-ethyl)-1H-imidazol-2-yl]-piperidin-1-yl}-5,7-dihydro-pyrrolo[2,3-d]pyrimidin-6-one tris hydrochloride:

| Example | Compound Name | Structure | MS (ES+): m/z |
|---|---|---|---|
| 2 | 4-{4-[4-(3-Chloro-4-fluoro-phenyl)-1-(2-methylamino-ethyl)-1H-imidazol-2-yl]-piperidin-1-yl}-5,7-dihydro-pyrrolo [2,3-d]pyrimidin-6-one tris hydrochloride | 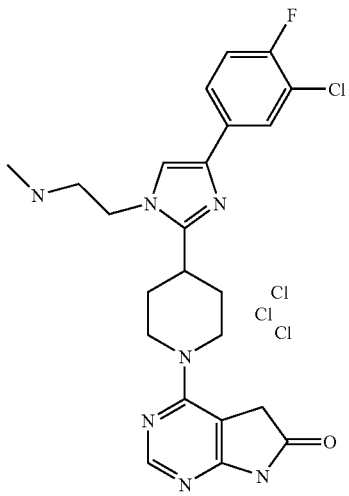 | 470 (M + H) |

-continued

| Example | Compound Name | Structure | MS (ES+): m/z |
|---|---|---|---|
| 3 | 4-{4-[4-(3-Chloro-4-fluoro-phenyl)-1-(R)-1-pyrrolidin-2-ylmethyl-1H-imidazol-2-yl]-piperidin-1-yl}-5,7-dihydro-pyrrolo [2,3-d]pyrimidin-6-one tris hydrochloride | 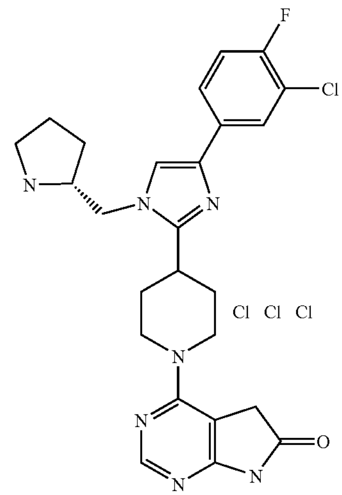 | 496 (M + H) |
| 4 | 4-{4-[1-(2-Amino-ethyl)-4-(4-fluoro-3-trifluoromethyl-phenyl)-1H-imidazol-2-yl-]-piperidin-1-yl}-dihydro-pyrrolo[2,3-d]pyrimidin-6-one | 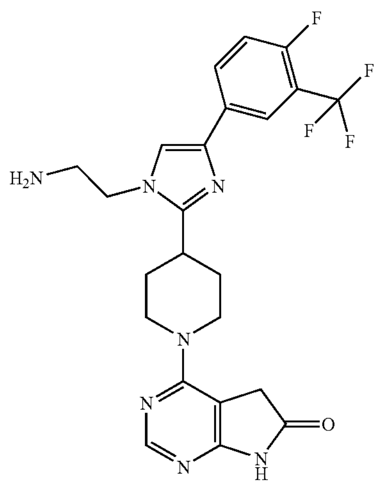 | 490 |
| 5 | 4-{4-[4-(4-Fluoro-3-trifluoromethyl-phenyl)-1-(2-methylamino-ethyl)-1H-imidazol-2-yl]-piperidin-1-yl}-5,7-dihydro-pyrrolo[2,3-d]pyrimidin-6-one | 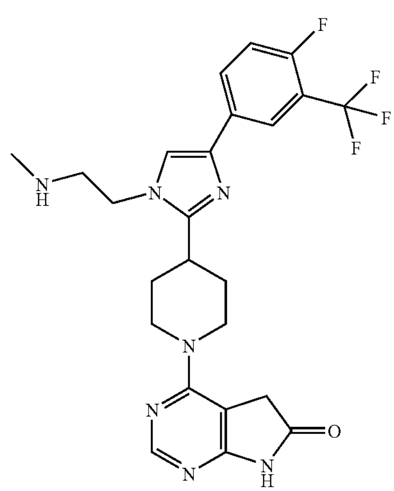 | 504 |

-continued

| Example | Compound Name | Structure | MS (ES+): m/z |
|---|---|---|---|
| 6 | (R)-4-{4-[4-(4-Fluoro-3-trifluoromethyl-phenyl)-1-(piperidin-3-yl)-1H-imidazol-2-yl]-piperidin-1-yl}-5H-pyrrolo[2,3-d]pyrimidin-6(7H)-one tris hydrochloride | 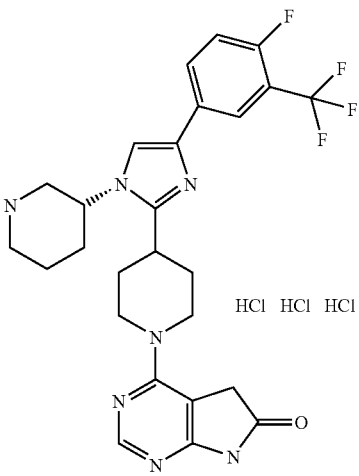 | 530 (M + 1) |
| 7 | (S)-6-{4-[4-(3-Chloro-4-fluorophenyl)-1-(pyrrolidin-2-ylmethyl)-1H-imidazol-2-yl]-piperidin-1-yl}-7-ethyl-7H-purin-8(9H)-one hydrochloride | 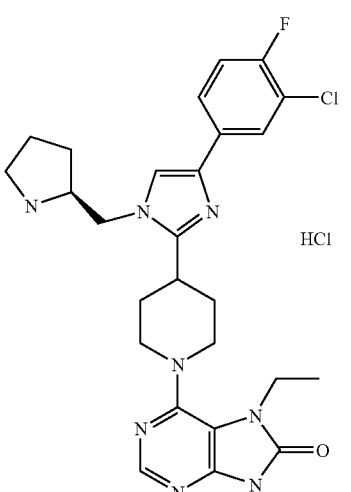 | 526 |
| 8 | (R)-6-{4-[4-(3-Chloro-4-fluorophenyl)-1-(pyrrolidin-2-ylmethyl)-1H-imidazol-2-yl]-piperidin-1-yl}-7-ethyl-7H-purin-8(9H)-one hydrochloride | 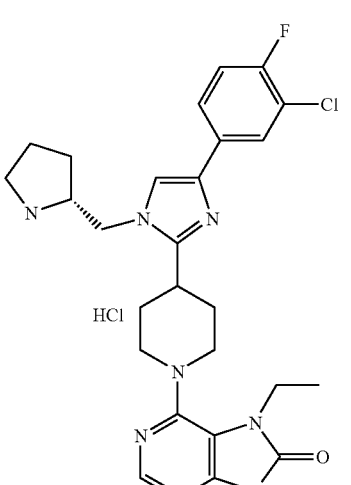 | 526 |

| Example | Compound Name | Structure | MS (ES+): m/z |
|---|---|---|---|
| 9 | 6-{4-[4-(3,4-Difluorophenyl)-1-(2-(methylamino)ethyl)-1H-imidazol-2-yl]-piperidin-1-yl}-7-ethyl-7H-purin-8(9H)-one hydrochloride | 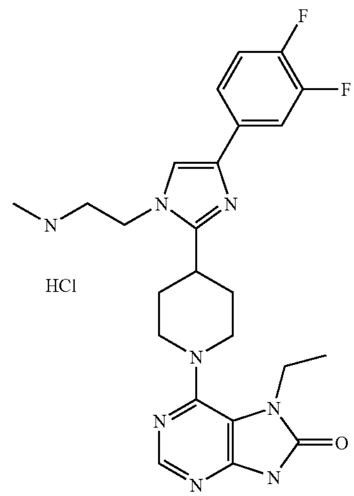 | 483 |
| 10 | 4-{4-[4-(3,4-Difluorophenyl)-1-(pyrrolidin-2-ylmethyl)-1H-imidazol-2-yl]-piperidin-1-yl}-5H-pyrrolo[2,3-d]pyrimidin-6(7H)-one | 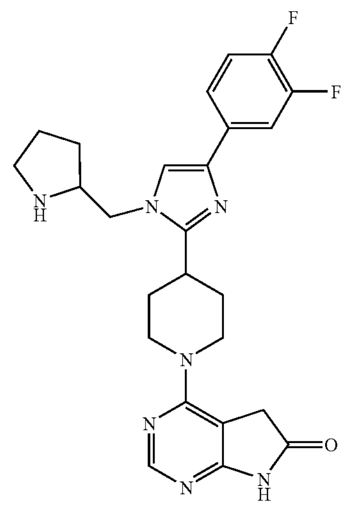 | 480 |
| 11 | 4-{4-[4-(4-Fluoro-3-trifluoromethyl-phenyl)-1-(pyrrolidin-2-ylmethyl)-1H-imidazol-2-yl]-piperidin-1-yl}-5H-pyrrolo[2,3-d]pyrimidin-6(7H)-one hydrochloride | 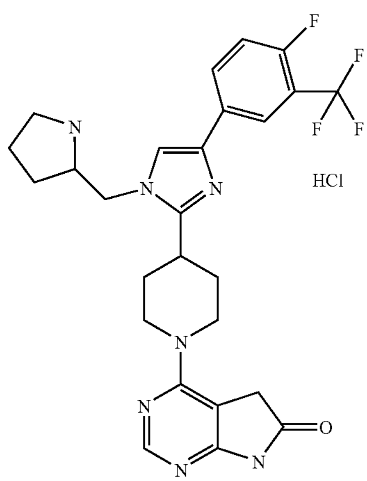 | 530 (M + 1) |

Example 11a

5-Ethyl-4-{4-[4-(4-fluoro-3-(trifluoromethyl)phenyl)-1-((S)-piperidin-2-ylmethyl)-1H-imidazol-2-yl]-piperidin-1-yl}-5,7-dihydro-pyrrolo[2,3-d]pyrimidin-6-one tris hydrochloride

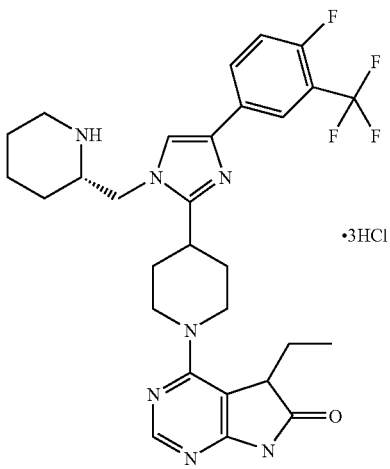

Charge (2S)-benzyl 2-((2-(1-(5-ethyl-6-oxo-6,7-dihydro-5H-pyrrolo[2,3-d]pyrimidin-4-yl)piperidin-4-yl)-4-(4-fluoro-3-(trifluoromethyl)phenyl)-1H-imidazol-1-yl)methyl)piperidine-1-carboxylate (0.45 g; 1.0 eq) in concentrated HCl (10 mL) and heat at 50° C. for 1 hour. After completion, concentrate the reaction mass, strip with toluene and triturate and wash with diethyl ether followed by DCM and pentane. Dry under vacuum to get 0.39 g (90%) of the title compound as an off-white solid. (ES+): m/z=572 (M+H).

Example 12

4-{4-[4-(4-Fluoro-3-trifluoromethyl-phenyl)-1-((R)-1-methyl-piperidin-3-yl)-1H-imidazol-2-yl]-piperidin-1-yl}-5,7-dihydro-pyrrolo[2,3-d]pyrimidin-6-one hydrochloride

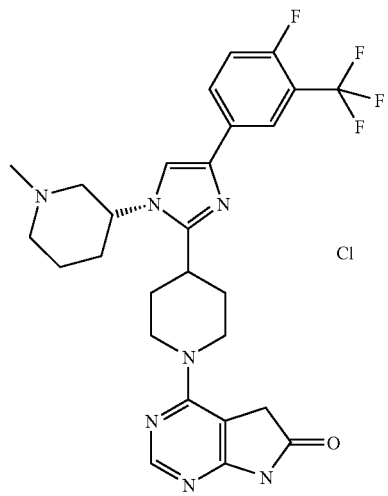

Combine potassium tert-butoxide (1.1 equiv; 321 μmol; 36.8 mg); IPrPd(acac)Cl (0.1 equiv; 29.2 μmol; 18.4 mg) and stir bar in 4 mL vial and purge with nitrogen for 10 min. Add anhydrous DME (2.5 mL) followed by 4-chloro-5,7-dihydro-pyrrolo[2,3-d]pyrimidin-6-one (1 equiv; 292 μmol; 50 mg); (R)-3-[4-(4-fluoro-3-trifluoromethyl-phenyl)-2-piperidin-4-yl-imidazol-1-yl]-1-methyl-piperidine (1.1 equiv; 321 μmol; 131.8 mg) and heat to 80° C. for 18 h. Dilute with 15 mL water, filter, and rinse with water. Dissolve purple solid in EA, wash with saturated sodium bicarbonate, brine, dry with anhydrous MgSO$_4$, filter, evaporate and purify on 40 g silica gel with 2-10% MeOH/DCM to provide 99.6 mg (0.18 mmol; 63%) of the title compound as the free base. Dissolve in DCM, add 1 equiv 1M HCl in ether and evaporate to provide 101 mg of the title compound. MS (ES+): m/z=544 (M+H).

Example 13

4-{4-[1-(2-Dimethylamino-2-methyl-propyl)-4-(4-fluoro-3-trifluoromethyl-phenyl)-1H-imidazol-2-yl]-piperidin-1-yl}-5,7-dihydro-pyrrolo[2,3-d]pyrimidin-6-one hydrochloride

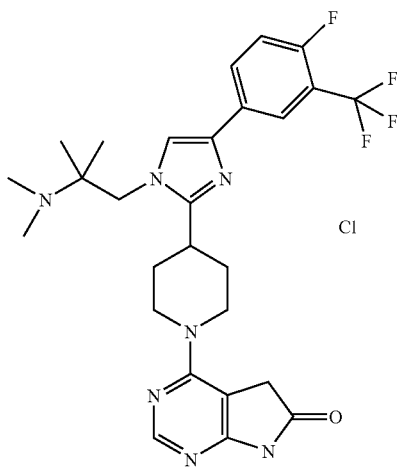

Combine {2-[4-(4-fluoro-3-trifluoromethyl-phenyl)-2-piperidin-4-yl-imidazol-1-yl]-1,1-dimethyl-ethyl}-dimethyl-amine tris hydrochloride (247 μmol; 200 mg); 4-chloro-5,7-dihydro-pyrrolo[2,3-d]pyrimidin-6-one (1.5 equiv; 575 μmol; 97.5 mg); TEA (1.92 mmol; 267 μL); DMF (2 mL) and heat in microwave reactor at 160° C. for 30 min. Evaporate and purify on 40 g silica gel with 2-7.5% MeOH/DCM to provide 137.3 mg (0.25 mmol; 66%) of the title compound as the free base. Dissolve in DCM/MeOH, add 1 equiv 1M HCl in ether and evaporate to provide 162.4 mg of the title compound. MS (ES+): m/z=546 (M+H).

Prepare the following examples essentially as described for 4-{4-[1-(2-dimethylamino-2-methyl-propyl)-4-(4-fluoro-3-trifluoromethyl-phenyl)-1H-imidazol-2-yl]-piperidin-1-yl}-5,7-dihydro-pyrrolo[2,3-d]pyrimidin-6-one hydrochloride:

| Example | Compound Name | (M + H) | MS (ES+): m/z |
|---|---|---|---|
| 14 | 4-{4-[4-(4-Fluoro-3-trifluoromethyl-phenyl)-1-(2-(isopropyl-methyl-amino)-ethyl)-1H-imidazol-2-yl]-piperidin-1-yl}-5,7-dihydro-pyrrolo[2,3-d]pyrimidin-6-one hydrochloride | | 546 |
| 15 | 4-{4-[1-(2-tert-Butylamino-ethyl)-4-(4-fluoro-3-trifluoromethyl-phenyl)-1H-imidazol-2-yl]-piperidin-1-yl}-5,7-dihydro-pyrrolo[2,3-d]pyrimidin-6-one bis hydrochloride | | 546 |
| 16 | 4-{4-[4-(4-Fluoro-3-trifluoromethyl-phenyl)-1-(2-((R)-2-hydroxymethyl-pyrrolidin-1-yl)-ethyl)-1H-imidazol-2-yl]-piperidin-1-yl}-5,7-dihydro-pyrrolo[2,3-d]pyrimidin-6-one hydrochloride | | 574 |

| Example | Compound Name | (M + H) | MS (ES+): m/z |
|---|---|---|---|
| 17 | 4-{4-[4-(3-Chloro-4-fluoro-phenyl)-1-(2-(ethyl-isopropyl-amino)-ethyl)-1H-imidazol-2-yl]-piperidin-1-yl}-5,7-dihydro-pyrrolo[2,3-d]pyrimidin-6-one hydrochloride | | 527 |
| 18 | 4-{4-[1-(2-tert-Butylamino-ethyl)-4-(3-chloro-4-fluoro-phenyl)-1H-imidazol-2-yl]-piperidin-1-yl}-5,7-dihydro-pyrrolo[2,3-d]pyrimidin-6-one hydrochloride | | 512 |
| 19 | 4-{4-[4-(3-Chloro-4-fluoro-phenyl)-1-(2-(isopropyl-methyl-amino)-ethyl)-1H-imidazol-2-yl]-piperidin-1-yl}-5,7-dihydro-pyrrolo[2,3-d]pyrimidin-6-one hydrochloride | | 512 |

-continued

| Example | Compound Name | (M + H) | MS (ES+): m/z |
|---------|---------------|---------|---------------|
| 20 | 6-{4-[1-(2-Dimethylamino-ethyl)-4-(4-fluoro-3-trifluoromethyl-phenyl)-1H-imidazol-2-yl]-piperidin-1-yl}-7,9-dihydro-purin-8-one | | 519 |

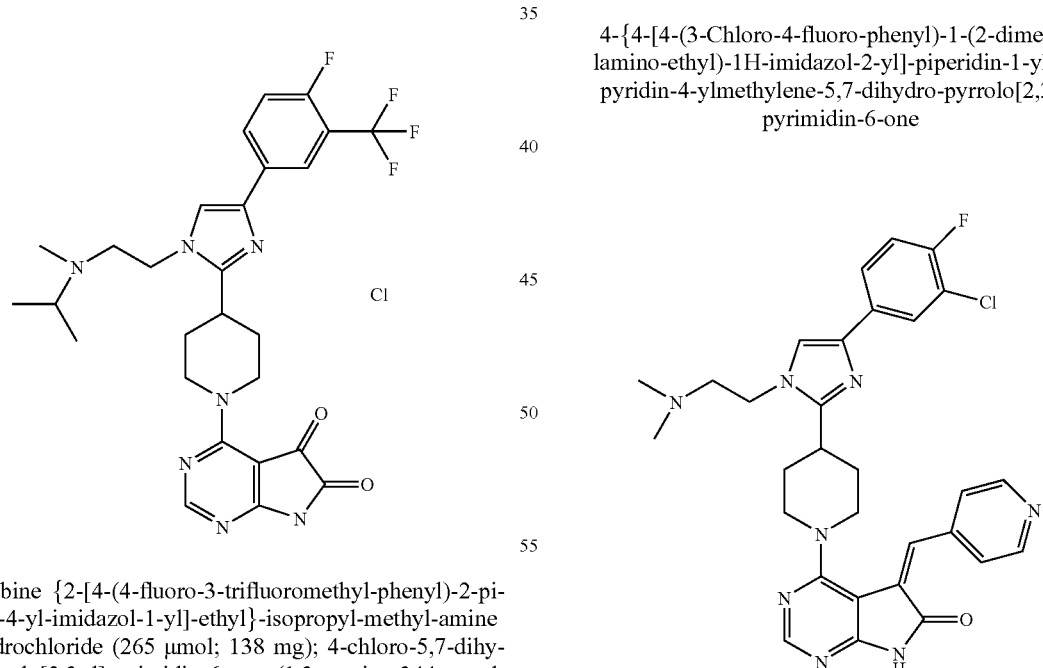

Example 21

4-{4-[4-(4-Fluoro-3-trifluoromethyl-phenyl)-1-(2-(isopropyl-methyl-amino)-ethyl)-1H-imidazol-2-yl]-piperidin-1-yl}-7H-pyrrolo[2,3-d]pyrimidine-5,6-dione hydrochloride Combine {2-[4-(4-fluoro-3-trifluoromethyl-phenyl)-2-piperidin-4-yl-imidazol-1-yl]-ethyl}-isopropyl-methyl-amine tris hydrochloride (265 μmol; 138 mg); 4-chloro-5,7-dihydro-pyrrolo[2,3-d]pyrimidin-6-one (1.3 equiv; 344 μmol; 58.4 mg); nitrogen saturated DMF (1 mL) and TEA (10 equiv; 2.65 mmol; 369 μL) and heat to 160° C. in microwave for 30 min. Evaporate and dissolve the residue in MeOH, load onto 10 g SCX; wash with MeOH then DCM; elute with 2M NH₃/MeOH. Evaporate to give 189 mg dark reddish residue. Dissolve the residue in 7N NH₃/MeOH and stir in pressure vessel at 50° C. for 4 h and evaporate. Purify the residue twice on 40 g silica gel with 5-10% MeOH/DCM to provide 26.3 mg (0.047 mmol; 18%) of the title compound as the free base. Dissolve in DCM and add 2 equiv (23.5 μL) 4M HCl/dioxane and evaporate to provide 27.9 mg of the title compound. MS (ES+): m/z=560 (M+H).

Example 22

4-{4-[4-(3-Chloro-4-fluoro-phenyl)-1-(2-dimethylamino-ethyl)-1H-imidazol-2-yl]-piperidin-1-yl}-5-pyridin-4-ylmethylene-5,7-dihydro-pyrrolo[2,3-d]pyrimidin-6-one Combine {2-[4-(3-chloro-4-fluoro-phenyl)-2-piperidin-4-yl-imidazol-1-yl]-ethyl}-dimethyl-amine tris hydrochloride (0.5 g; 0.0013 mol; 1.0 equiv); 4-chloro-5-[1-pyridin-4-yl-methylidene]-5,7-dihydro-pyrrolo[2,3-d]pyrimidin-6-one (0.34 g; 0.0013 mol; 1.0 equiv); DIPEA (1.7 mL; 0.0098 mol; 7.6 equiv); 2-propanol (15 mL) and microwave at 80° C. for 20 min. Cool and dilute with water. Extract with EA and wash with brine. Concentrate the crude and purify by reverse phase HPLC to give the title compound as a mixture of E and Z isomers (0.04 g; 5.4%). MS (ES+): m/z=573 (M+H). (Note: All olefin compounds are mixtures of E and Z isomers.)

Prepare the following examples in a manner similar to that described for 4-{4-[4-(3-Chloro-4-fluoro-phenyl)-1-(2-dimethylamino-ethyl)-1H-imidazol-2-yl]-piperidin-1-yl}-5-pyridin-4-ylmethylene-5,7-dihydro-pyrrolo[2,3-d]pyrimidin-6-one.

| Example | Compound Name | | MS (ES+): m/z (M + H) |
|---|---|---|---|
| 23 | 4-{4-[1-(2-Dimethylamino-ethyl)-4-(4-fluoro-3-trifluoromethyl-phenyl)-1H-imidazol-2-yl]piperidin-1-yl}-5-(1H-imidazol-2-ylmethylene)-5,7-dihydro-pyrrolo[2,3-d]pyrimidin-6-one | | 596 |
| 24 | 4-{4-[1-(2-Dimethylamino-ethyl)-4-(4-fluoro-3-trifluoromethyl-phenyl)-1H-imidazol-2-yl]-piperidin-1-yl}-5-thiazol-5-ylmethylene-5,7-dihydro-pyrrolo[2,3-d]pyrimidin-6-one | | 613 |

-continued

| Example | Compound Name | | MS (ES+): m/z (M + H) |
|---|---|---|---|
| 25 | 4-{4-[4-(3,4-Difluoro-phenyl)-1-(2-dimethylamino-ethyl)-1H-imidazol-2-yl]-piperidin-1-yl}-5-thiazol-5-ylmethylene-5,7-dihydro-pyrrolo[2,3-d]pyrimidin-6-one | 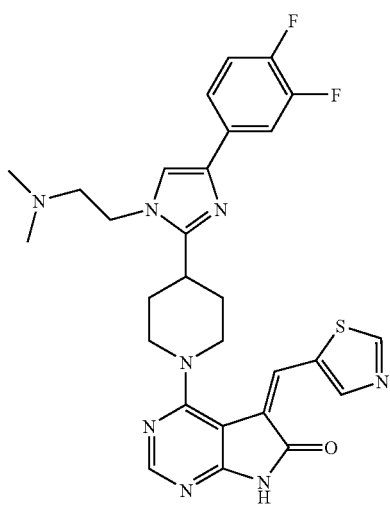 | 563 |
| 26 | 4-{4-[1-(2-Dimethylamino-ethyl)-4-(4-fluoro-3-trifluoromethyl-phenyl)-1H-imidazol-2-yl]-piperidin-1-yl}-5-(3H-imidazol-4-ylmethylene)-5,7-dihydro-pyrrolo[2,3-d]pyrimidin-6-one | 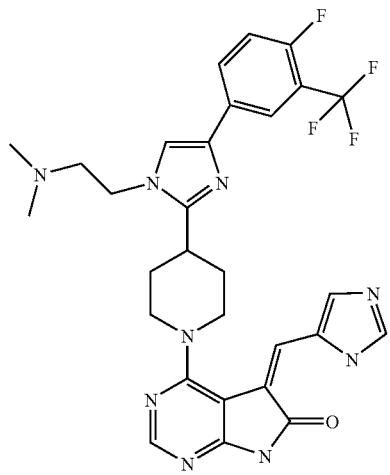 | 596 |
| 27 | 4-{4-[4-(3-Chloro-4-fluoro-phenyl)-1-(2-dimethylamino-ethyl)-1H-imidazol-2-yl]-piperidin-1-yl}-5-thiazol-2-yl methylene-5,7-dihydro-pyrrolo[2,3-d]pyrimidin-6-one | 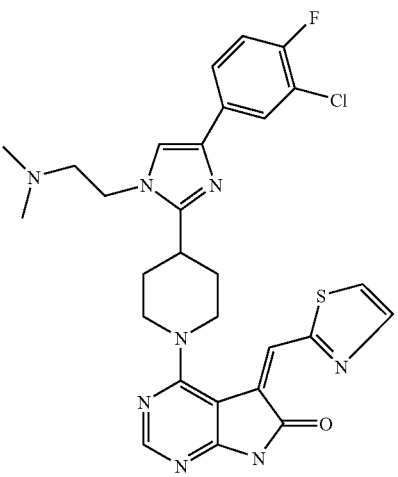 | 579 |

-continued

| Example | Compound Name | (M + H) | MS (ES+): m/z |
|---|---|---|---|
| 28 | 4-{4-[4-(3-Chloro-4-fluoro-phenyl)-1-(2-dimethylamino-ethyl)-1H-imidazol-2-yl]-piperidin-1-yl}-5-thiazol-5-ylmethylene-5,7-dihydro-pyrrolo[2,3-d]pyrimidin-6-one | | 579 |
| 29 | 4-{4-[4-(3,4-Difluorophenyl)-1-(2-dimethylamino-ethyl)-1H-imidazol-2-yl]-piperidin-1-d]pyrimidin-6(7H)-one | | 578 |

Example 30

4-{4-[4-(3,4-Difluoro-phenyl)-1-(2-dimethylamino-ethyl)-1H-imidazol-2-yl]-piperidin-1-yl}-5,5-dimethyl-5,7-dihydro-pyrrolo[2,3-d]pyrimidin-6-one

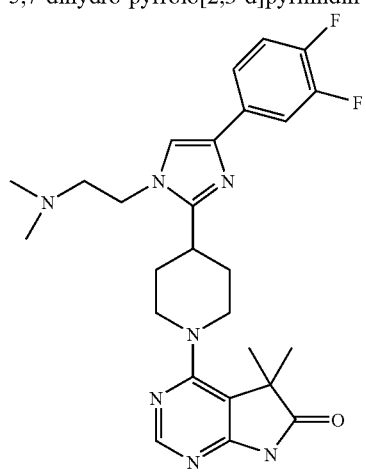

Combine 2-(4-(3,4-difluorophenyl)-2-(piperidin-4-yl)-1H-imidazol-1-yl-N,N-dimethyl ethanamine tris hydrochloride (0.28 g; 0.00064 mol), 4-chloro-5,5-dimethyl-5,7-dihydro-pyrrolo[2,3-d]pyrimidin-6-one (0.15 g; 0.00076 mol), TEA (0.74 mL; 0.0053 mol) in DMF (8.43 mL) and heat in microwave at 150° C. for 3 h; cool to RT and evaporate under vacuum. Quench the reaction with saturated sodium bicarbonate solution and extract with EA. Evaporate the EA layer and purify on silica column (60-120 mesh) packed in DCM, first with two volumes of 10% Acetone/DCM followed by 1-5% MeOH/DCM as eluent to give the title compound (0.05 g; 15.92%). MS (ES+): m/z=496 (M+H).

Prepare the following example in manner similar to that described for 4-{4-[4-(3,4-Difluoro-phenyl)-1-(2-dimethyl-lamino-ethyl)-1H-imidazol-2-yl]-piperidin-1-yl}-5,5-dimethyl-5,7-dihydro-pyrrolo[2,3-d]pyrimidin-6-one:

| Example | Compound Name | Structure | MS (ES+) m/z (M + 1) |
|---|---|---|---|
| 31 | 4-{4-[1-(2-Dimethylamino-ethyl)-4-(4-fluoro-3-trifluoromethyl-phenyl)-1H-imidazol-2-yl]-piperidin-1-yl}-5,5-dimethyl-5,7-dihydro pyrrolo [2,3-dipyrimidin-6-one | 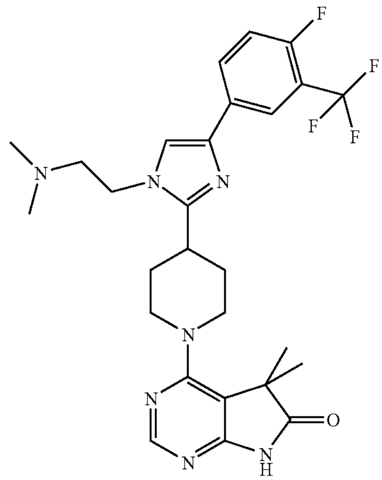 | 546 |

Example 32

4-{4-[4-(3-Chloro-4-fluoro-phenyl)-1-(2-pyrrolidin-1-yl-ethyl)-1H-imidazol-2-yl]-piperidin-1-yl}-5,5-dimethyl-5,7-dihydro-pyrrolo[2,3-d]pyrimidin-6-one

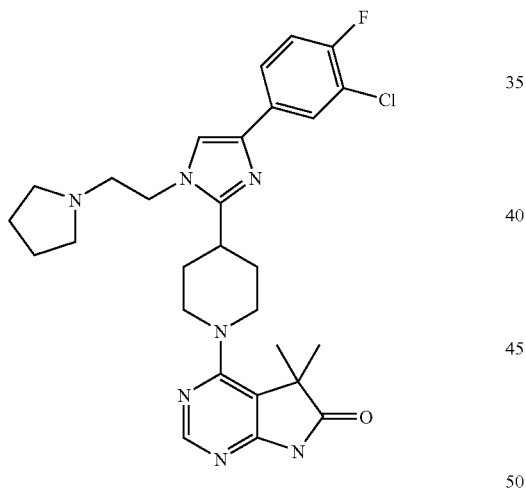

Combine 4-[4-(3-Chloro-4-fluoro-phenyl)-1-(2-pyrrolidin-1-yl-ethyl)-1H-imidazol-2-yl]-piperidine tris hydrochloride (0.3 g; 0.00062 mol), 4-chloro-5,5-dimethyl-5,7-dihydro-pyrrolo[2,3-d]pyrimidin-6-one (0.16 g; 0.0008 mol), 1,8-diazabicyclo[5.4.0]undec-7-ene (DBU, 0.76 mL; 0.0051 mol) into IPA (10 mL) and stir at 120° C. for 16 h; cool and concentrate. Quench the reaction with saturated sodium bicarbonate solution and extract with EA. Evaporate the EA layer and purify by column chromatography using 0-5% MeOH/DCM as eluent to afford the title compound (0.045 g; 13.5%). MS (ES+): m/z=538 (M+1).

Prepare the following compound in manner similar to that described for 4-{4-[4-(3-Chloro-4-fluoro-phenyl)-1-(2-pyrrolidin-1-yl-ethyl)-1H-imidazol-2-yl]-piperidin-1-yl}-5,5-dimethyl-5,7-dihydro-pyrrolo[2,3-d]pyrimidin-6-one:

| Example | Compound Name | Structure | MS (ES+): m/z (M + 1) |
|---|---|---|---|
| 33 | 4-{4-[4-(3,4-Difluoro-phenyl)-1-(2-pyrrolidin-1-yl-ethyl)-1H-imidazol-2-yl]-piperidin-1-yl}-5,5-dimethyl-5,7-dihydro-pyrrolo[2,3-d]pyrimidin-6-one | 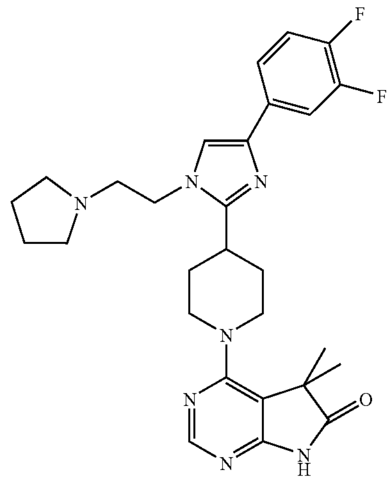 | 522 |

Example 34

5-Benzyl-4-{4-[1-(2-dimethylamino-ethyl)-4-(4-fluoro-3-trifluoromethyl-phenyl)-1H-imidazol-2-yl]-piperidin-1-yl}-5,7-dihydro-pyrrolo[2,3-d]pyrimidin-6-one

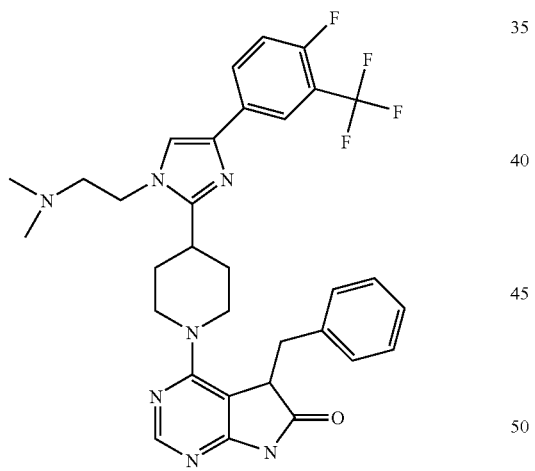

Combine 5-benzylidene-4-(4-(1-(2-dimethylamino-ethyl)-4-(4-fluoro-3-trifluoromethyl-phenyl)-1H-imidazol-2-yl)-piperidin-1-yl)-5,7-dihydro-pyrrolo[2,3-d]pyrimidin-6-one (0.3 g; 0.00050 mol), PtO$_2$/C (0.15 g; 0.00055 mol) in ethanol (5 mL) and stir under a hydrogen balloon atmosphere at 80° C. for 16 h. Cool the reaction to RT, filter through Celite® and concentrate. Purify over silica gel column using methanol in DCM as eluent to give the title compound (105 mg; 35%). MS (ES+): m/z=608 (M+1).

Prepare the following examples in manner similar to that described for 5-benzyl-4-{4-[1-(2-dimethylamino-ethyl)-4-(4-fluoro-3-trifluoromethyl-phenyl)-1H-imidazol-2-yl]-piperidin-1-yl}-5,7-dihydro-pyrrolo[2,3-d]pyrimidin-6-one:

| Example | Compound Name | Structure | MS (ES+): m/z (M + 1) |
|---|---|---|---|
| 35 | 5-Benzyl-4-{4-[4-(3,4-difluorophenyl)-1-(2-dimethylamino-ethyl)-1H-imidazol-2-yl]-piperidin-1-yl}-5,7-dihydro-pyrrolo[2,3-d]pyrimidin-6-one | 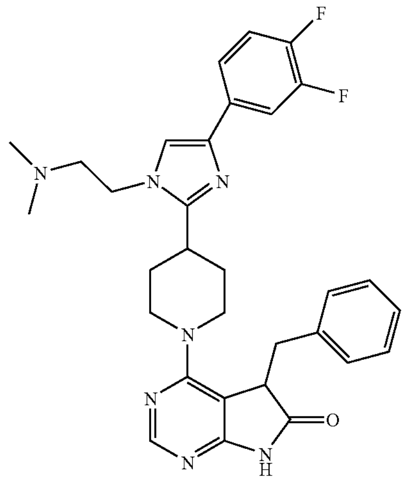 | 558 |
| 36 | 5-Benzyl-4-{4-[4-(3-chloro-4-fluoro-phenyl)-1-(2-dimethylamino-ethyl)-1H-imidazol-2-yl]-piperidin-1-yl}-5,7-dihydro-pyrrolo[2,3-d]pyrimidin-6-one | 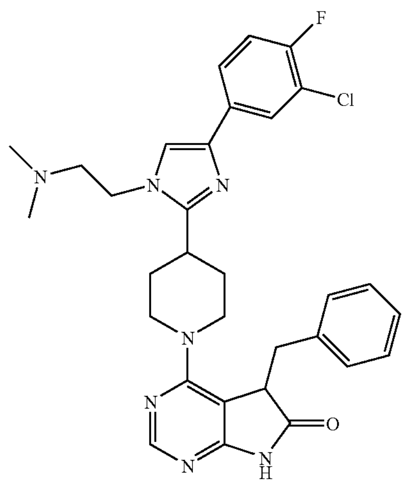 | 574 |

Example 37

4-{4-[4-(3,4-Difluoro-phenyl)-1-(2-pyrrolidin-1-yl-ethyl)-1H-imidazol-2-yl]-piperidin-1-yl}-5,7-dihydro-pyrrolo[2,3-d]pyrimidin-6-one

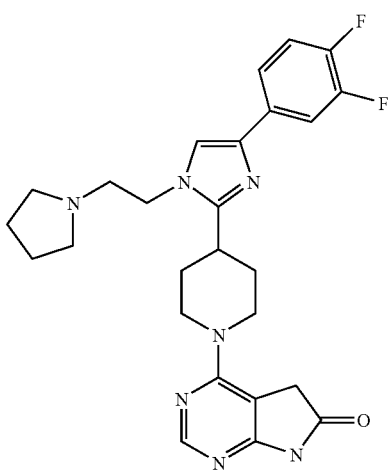

Combine 4-(4-(3,4-difluoro-phenyl)-1-(2-pyrrolidin-1-yl-ethyl)-1H-imidazol-2-yl)-piperidine tris hydrochloride (0.3 g; 0.00065 mol), 4-chloro-5,7-dihydro-pyrrolo[2,3-d]pyrimidin-6-one (0.15 g; 0.00083 mol), DIPEA, (1.00 mL, 0.0057 mol) into IPA (9 mL) and heat in a microwave at 80° C. for 1 h; cool and concentrate. Quench with saturated sodium bicarbonate solution and extract with EA. Evaporate the EA and purify by column chromatography using 0-10% MeOH/DCM as eluent to give the title compound (0.05 g; 15.67%). MS (ES+): m/z=494 (M+1).

Prepare the following examples in manner similar to that described for 4-{4-[4-(3,4-Difluoro-phenyl)-1-(2-pyrrolidin-1-yl-ethyl)-1H-imidazol-2-yl]-piperidin-1-yl}-5,7-dihydro-pyrrolo[2,3-d]pyrimidin-6-one:

| Example | Compound Name | Structure | MS (ES+) m/z (M + 1) |
|---|---|---|---|
| 38 | 4-{4-[1-(2-Dimethylamino-ethyl)-4-(4-fluoro-3-trifluoromethyl-phenyl)-1H-imidazol-2-yl]-4-hydroxy-piperidin-1-yl}-5,7-dihydro-pyrrolo[2,3-d]pyrimidin-6-one | 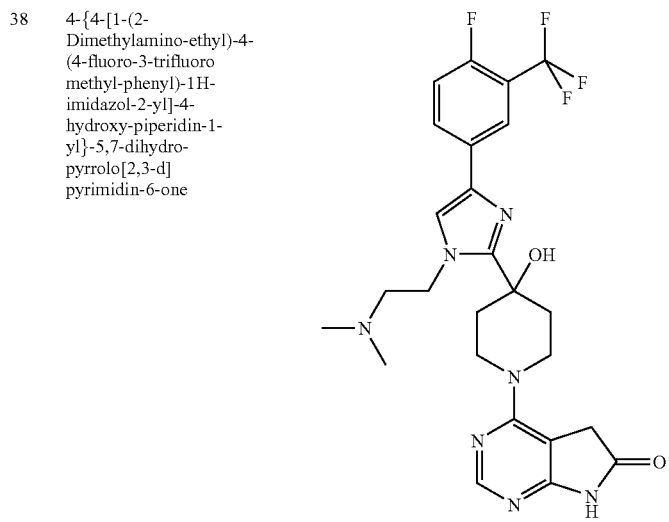 | 534 |
| 39 | 4-{4-[4-(3,4-Difluoro-phenyl)-1-(2-dimethylamino-ethyl)-1H-imidazol-2-yl]-piperidin-1-yl}-5,7-dihydro-pyrrolo[2,3-d]pyrimidin-6-one | 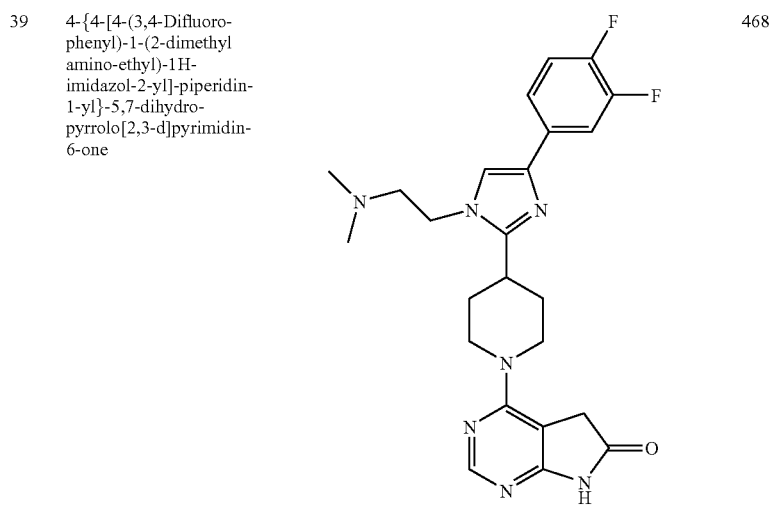 | 468 |
| 40 | 4-{4-[4-(4-Fluoro-3-trifluoromethyl-phenyl)-1-(2-pyrrolidin-1-yl-ethyl)-1H-imidazol-2-yl]-4-hydroxy-piperidin-1-yl}-5,7-dihydro-pyrrolo[2,3-d]pyrimidin-6-one | 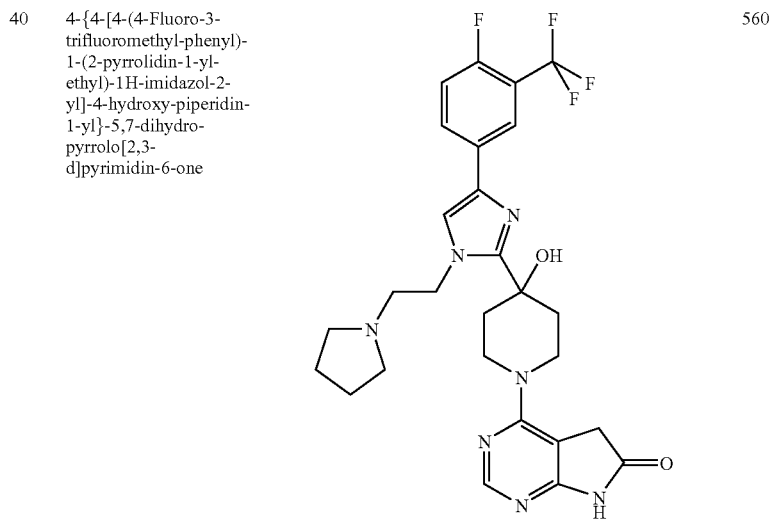 | 560 |

-continued

| Example | Compound Name | Structure | MS (ES+) m/z (M + 1) |
|---|---|---|---|
| 41 | 4-{4-[4-(3-Chloro-4-fluoro-phenyl)-1-(2-pyrrolidin-1-yl-ethyl)-1H-imidazol-2-yl]-piperidin-1-yl}-5,7-dihydro-pyrrolo[2,3-d]pyrimidin-6-one | 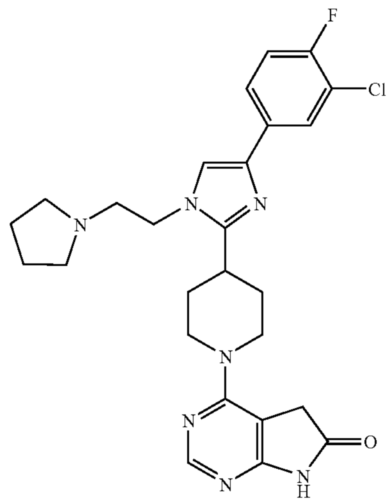 | 510 |
| 42 | 4-{4-[4-(3-Chloro-4-fluoro-phenyl)-1-(2-dimethylamino-ethyl)-1H-imidazol-2-yl]-4-hydroxy-piperidin-1-yl}-5,7-dihydro-pyrrolo[2,3-d]pyrimidin-6-one | 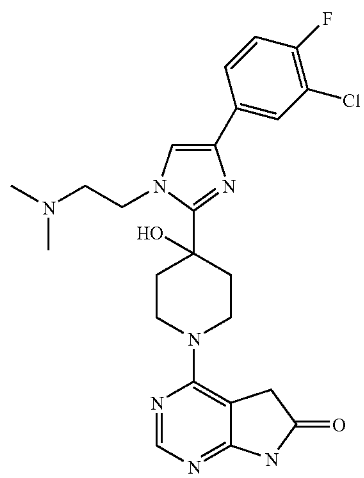 | 500 |
| 43 | 4-{4-[4-(3-Chloro-4-fluoro-phenyl)-1-(2-dimethylamino-ethyl)-1H-imidazol-2-yl]-piperidin-1-yl}-5,7-dihydro-pyrrolo[2,3-d]pyrimidin-6-one | 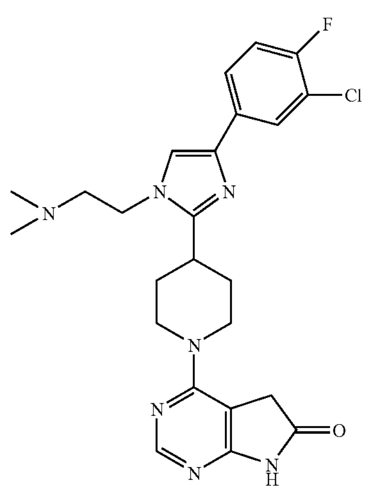 | 484 |

-continued

| Example | Compound Name | Structure | MS (ES+) m/z (M + 1) |
|---------|---------------|-----------|----------------------|
| 44 | 4-{4-[4-(3-Chloro-4-fluoro-phenyl)-1-(2-pyrrolidin-1-yl-ethyl)-1H-imidazol-2-yl]-4-hydroxy-piperidin-1-yl}-5,7-dihydro-pyrrolo[2,3-d]pyrimidin-6-one dihydrochloride | 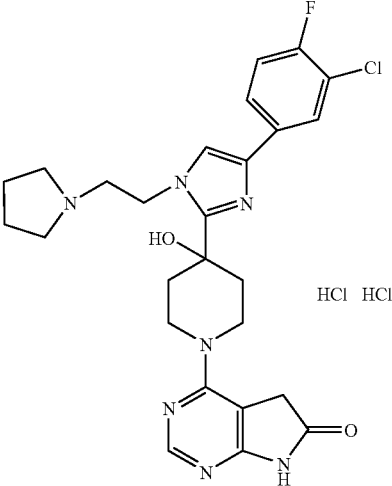 | 526 |
| 45 | 4-{4-[1-(2-Dimethylamino-ethyl)-4-(4-fluoro-3-trifluoromethyl-phenyl)-1H-imidazol-2-yl] piperidin-1-yl}-5,7-dihydro-pyrrolo[2,3-d]-pyrimidin-6-one | 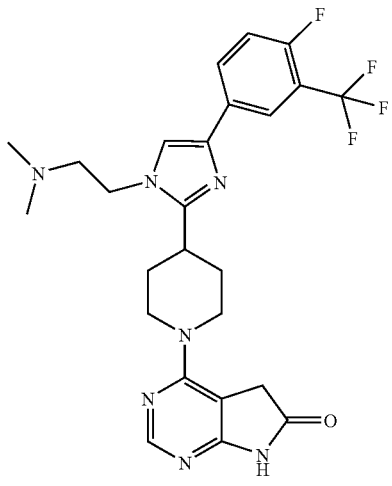 | 518 |
| 46 | 7-Ethyl-6-{4-[4-(4-fluoro-3-trifluoromethyl-phenyl)-1-(2-(pyrrolidin-1-yl)ethyl)-1H-imidazol-2-yl]-piperidin-1-yl}-7H-purin-8(9H)-one | 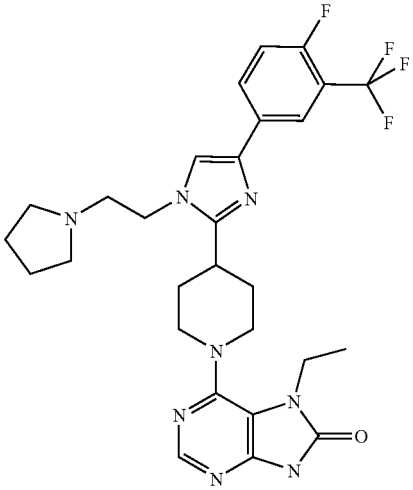 | 573 |

-continued

| Example | Compound Name | Structure | MS (ES+) m/z (M + 1) |
|---------|---------------|-----------|----------------------|
| 47 | 6-{4-[4-(3,4-Difluorophenyl)-1-(2-(pyrrolidin-1-yl)ethyl)-1H-imidazol-2-yl]-piperidin-1-yl}-7-isopropyl-7H-purin-8(9H)-one | 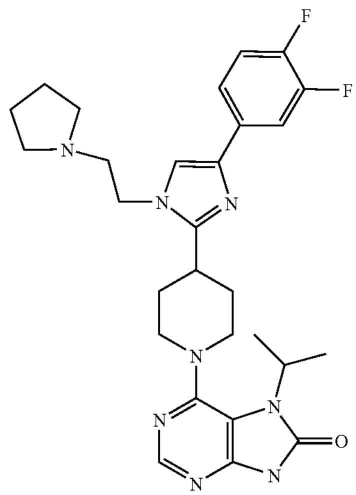 | 537 |
| 48 | 6-{4-[4-(3-Chloro-4-fluorophenyl)-1-(2-(pyrrolidin-1-yl)ethyl)-1H-imidazol-2-yl]-piperidin-1-yl}-7-ethyl-7H-purin-8(9H)-one | 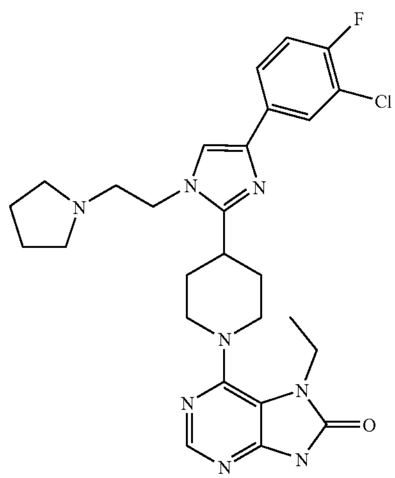 | 540 |
| 49 | 6-{4-[4-(3-Chloro-4-fluorophenyl)-1-(2-dimethylamino-ethyl)-1H-imidazol-2-yl]-piperidin-1-yl}-7-methyl-7H-purin-8(9H)-one | 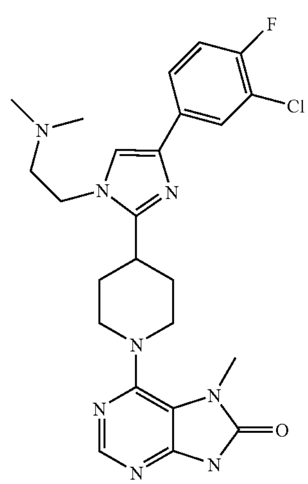 | 500 |

-continued

| Example | Compound Name | Structure | MS (ES+) m/z (M + 1) |
|---|---|---|---|
| 50 | 6-{4-[4-(3-Chloro-4-fluorophenyl)-1-(2-dimethylamino-ethyl)-1H-imidazol-2-yl]-piperidin-1-yl}-7-ethyl-7H-purin-8(9H)-one | 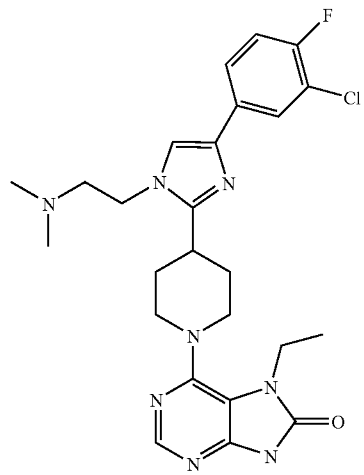 | 514 |
| 51 | 6-{4-[4-(34-Difluorophenyl)-1-(2-dimethylamino-ethyl)-1H-imidazol-2-yl]-piperidin-1-yl}-7-isopropyl-7H-purin-8(9H)-one | 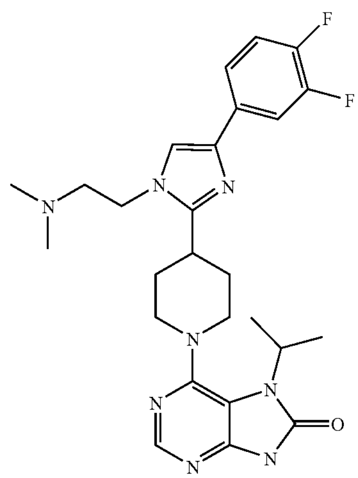 | 511 |
| 52 | 6-{4-[4-(4-Fluoro-3-trifluoromethyl-phenyl)-1-(2-(pyrrolidin-1-yl)ethyl)-1H-imidazol-2-yl]-piperidin-1-yl}-7-isopropyl-7H-purin-8(9H)-one | 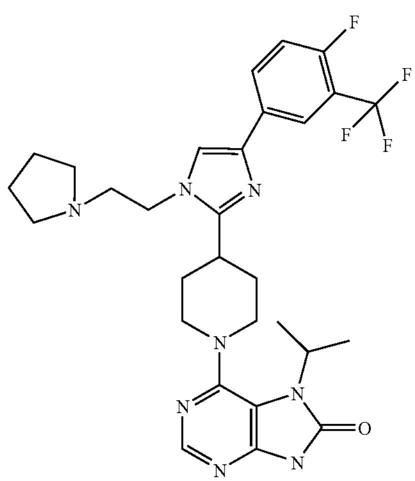 | 587 |

-continued
| Example | Compound Name | Structure | MS (ES+) m/z (M + 1) |
|---|---|---|---|
| 53 | 6-{4-[4-(3,4-Difluorophenyl)-1-(2-(pyrrolidin-1-yl)ethyl)-1H-imidazol-2-yl]-piperidin-1-yl}-7-ethyl-7H-purin-8(9H)-one | 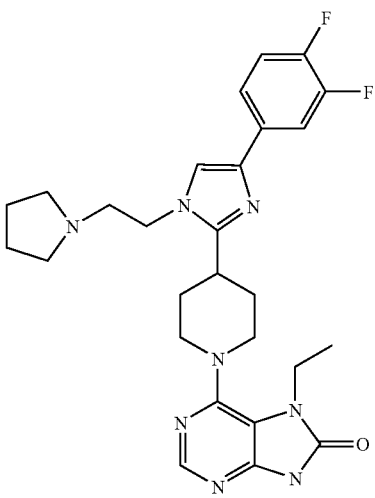 | 523 |
| 54 | 6-{4-[4-(3-Chloro-4-fluorophenyl)-1-(2-dimethylamino-ethyl)-1H-imidazol-2-yl]-piperidin-1-yl}-7-isopropyl-7H-purin-8(9H)-one | 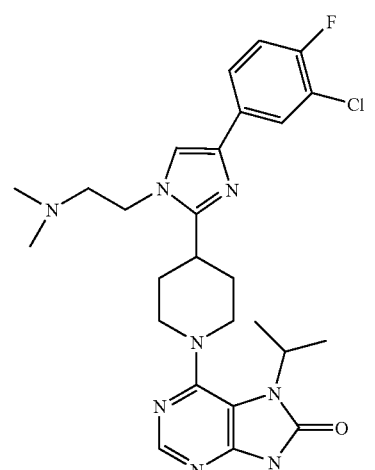 | 528 |
| 55 | 6-{4-[4-(3,4-Difluorophenyl)-1-(2-(pyrrolidin-1-yl)ethyl)-1H-imidazol-2-yl]-piperidin-1-yl}-7-methyl-7H-purin-8(9H)-one | 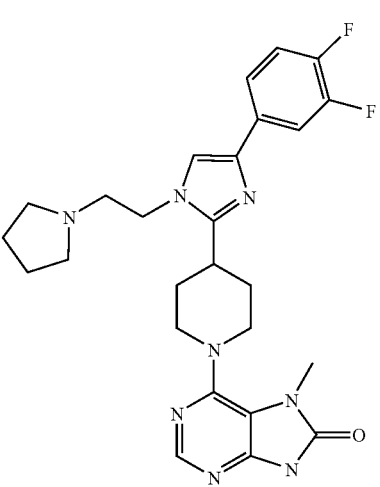 | 509 |

| Example | Compound Name | Structure | MS (ES+) m/z (M + 1) |
|---|---|---|---|
| 56 | 6-{4-[1-(2-Dimethylamino-ethyl)-4-(4-fluoro-3-trifluoromethyl-phenyl)-1H-imidazol-2-yl]-piperidin-1-yl}-7-ethyl-7H-purin-8(9H)-one | 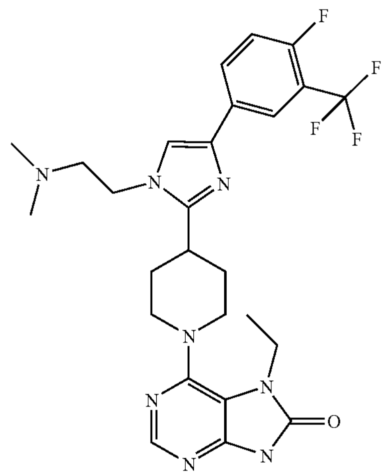 | 547 |
| 57 | 6-{4-[4-(3,4-Difluorophenyl)-1-(2-(pyrrolidin-1-yl)ethyl)-1H-imidazol-2-yl]-piperidin-1-yl}-7H-purin-8(9H)-one | 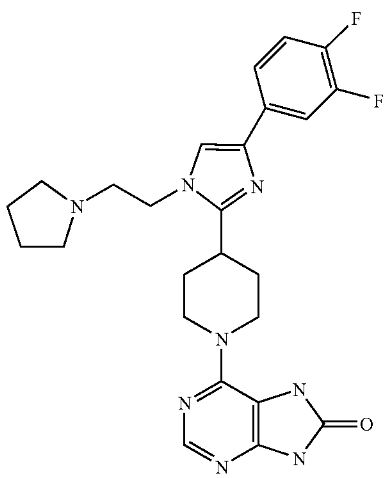 | 495 |

Example 57a

4-{4-[4-(3-Difluoromethyl-4-fluorophenyl)-1-(((R)-1-methylpiperidin-2-yl)methyl)-1H-imidazol-2-yl]-piperidin-1-yl}-5-ethyl-5,7-dihydro-pyrrolo[2,3-d]pyrimidin-6-one

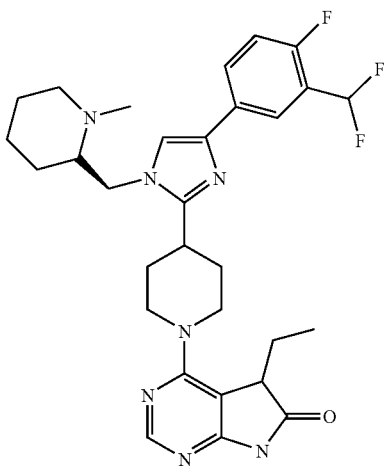

Combine (R)-2-((4-(3-(difluoromethyl)-4-fluorophenyl)-2-(piperidin-4-yl)-1H-imidazol-1-yl)methyl)-1-methylpiperidine (0.8 g, 0.0018 mol, 1.0 eq); 4-chloro-5-ethyl-5,7 dihydro-pyrrolo[2,3-d]pyrimidin-6-one (0.425 g, 0.00216 mol, 1.2 eq); DIPEA (2.3 mL, 0.0126 mol, 7.0 eq) and IPA (15 mL) in a pressure tube and heat at 120° C. overnight under sealed condition. Cool the reaction mass and dilute with water (25 mL). Extract in EA (2×50 mL) and wash the organic layer with brine (2×50 mL). Dry over anhydrous sodium sulfate and concentrate the crude compound. Filter the crude product through a short silica pad (100-200 mesh) using 0-8% MeOH-DCM). LCMS of concentrated crude product shows 70% of the desired product (m/z=568 [M+H]). Purify through reverse phase preparative HPLC to get 0.055 g of the title compound. MS (ES+): m/z=568 (M+H).

Prepare the following example in a manner similar to that described for 4-{4-[4-(3-difluoromethyl-4-fluorophenyl)-1-(((R)-1-methylpiperidin-2-yl)methyl)-1H-imidazol-2-yl]-piperidin-1-yl}-5-ethyl-5,7-dihydro-pyrrolo[2,3-d]pyrimidin-6-one:

| Example | Compound Name | Structure | MS (ES+) m/z (M + 1) |
|---|---|---|---|
| 57b | (R)-6-{4-[4-(3-Difluoromethyl-4-fluorophenyl)-1-((1-methylpiperidin-2-yl)methyl)-1H-imidazol-2-yl]-piperidin-1-yl}-7-ethyl-7H-purin-8(9H)-one | 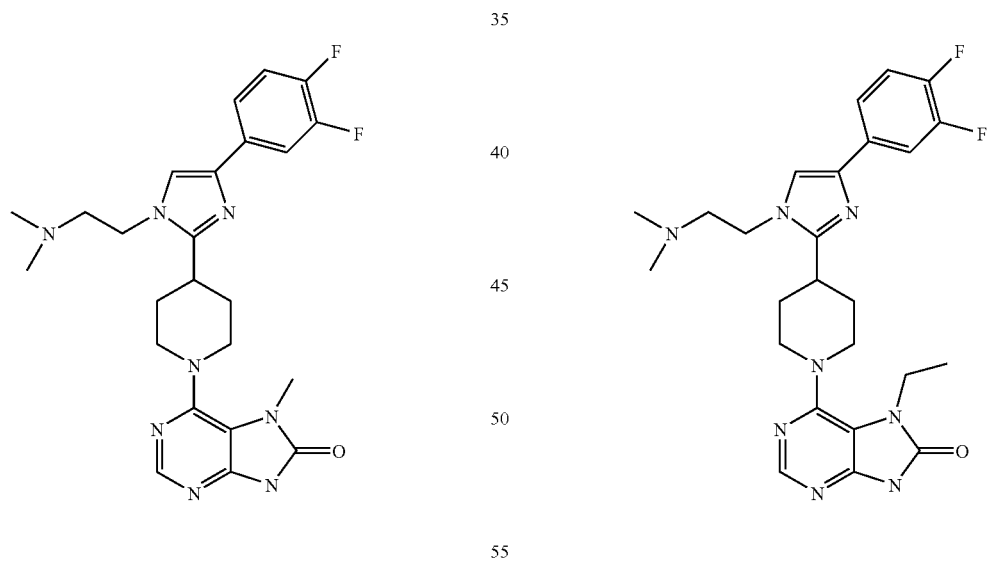 | 569 |

Example 58

6-{4-[4-(3,4-Difluoro-phenyl)-1-(2-dimethylamino-ethyl)-1H-imidazol-2-yl]-piperidin-1-yl}-7-methyl-7,9-dihydro-purin-8-one Combine 2-(4-(3,4-difluorophenyl)-2-(piperidin-4-yl)-1H-imidazol-1-yl-N,N-dimethyl ethanamine 3HCl (0.3 g; 0.00068 mol), 6-chloro-7-methyl-7,9-dihydro-purin-8-one (0.15 g; 0.00081 mol), DIPEA (1.07 mL; 0.0062 mol) in NMP (9 mL) and stir at 150° C. in microwave for 45 min. Cool, and quench the reaction with saturated sodium bicarbonate solution and extract with EA. Evaporate the EA layer and purify on silica gel using DCM and methanol as eluent to give the title compound (0.032 g; 9.3%). MS (ES+): m/z=484 (M+1).

Example 59

6-{4-[4-(3,4-Difluoro-phenyl)-1-(2-dimethylamino-ethyl)-1H-imidazol-2-yl]-piperidin-1-yl}-7-ethyl-7,9-dihydro-purin-8-one Combine 2-(4-(3,4-difluorophenyl)-2-(piperidin-4-yl)-1H-imidazol-1-yl-N,N-dimethyl ethanamine.3HCl (0.25 g; 0.00057 mol); 6-chloro-7-ethyl-7,9-dihydro-purin-8-one (0.15 g; 0.00074 mol); TEA (0.46 mL; 0.0033 mol) in methanol (5 mL) and heat in a microwave at 160° C. for 60 min. Cool, concentrate, quench with water and extract with EA. Evaporate the EA layer, and purify the residue with silica gel chromatography using 0-10% MeOH/DCM as eluent to give the title compound (0.03 g, 10%). MS (ES+): m/z=497 (M+1).

Example 60

4-{4-[4-(3,4-Difluoro-phenyl)-1-(2-dimethylamino-ethyl)-1H-imidazol-2-yl]-piperidin-1-yl}-5-ethyl-5,7-dihydro-pyrrolo[2,3-d]pyrimidin-6-one

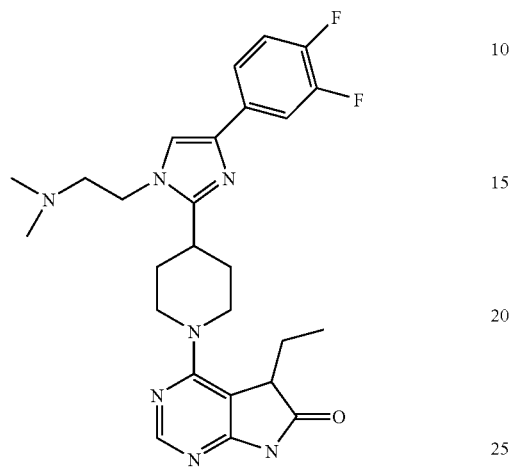

Combine 2-(4-(3,4-difluorophenyl)-2-(piperidin-4-yl)-1H-imidazol-1-yl-N,N-dimethyl ethanamine (0.35 g; 0.0010 mol; 1.0 equiv), 4-chloro-5-ethyl-5,7-dihydro-pyrrolo[2,3-d]pyrimidin-6-one (0.23 g; 0.0011 mol; 1.1 equiv), DIPEA (0.72 mL; 0.0041 mol; 4.0 equiv) in IPA (10 mL) and stir at 90° C. for 16 h. Quench the reaction with demineralized water and extract with EA. Evaporate the organic layer, purify over a silica gel column with 0-10% MeOH/DCM to give the title compound (0.13 g; 24.13%). MS (ES+): m/z=496 (M+H).

Prepare the following examples in manner similar to that described for 4-{4-[4-(3,4-difluoro-phenyl)-1-(2-dimethylamino-ethyl)-1H-imidazol-2-yl]-piperidin-1-yl}-5-ethyl-5,7-dihydro-pyrrolo[2,3-d]pyrimidin-6-one:

| Example | Compound Name | Structure | MS (ES+): m/z (M + 1) | Reaction Conditions |
|---|---|---|---|---|
| 61 | 3-{1-[2-Dimethylamino-ethyl]-2-(1-(6-oxo-6,7-dihydro-5H-pyrrolo[2,3-d]pyrimidin-4-yl)piperidin-4-yl]-1H-imidazol-4-yl}benzonitrile | 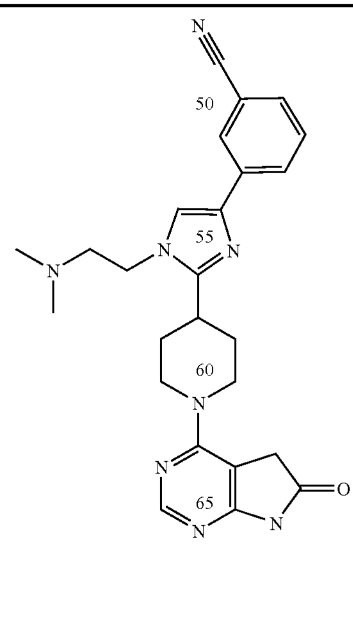 | 457 | Conventional heating 100° C., 2 h |

| Example | Compound Name | Structure | MS (ES+): m/z (M + 1) | Reaction Conditions |
|---|---|---|---|---|
| 62 | 4'-(4-(4-(3,4-Difluorophenyl)-1-(2-dimethylamino-ethyl)-1H-imidazol-2-yl)piperidin-1-yl)spiro[cyclopentane-1,5'-pyrrolo[2,3-d]pyrimidin]-6'(7'H)-one | 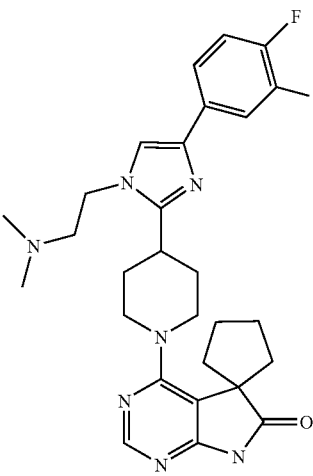 | 522 | Conventional 150° C., 20 h |
| 63 | 4-{4-[4-(3,4-Difluorophenyl)-1-(2-dimethylamino-ethyl)-1H-imidazol-2-yl]-piperidin-1-yl}-5-methyl-5H-pyrrolo[2,3-d]pyrimidin-6(7H)-one | 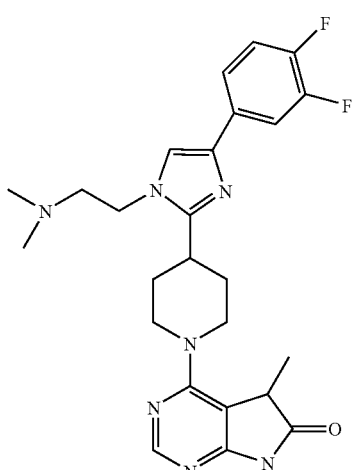 | 482 | Conventional 100° C., 20 h |
| 64 | 4-{4-[4-(3,4-Difluorophenyl)-1-(2-(3-hydroxypyrrolidin-1-yl)ethyl)-1H-imidazol-2-yl]-piperidin-1-yl}-5H-pyrrolo[2,3-d]pyrimidin-6(7H)-one hydrochloride | 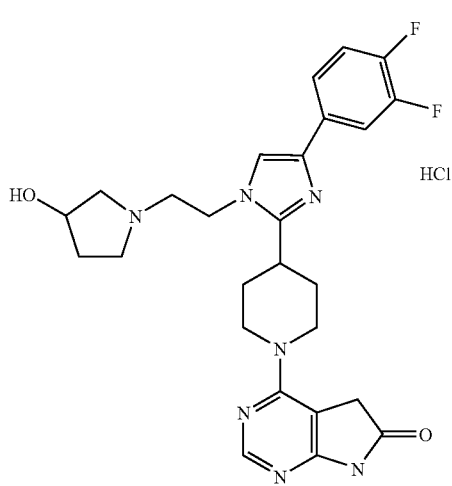 | 510 | Conventional 80° C., 20 h |

| Example | Compound Name | Structure | MS (ES+): m/z (M + 1) | Reaction Conditions |
|---|---|---|---|---|
| 65 | 4-{4-[1-(2-Dimethylamino-ethyl)-4-phenyl-1H-imidazol-2-yl]-piperidin-1-yl}-5H-pyrrolo[2,3-d]pyrimidin-6(7H)-one | 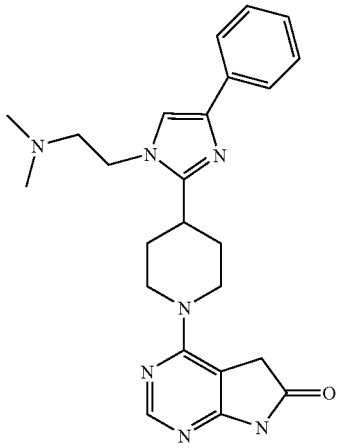 | 432 | Conventional 80° C., 6 h |
| 66 | 4-{4-[4-(3,4-Difluorophenyl)-1-(2-(3-hydroxypyrrolidin-1-yl)ethyl)-1H-imidazol-2-yl]-piperidin-1-yl}-5,5-dimethyl-5H-pyrrolo[2,3-d]pyrimidin-6(7H)-one hydrochloride | 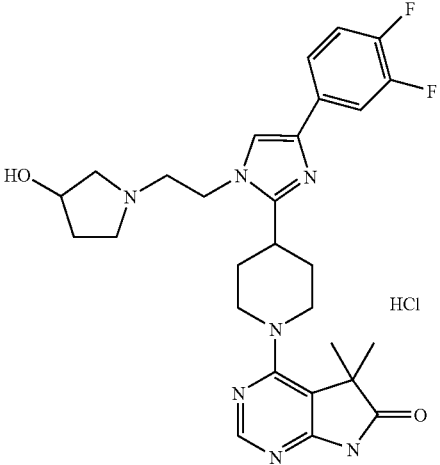 | 538 | Conventional 80° C., 20 h |
| 67 | 4-{4-[4-(3,4-Difluorophenyl)-1-(2-((2-hydroxyethyl)(methyl)amino)ethyl)-1H-imidazol-2-yl]-piperidin-1-yl}-5,5-dimethyl-5H-pyrrolo[2,3-d]pyrimidin-6(7H)-one | 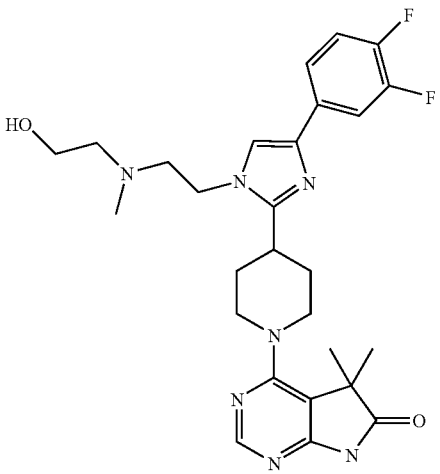 | 526 | Conventional 130° C., 20 h |

| Example | Compound Name | Structure | MS (ES+): m/z (M + 1) | Reaction Conditions |
|---|---|---|---|---|
| 68 | 4-{4-[4-(4-Fluoro-3-trifluoromethyl-phenyl)-1-(2-(pyrrolidin-1-yl)ethyl)-1H-imidazol-2-yl]-piperidin-1-yl}-5,5-dimethyl-5H-pyrrolo[2,3-d]pyrimidin-6(7H)-one | 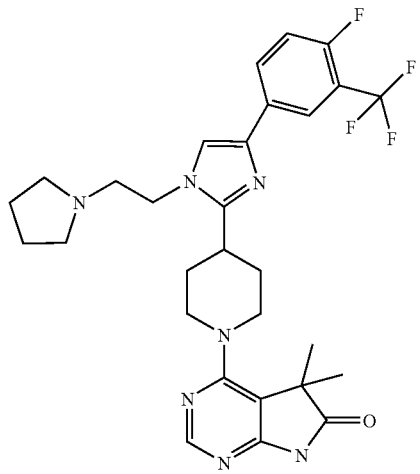 | 572 | Conventional 150° C., 16 h |
| 69 | 4-{4-[4-(3,4-Difluorophenyl)-1-(2-((2-hydroxyethyl)(methyl)amino)ethyl)-1H-imidazol-2-yl]-piperidin-1-yl}-5H-pyrrolo[2,3-d]pyrimidin-6(7H)-one | 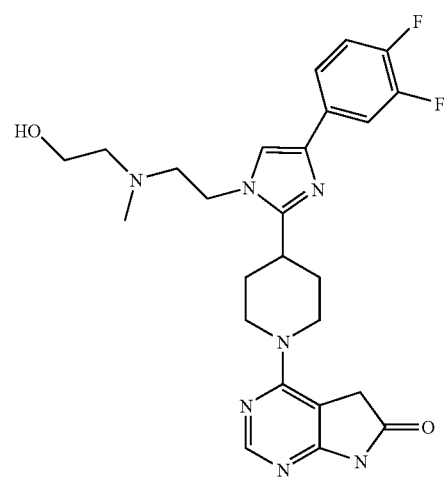 | 498 | Conventional 80° C., 16 h |
| 70 | 4-{4-[4-(3-Chloro-4-fluorophenyl)-1-(2-dimethylamino-ethyl)-1H-imidazol-2-yl]-piperidin-1-yl}-5,5-dimethyl-5H-pyrrolo[2,3-d]pyrimidin-6(7H)-one | 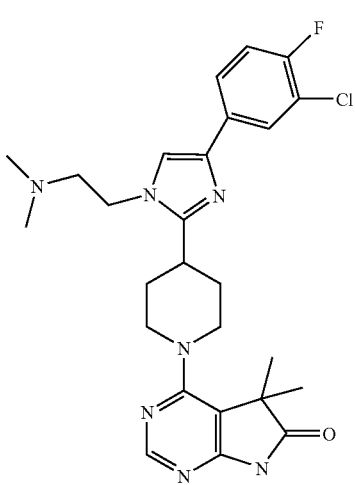 | 512 | Micowave 220° C., 2 h NMP, DBU |

-continued

| Example | Compound Name | Structure | MS (ES+): m/z (M + 1) | Reaction Conditions |
|---|---|---|---|---|
| 71 | 4-{4-[4-(4-Fluoro-3-trifluoromethyl-phenyl)-1-(2-(pyrrolidin-1-yl)ethyl)-1H-imidazol-2-yl]-piperidin-1-yl}-5H-pyrrolo[2,3-d]pyrimidin-6(7H)-one | 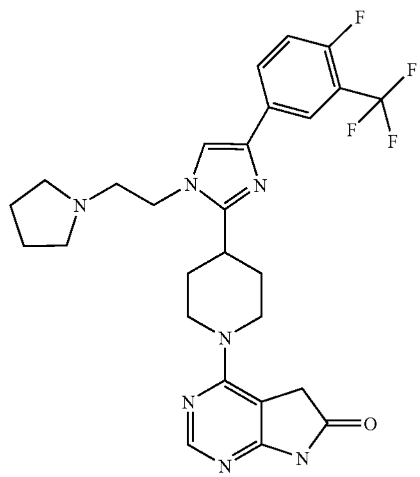 | 544 | Microwave 90 min, 80° C. |
| 72 | 4-{4-[1-(2-Dimethylamino-ethyl)-4-(4-fluoro-3-trifluoromethyl-phenyl)-1H-imidazol-2-yl]-piperidin-1-yl}-5-ethyl-5,7-dihydro-pyrrolo[2,3-d]pyrimidin-6-one | 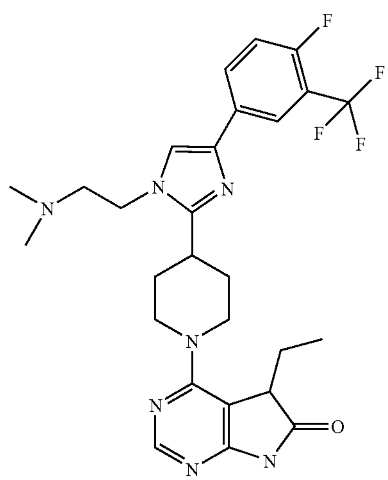 | 546 | Conventional 110° C., 16 h |
| 73 | 4-{4-[1-(2-Dimethylamino-ethyl)-4-(4-fluoro-3-trifluoromethyl-phenyl)-1H-imidazol-2-yl]-piperidin-1-yl}-5-methyl-5,7-dihydro-pyrrolo[2,3-d]pyrimidin-6-one | 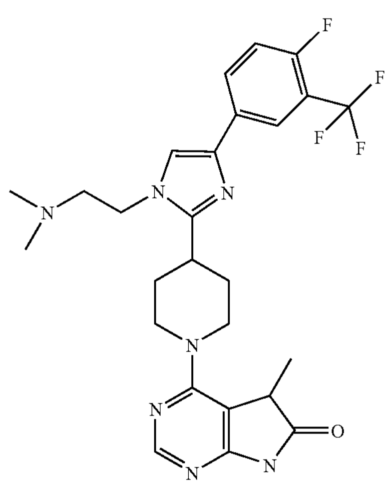 | 532 | Conventional 150° C., 16 h |

-continued

| Example | Compound Name | Structure | MS (ES+): m/z (M + 1) | Reaction Conditions |
|---|---|---|---|---|
| 74 | 4-{4-[4-(3-Chloro-phenyl)-1-(2-dimethylamino-ethyl)-1H-imidazol-2-yl]-piperidin-1-yl}-5,7-dihydro-pyrrolo[2,3-d]pyrimidin-6-one | 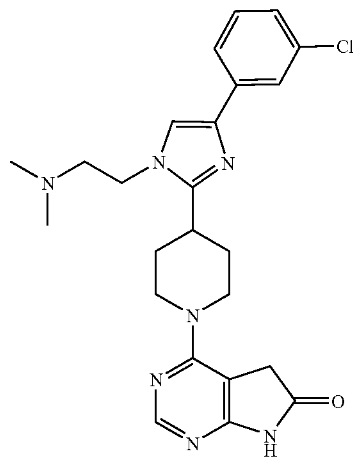 | 466 | Conventional 80° C., 2 h |
| 75 | 4-{4-[1-(2-Dimethylamino-ethyl)-4-(3-trifluoromethyl-phenyl)-1H-imidazol-2-yl]-piperidin-1-yl}-5,7-dihydro-pyrrolo[2,3-d]pyrimidin-6-one | 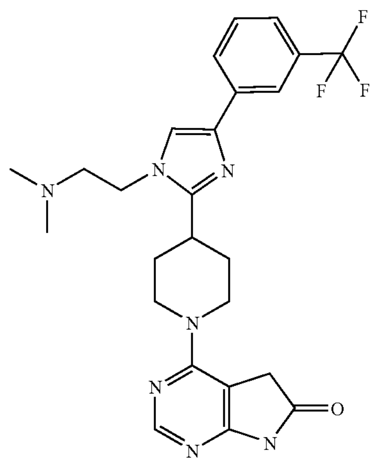 | 500 | Microwave 135° C. (DMF as solvent), 20 min |
| 76 | 4-{4-[4-(4-Chloro-phenyl)-1-(2-dimethylamino-ethyl)-1H-imidazol-2-yl]-piperidin-1-yl}-5,7-dihydro-pyrrolo[2,3-d]pyrimidin-6-one | 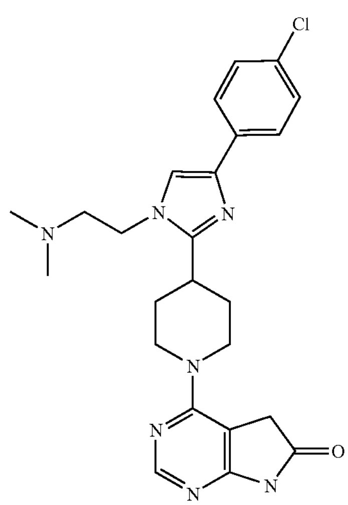 | 466 | Conventional |

| Example | Compound Name | Structure | MS (ES+): m/z (M + 1) | Reaction Conditions |
|---|---|---|---|---|
| 77 | 4-{4-[4-(3-Chloro-4-fluorophenyl)-1-(2-(pyrrolidin-1-yl)ethyl)-1H-imidazol-2-yl]-piperidin-1-yl}-5-methyl-5H-pyrrolo[2,3-d]pyrimidin-6(7H)-one | 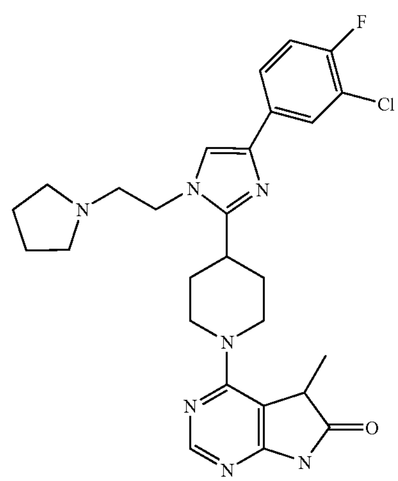 | 525 | Conventional |
| 78 | 4-{4-[4-(3-Chloro-4-fluorophenyl)-1-(2-dimethylamino-ethyl)-1H-imidazol-2-yl]-piperidin-1-yl}-5-methyl-5H-pyrrolo[2,3-d]pyrimidin-6(7H)-one | 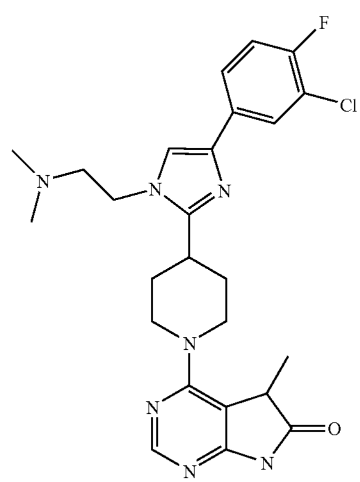 | 499 | Conventional |
| 79 | 4-{4-[4-(4-Fluoro-3-trifluoromethyl-phenyl)-1-(2-(pyrrolidin-1-yl)ethyl)-1H-imidazol-2-yl]-piperidin-1-yl}-5-methyl-5H-pyrrolo[2,3-d]pyrimidin-6(7H)-one | 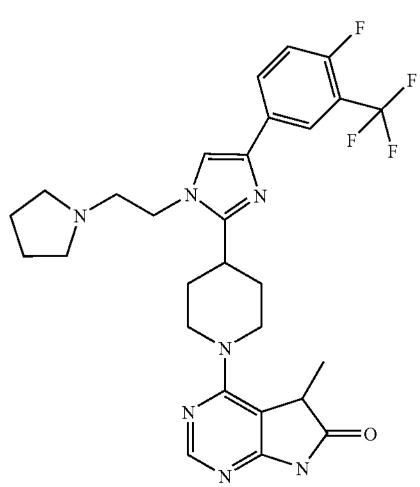 | 558 | Conventional |

-continued

| Example | Compound Name | Structure | MS (ES+): m/z (M + 1) | Reaction Conditions |
|---|---|---|---|---|
| 80 | 4-{4-[4-(3,4-Difluorophenyl)-1-(2-(3-hydroxyazetidin-1-yl)ethyl)-1H-imidazol-2-yl]-piperidin-1-yl}-5H-pyrrolo[2,3-d]pyrimidin-6(7H)-one | 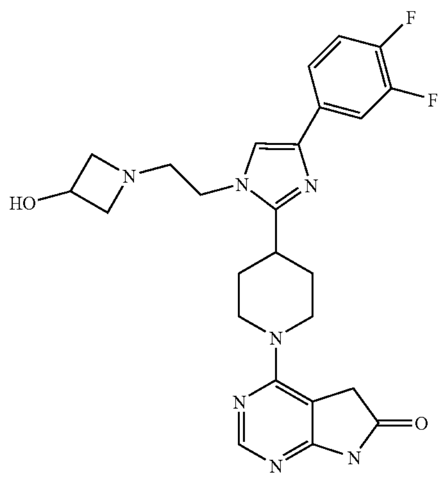 | 496 | Conventional |
| 81 | 4-{4-[4-(3-Chloro-4-fluorophenyl)-1-(2-(pyrrolidin-1-yl)ethyl)-1H-imidazol-2-yl]-piperidin-1-yl}-5-ethyl-5H-pyrrolo[2,3-d]pyrimidin-6(7H)-one | 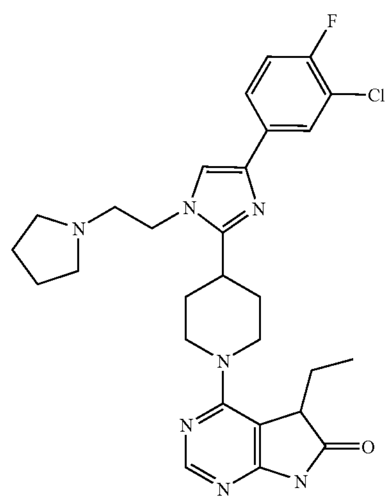 | 539 | Conventional |
| 82 | 4-{4-[1-(2-Dimethylamino-ethyl)-4-(4-fluorophenyl)-1H-imidazol-2-yl]-piperidin-1-yl}-5H-pyrrolo[2,3-d]pyrimidin-6(7H)-one | 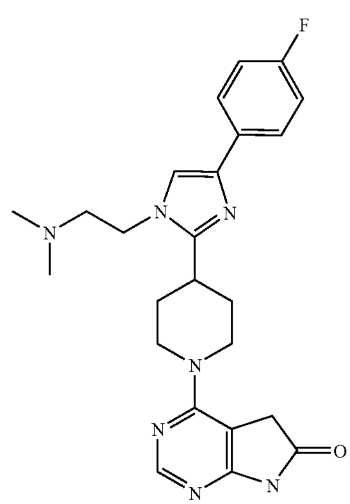 | 450 | Conventional |

| Example | Compound Name | Structure | MS (ES+): m/z (M + 1) | Reaction Conditions |
|---|---|---|---|---|
| 83 | 6-{4-[1-(2-Dimethylamino-ethyl)-4-(4-fluoro-3-trifluoromethyl-phenyl)-1H-imidazol-2-yl]-piperidin-1-yl}-7-methyl-7H-purin-8(9H)-one | 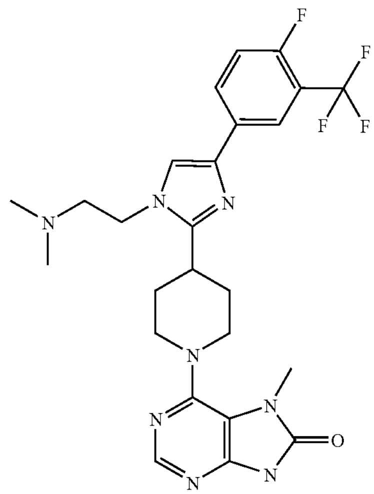 | 533 | Conventional |
| 84 | 6-{4-[4-(3-Chloro-4-fluorophenyl)-1-(2-(pyrrolidin-1-yl)ethyl)-1H-imidazol-2-yl]-piperidin-1-yl}-7-methyl-7H-purin-8(9H-one | 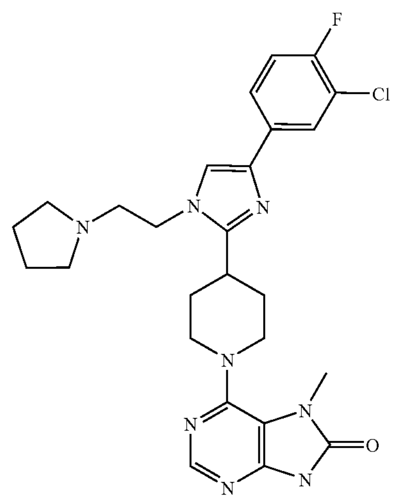 | 526 | Conventional |
| 85 | 6-{4-[4-(4-Fluoro-3-trifluoromethyl-phenyl)-1-(2-(pyrrolidin-1-yl)ethyl)-1H-imidazol-2-yl]-piperidin-1-yl}-7-methyl-7H-purin-8(9H)-one | 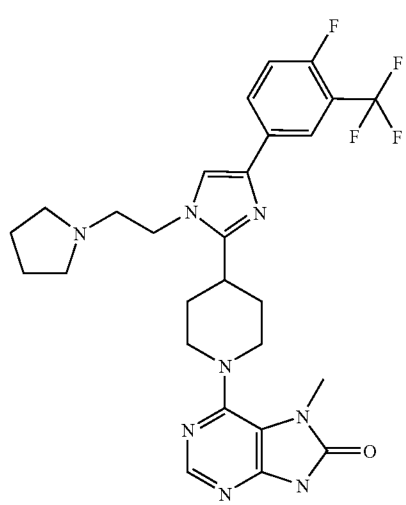 | 559 | Conventional |

Example 86

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one

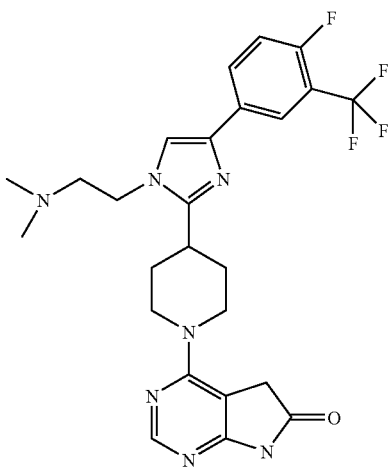

Method A: Charge a pressure tube with a mixture of 4-(4-(1-(2-(dimethylamino)ethyl)-4-(4-fluoro-3-(trifluoromethyl)phenyl)-1H-imidazol-2-yl)piperidin-1-yl)-7-(4-methoxybenzyl)-5H-pyrrolo[2,3-d]pyrimidin-6(7H)-one (1.00 equiv; 24.46 mmol; 15.60 g) in 48% aq HBr (1.39 mol; 156.00 mL) and acetic acid (816.72 mmol; 46.80 mL). Stir the reaction at 115° C. for 36 h. Filter on a frit, and wash the solid with water (100 mL). Precipitate the filtrates with a solution of Na$_2$HPO$_4$ (10% w/w (312 mL)) and filter on a frit to obtain a tan solid. Dry the solid under vacuum and suspend in ACN and filter filtered on a frit. Re-suspend the solid in ACN (70 mL) and filter on a frit to obtain the title compound (11.05 mmol; 5.72 g; 45.18%) as a cream colored solid. $^1$H NMR (300 MHz, DMSO): 10.96 (bs, 1H), 8.20 (s, 1H), 8.02-7.98 (m, 2H), 7.75 (s, 1H), 7.48-7.41 (m, 1H), 4.55-4.47 (m, 2H), 4.05 (t, J=6.4 Hz, 2H), 3.75 (s, 2H), 3.34-3.35 (m, 2H), 3.21-3.07 (m, 3H), 2.59 (t, J=6.4 Hz, 2H), 2.21 (s, 6H), 1.83-1.73 (m, 2H).

Method B: In a pressure flask, charge a mixture of 4-(4-(1-(2-(dimethylamino)ethyl)-4-(4-fluoro-3-(trifluoromethyl)phenyl)-1H-imidazol-2-yl)piperidin-1-yl)-7-(2,4-dimethoxybenzyl)-5H-pyrrolo[2,3-d]pyrimidin-6(7H)-one (1.00 equiv; 148.3 mmol; 99.0 g) in TFA (1.98 mol; 150 mL) and anisole (2.75 mol; 300 mL). Stir at 120-125° C. for 20 h, then at 140° C. for 3 h. Cool to RT and add DCM (2.5 L) and H$_2$O (2.0 L). Rinse the reaction flask with 0.5 N HCl (0.5 L). Extract the organic layer with 0.3 N HCl (500 mL). Extract the combined aqueous layers with DCM (500 mL), and extract the combined organic layers with 0.1N HCl (500 mL). The separation flask contains a tarry residue, and this is rinsed from the flask with DMF. Stir the combined aqueous acid layers, containing the product, with DCM (4 L), and adjust the pH to 5 with the addition of NaOH (50% aq. solution, 130 mL). Adjust the pH further to 11.5-12 with NaOH (5 N aq. solution, 25 mL). Separate the layers and extract the aqueous layer twice with DCM (2.5 L and 1.5 L). Combined the DCM layers and wash with 15% NaCl aq. solution (2 L). Extract the aqueous layer with DCM (1 L). Combine the organic layers and evaporate in vacuo to a gray/pink colored solid. Stir the solid with can (800 mL) and heat to 60° C. to form a slurry. Add water (800 mL) and reheat to 60° C. Allow to stir and come to RT. Filter, wash with 1:1 ACN:water, and then with ACN. Filter on a frit to obtain the title compound (116 mmol; 60.05 g; 78.3%) as a light pink colored solid. $^1$H NMR (300 MHz, DMSO): 10.96 (bs, 1H), 8.20 (s, 1H), 8.02-7.98 (m, 2H), 7.75 (s, 1H), 7.48-7.41 (m, 1H), 4.55-4.47 (m, 2H), 4.05 (t, J=6.4 Hz, 2H), 3.75 (s, 2H), 3.34-3.35 (m, 2H), 3.21-3.07 (m, 3H), 2.59 (t, J=6.4 Hz, 2H), 2.21 (s, 6H), 1.83-1.73 (m, 2H).

Example 87

Preparation of Crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate To a 20 mL scintillation vial fitted with stir bar charge with 211 mg of 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, followed by 2 mL of a 3:1 IPA/H$_2$O solvent mixture. Seed the suspension with 12 mg of hemihydrate seed crystals (see preparation below). Stir (~600 RPM) at RT for approximately 4 days. Isolate the product by vacuum filtration.

Preparation of Hemihydrate Seed Crystals:

To a 20 mL scintillation vial fitted with stir bar charge with 134 mg of 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, followed by 13 mL of THF. Stir (~600 RPM) the resulting slurry over 50° C. heat for ~15 minutes until dissolution occurs. Filter the warm solution using an 0.25 µm filter. To the warm solution, add 5 mL heptane dropwise until turbidity persists. Add an additional 2 mL heptane to increase yield and cool the solution naturally to RT. Isolate the product by vacuum filtration.

X-ray Powder Diffraction:

X-ray powder diffraction analysis is performed on a Bruker D4 Endeavor X-ray powder diffractometer, equipped with a CuKa source (λ=1.54056 Å) and a Vantec detector, and operating at 40 kV and 50 mA, with 0.6 mm divergence and detector slits. The analysis is performed at RT. The sample is scanned from 4° to 40° in 2θ, with a step size of 0.009 in 2θ and a scan rate of 0.2 seconds per step.

Crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate is characterised by an X-ray powder diffraction pattern comprising peaks at 7.4, 14.9, 21.1, 19.8 and 10.5 (±0.1° 2θ).

$^{13}$C Solid-State NMR:

$^{13}$C Cross polarization/magic angle spinning (CP/MAS) NMR (solid-state NMR or SSNMR) spectra are obtained using a Bruker Avance II 400 MHz NMR spectrometer operating at a carbon frequency of 100.622 MHz and equipped with a Bruker 4 mm double resonance probe. TOSS sideband suppression is used along with cross polarization employing SPINAL64 decoupling (95.4 Watts) and a RAMP100 shaped H-nucleus CP pulse. Acquisition parameters are as follows: 90° proton r.f. pulse width of 2.5 µs, contact time is 0.5 ms, pulse repetition time of 5 s, MAS frequency of 10 kHz, spectral width of 30 kHz, acquisition time is 34 ms. Chemical shifts are referenced to adamantane (δ=29.5 ppm) in a separate experiment.

Crystalline 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemihydrate is characterised by an SSNMR spectrum comprising resonances at 179.8, 156.9, 151.9, 137.5 and 33.8 ppm.

Example 88

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one

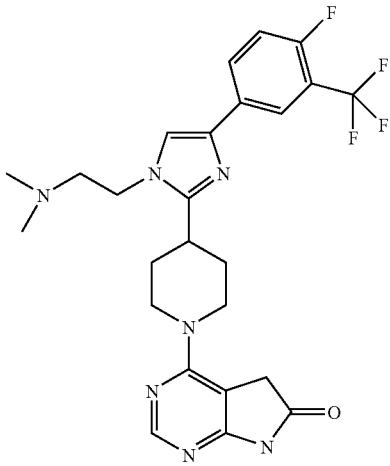

Triethyl ethane-1,1,2-tricarboxylate

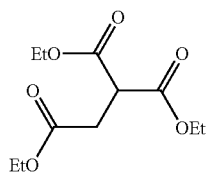

Charge 400 L of acetone into a reactor. Charge 71.17 Kg of powdered potassium carbonate maintaining the temperature at 25-30° C. Charge 55 Kg of Diethylmalonate into the reactor under stirring maintaining the temperature at 25-30° C. Heat the reaction 55-60° C. for 2.5 hours. Cool the reaction to 50-54° C. and slowly add 5.225 Kg of sodium iodide into the reactor maintaining the temperature at 52-54° C.

15. Slowly add 71.5 Kg of ethyl bromo acetate maintaining the temperature at 52-54° C. Stirring for 12-14 hours maintaining the temperature between 55-60° C. (reflux). Cool the reaction to 10-15° C., filter the reaction mass and wash the resulting filter cake with 110 L of acetone (at 10-15° C.). Charge the filtrate into the reactor, heat to 45-50° C. and concentrate until no distillate is seen. Apply vacuum to the concentrated distillate and distill the excess unreacted diethyl malonate under vacuum (0.4-0.5 mmHg) with an external temperature of 80° C. Increase the temperature to 135° C. and distill the product to afford 45.5 kg of triethyl ethane-1,1,2-tricarboxylate (53.72%) in 93.2% purity by GC.

Ethyl 2-(4,6-dihydroxypyrimidin-5-yl)acetate

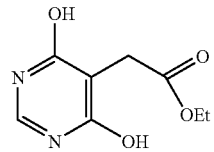

Charge 394.5 L methanol into the reactor at room temperature. Charge 0.3682 Kg of sodium methoxide into the reactor at RT followed by triethyl ethane-1,1,2-tricarboxylate (93.31 Kg). Stir at RT for 3 hours. Heat the reaction to 40-50° C. and distill out methanol completely under vacuum. Charge 263 L of methanol into the reactor at 40-50° C. and distill out methanol completely under vacuum at 40-50° C. Charge 263 L of methanol into the reactor at 40-50° C. cool slowly to 10-15° C. to promote crystallization. Charge 54.54 Kg of sodium methoxide maintaining the temperature at 10-15° C. Heat the reaction slowly to RT and stir for 1 hour. Charge 26.3 Kg of Formamidine acetate into the reactor at RT and slowly raise the temperature of the reaction mass to reflux (65-68° C.). Stir for 2-9 hours by maintaining the temperature at 65-68° C. Slowly decrease the reaction temperature to 10-15° C. and adjust the pH of reaction to 1.5-2.0 by slowly adding the Methanolic HCl (15-18%) maintaining the temperature at 10-15° C. Cool the reaction to 0-5° C. and maintain for 1 hour. Filter the resulting solids via centrifuge at 0-5° C. and spin dry the wet cake for 30 minutes. Wash the wet cake with 26.3 L of chilled methanol (0-5° C.) and spin-dry the wet cake for 30 min. Dry the material under vacuum at 40-45° C. to afford ethyl 2-(4,6-dihydroxypyrimidin-5-yl)acetate (35.65 Kg, 76.6%) as a solid.

Ethyl 2-(4,6-dichloropyrimidin-5-yl)acetate

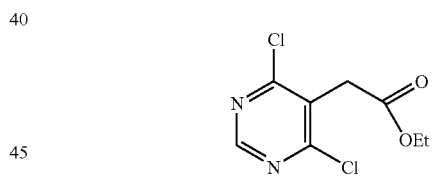

Charge 525 L of toluene and ethyl 2-(4,6-dihydroxypyrimidin-5-yl)acetate (35 kg) into the reactor at RT. Cool the reaction to 10-15° C. and charge 87.5 Kg of phosphorus oxychloride while maintaining the temperature at 10-15° C. Cool the contents of the reactor to 0-5° C. and charge 38.5 Kg of TEA into the reactor while maintaining the temperature between 0-5° C. Heat to reflux (110-115° C.) and stir for 3 hours. Distill out 175 L of toluene from the reaction at 110-115° C. under atmospheric pressure. Charge 175 L of toluene at the temperature 45-50° C. then distill out the same volume of toluene as charged at 110-115° C. under atmospheric pressure. Cool the reaction mass to 20-22° C. and charge 175 L of water while maintaining the temperature at 20-22° C. Stir for 15 minutes at 20-22° C. Filter the resulting dark brown emulsion (organic layer) from the reactor through hyflo and collect the filtrate. Wash the hyflo bed with 157.5 L of toluene. Separate the bottom aqueous layer from top organic layer. Wash the aqueous layer with 105 L of toluene and combine the organic layers. Wash the combined organic layers with 175 L of 3% sodium hydroxide solution (2×). Wash the organic layer with 175 L of water (2×) then with 15% brine solution (175 L). Charge 175 L of 15% Brine solution. Distill the organic layer completely under vacuum by maintaining the temperature between 45-50° C. Charge 35 L of Hexane into the reaction mass while maintaining the temperature at 45-50° C. and distill the reaction (2×). Cool the reaction to 0-5° C. and filter the resulting solids. Dry the material under vacuum to afford ethyl 2-(4,6-dichloropyrimidin-5-yl)acetate (25 kg, 59.5%) as a yellow solid.

4-Chloro-7-(2,4-dimethoxybenzyl)-5H-pyrrolo[2,3-d]pyrimidin-6(7H)-one

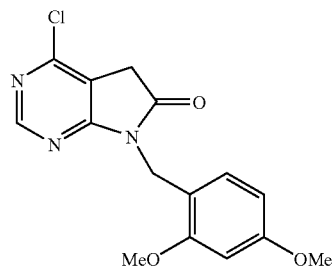

Charge 175 L of DMF and ethyl 2-(4,6-dichloropyrimidin-5-yl)acetate (25 kg) into a reactor at RT. Charge 17.55 Kg of DIPEA into the reactor over a period of 5-10 minutes while maintaining the temperature at 25-28° C. Cool the contents of the reactor to 10-15° C. and stir the reaction for 5-10 minutes. Charge 20.8 Kg of 2,4-Dimethoxybenzylamine into the reactor by while maintaining the temperature at 10-15° C. Heat the reaction slowly to a temperature of 60-65° C. and stir 3 hours. Cool the reaction slowly to 25-28° C. and add 250 L of water into the reactor while maintaining the temperature at 10-15° C. Stir the reaction mass for 10-15 minutes then heat the reaction to 25-28° C. Charge 125 L of DCM into the reaction, stir for 15 minutes and separate the layers. Wash the aqueous layer with 75 L of DCM. Wash the combined organic layers with 75 L of 1N HCl solution followed by water (100 L) and finally with 15% brine (100 L). Distill the organic layer under vacuum at 45-50° C. Charge 50 L of Hexane into the reaction at 45-50° C. and distill the reaction under vacuum at 45-50° C. (2×). Cool the reaction to 0-5° C. and stir for 30 minutes. Filter the resulting solid and wash the wet cake with 50 L of chilled n-Hexane (0-5° C.). Dry the resulting solids under vacuum at 40-45° C. Charge toluene (375 L) the dried solids and 1.025 Kg of para-Toluene to a reactor. Heat the reaction to 85-90° C. for 2 h. Cool the reaction to 80-85° C. and adjust the pH to 6.5-7.0 by adding 10% Sodium bicarbonate solution. Distill the reaction under vacuum at 45-50° C. Cool the contents of the reactor to 25-28° C., charge 3×L of Toluene into the reaction and heat to 85-90° C. Stir for 1 hour then cool the contents of the reactor to 25-28° C. Further cool to 0-5° C. and filter the solids. Wash the wet cake with 75 L of chilled Toluene (0-5° C.). Slurry the solids with 75 L of chilled water (0-5° C.) and filter. Wash the wet cake with 37.5 L of chilled water (0-5° C.) and dry the material under vacuum at 40-45° C. to afford 4-chloro-7-(2,4-dimethoxybenzyl)-5H-pyrrolo[2,3-d]pyrimidin-6(7H)-one (26.5 Kg, 73% yield, 98.89% purity by HPLC).

2-Amino-1-(4-fluoro-3-(trifluoromethyl)phenyl)ethanone, 4-methylbenzenesulfonate Cool a solution of 2-bromo-1-(4-fluoro-3-(trifluoromethyl)phenyl)ethanone (93% pure by HPLC, 1000 g; 3.51 mol) and THF (5 L) to <5° C. in an ice bath. Add a solution of sodium azide (239 g; 3.68 mol, 1.05 eq) in water (800 mL) drop wise over one hour at <5° C. After stirring at <5° C. for one hour, separate and discard the aqueous layer. While still cold, add the organic layer slowly over 3 hours to a solution of triphenylphosphine (920.2 g, 3.51 mol, 1.0 eq), p-toluenesulfonic acid monohydrate (1335 g, 7.02 mol, 2.0 eq), and THF (5 L). Maintain the temperature at <15° C. throughout this addition and solids precipitate during the addition. Stir the reaction mixture at <20° C. for 2 hours and then filter the solid, wash with THF (3×2 L), and dry at 50° C. under vacuum to give 1167.4 g (85%, 92% corrected for starting material purity) of 2-amino-1-(4-fluoro-3-(trifluoromethyl)phenyl)ethanone, 4-methylbenzenesulfonate as a white crystalline solid. HRMS (ESI) m/z (M+H) 222.0531 calculated for $C_9H_8F_4NO$ 222.0537

4-(2-(4-Fluoro-3-(trifluoromethyl)phenyl)-2-oxoethylcarbamoyl)piperidine-1-carboxylic acid tert-butyl ester Combine 2-amino-1-(4-fluoro-3-(trifluoromethyl)phenyl)ethanone, 4-methylbenzenesulfonate (1133 g; 2.88 mol), piperidine-1,4-dicarboxylic acid mono-tert-butyl ester (795 g; 3.47 mol, 1.20 eq), THF (3450 mL), and EA (7500 mL) to form a thin white slurry. Cool the slurry to <5° C. in ice bath and add 2-propanephosphonic acid anhydride ($T_3P$) (50% solution in EtOAc) (2385 g; 3.75 mol, 1.3 eq). Then add NMM (795 mL; 7.21 mol, 2.5 eq) over 1 hour, maintaining the temperature <10° C. Warm the resulting slurry to ambient temperature and stir for 2 hours. Quench the reaction by addition of water. Separate the organic phase, then wash with aqueous $NaHCO_3$, aqueous NaCl. Warm the organic phase to 50° C. on a rotary evaporator and add n-heptane. Distill solvent under vacuum until the final slurry volume is approximately 5 L. Cool the slurry to RT and filter the solids, wash with n-heptane (2×1 L) and then dry in a vacuum oven at 50° C. overnight, resulting in 4-(2-(4-fluoro-3-(trifluoromethyl)phenyl)-2-oxoethylcarbamoyl)piperidine-1-carboxylic acid tert-butyl ester (1124.8 g, 90%) as a white solid. $^1$H NMR (300 MHz, DMSO): 8.37-8.26 (m, 3H), 7.74-7.68 (m, 1H), 4.61 (d, J=5.5 Hz, 2H), 3.91 (d, J=12.9 Hz, 2H), 2.75-2.64 (m, 2H), 2.46-2.37 (m, 1H), 1.69-1.60 (m, 2H), 1.39 (s, 12H).

4-[4-(4-Fluoro-3-trifluoromethyl-phenyl)-1H-imidazol-2-yl]-piperidine-1-carboxylic acid tert-butyl ester Combine 4-(2-(4-fluoro-3-(trifluoromethyl)phenyl)-2-oxoethylcarbamoyl)piperidine-1-carboxylic acid tert-butyl ester (100 g, 231 mmol), ammonium acetate (178.3 g; 2.31 mol, 10 eq), and methanol (1000 mL). The reactor used for this transformation is a coiled 1/16" I.D. stainless steel tube (total internal volume of tubing in oven is 541 mol). Heat the reactor in an oven to 140° C. Control the back pressure in this tube at 250 psig by a regulator to allow super-heating of the solution above its normal boiling point. Pump the solution prepared above continuously through the heated tube under pressure at 6.01 mL/min (affording a total residence time in the heated tube of 90 minutes). As the solution exits the oven, cool it back to 20° C. in a tube-in-tube heat exchanger. Once the entire solution process through the reactor (8 hours total processing time), concentrate the resulting orange solution under vacuum at 30° C. to a total volume of 600 mL. Add ACN (200 mL) and heat the solution to 50° C. Add water (700 mL) drop wise with seeding over 2 hours to crystallize the product. Cool the resulting slurry to 20° C. and filter the solid, then wash with 20% MeOH in water (2×200 mL). Dry the resulting solid under vacuum at 50° C. Re-slurry the solid in ACN (200 mL) at 50° C. Cool the slurry to ambient temperature, filter the solid and wash with ACN (100 mL) to afford 4-[4-(4-fluoro-3-trifluoromethyl-phenyl)-1H-imidazol-2-yl]-piperidine-1-carboxylic acid tert-butyl ester (54.43 g, 132 mmol, 57%) as an off white solid. $^1$H NMR (300 MHz, DMSO): 12.01 (s, 1H), 8.08-8.04 (m, 2H), 7.70 (d, J=1.4 Hz, 1H), 7.49-7.43 (m, 1H), 3.99 (d, J=12.6 Hz, 2H), 2.92-2.85 (m, 3H), 1.91-1.87 (m, 2H), 1.64-1.51 (m, 2H), 1.41 (s, 9H).

4-(1-(2-(Dimethylamino)ethyl)-4-(4-fluoro-3-(trifluoromethyl)phenyl)-1H-imidazol-2-yl)piperidine-1-carboxylic acid tert-butyl ester In a 22 L 3 neck round bottom flask equipped with a mechanical stirrer, nitrogen inlet, drying tube and thermocouple charge DMSO (1385 mL) and 4-[4-(4-fluoro-3-trifluoromethyl-phenyl)-1H-imidazol-2-yl]-piperidine-1-carboxylic acid tert-butyl ester (206.71 g, 0.5 mol, 1 eq). Heat the resulting suspension to 43-48° C. then add sodium hydroxide powder (50 g, 1.25 mol, 2.5 eq) in one portion. Stir the resulting suspension for 1 hour at 43-48° C. To this suspension add 2-chloro-N,N-dimethylethanamine hydrochloride (90 g, 0.625 mol, 1.25 eq). Stir the resulting suspension for 35-40 minutes. Cool the reaction mixture to 18-23° C. and add cold water (227.4 mL). Once water addition is complete, bring the reaction mixture temperature to 20-25° C., stir for 60-90 minutes and filter the suspension. Wash the solids with a mixture of DMSO (103.4 mL) and water (51.7 mL) two times. Wash the solids with water (2×517 mL) and dry solids on a filter with suction to afford the target compound (219.9 g, 87.5% yield) as a tan solid. $^1$H NMR (300 MHz, DMSO): 8.04-8.00 (m, 2H), 7.74 (s, 1H), 7.46 (t, J=9.9 Hz, 1H), 4.06-3.99 (m, 4H), 3.03-2.93 (m, 3H), 2.57 (t, J=6.3 Hz, 2H), 2.19 (s, 6H), 1.81-1.77 (m, 2H), 1.70-1.55 (m, 2H), 1.42 (s, 9H).

2-(4-(4-Fluoro-3-(trifluoromethyl)phenyl)-2-(piperidin-4-yl)-1H-imidazol-1-yl)-N,N-dimethylethanamine trihydrochloride In a 1 L 3 neck round bottom flask with a mechanical stirrer, thermocouple and nitrogen inlet charge ethanol (339.2 mL) and cool to −5 to 5° C. Add drop-wise neat acetyl chloride (78.5 g, 1 mol, 5 eq) at a rate to maintain temperature at 0-15° C. Cool the resulting solution to 0-5° C. and stir for 30 minutes. Add 4-(1-(2-(dimethylamino)ethyl)-4-(4-fluoro-3-(trifluoromethyl)phenyl)-1H-imidazol-2-yl)piperidine-1-carboxylic acid tert-butyl ester (96.9 g, 0.2 mol, 1 eq) over 5-10 minutes. Warm the reaction solution to RT (crystallization takes place) and stir the resulting suspension for 20-28 hours at RT. Once the reaction is deemed complete, filter the reaction mixture and wash the solids with ethanol (3×58 mL) then with heptane (2×96.9 mL). Dry solids under vacuum at 35-40° C. to afford the target compound (105.13 g, >100% yield) as a light tan solid. m/z (M+H): 385.2

4-(4-(1-(2-(Dimethylamino)ethyl)-4-(4-fluoro-3-(trifluoromethyl)phenyl)-1H-imidazol-2-yl)piperidin-1-yl)-7-(2,4-dimethoxybenzyl)-5H-pyrrolo[2,3-d]pyrimidin-6(7H)-one Combine 2-(4-(4-fluoro-3-(trifluoromethyl)phenyl)-2-(piperidin-4-yl)-1H-imidazol-1-yl)-N,N-dimethylethanamine trihydrochloride (98.76 g, 1 eq), DMSO (395 mL) and 4-chloro-7-(2,4-dimethoxybenzyl)-5H-pyrrolo[2,3-d]pyrimidin-6(7H)-one (1.1 eq). Heat the resulting suspension to 60-65° C. then add TEA (6 eq). Stir for 6 hours. Add DMSO (395 mL) and water (150 mL) as a stream and stir the resulting suspension for 1 hour at 45-38° C. Filter the slurry and wash the solids with a mixture of DMSO (1 vol) and water (1 vol) two times. Further wash the solids with water (3×200 mL), methanol (3×200 mL) and heptane (3×200 mL). Dry the cake on the filter to afford the target compound (106.5 g, 79.75% yield) as a tan solid. $^1$H NMR (400 MHz, DMSO): 8.18 (s, 1H), 7.99-7.95 (m, 2H), 7.71 (s, 1H), 7.43-7.39 (m, 2H), 6.76 (d, J=7.1 Hz, 1H), 6.54 (d, J=2 Hz 1H), 6.38-6.35 (m, 1H), 4.67 (s, 2H), 4.49 (d, J=13.1 Hz, 2H), 4.03 (t, J=6.52, 2H), 3.89 (s, 2H), 3.78 (s, 3H), 3.69 (s, 3H), 3.15-3.09 (m, 3H), 2.57 (t, J=6.6 Hz, 2H), 2.18 (s, 6H), 1.89-1.74 (m, 4H).

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid Combine a solution of 4-(4-(1-(2-(dimethylamino)ethyl)-4-(4-fluoro-3-(trifluoromethyl)phenyl)-1H-imidazol-2-yl)piperidin-1-yl)-7-(2,4-dimethoxybenzyl)-5H-pyrrolo[2,3-d]pyrimidin-6(7H)-one (1.00 equiv; 1500 g) in DCM (10.125 L, 6.4 volumes). Filter to remove insolubles and cool the filtrate to 0-5° C. Add anisole (3.0 L) followed by TFA (3.3 L). Cool the solution to 0-5° C. and stir overnight. Add triflic acid (3.3 L) over 10 minutes (resulting in an exotherm to ~25° C.) and stir 10 minutes before heating the mixture ~30° C. and stirring for 6 h. Cool the reaction to −18° C. and add water (11.25 L). Stir the resulting suspension for 35 minutes and filter. Filter the resulting suspensions from two reactions (as described in Example 86) together and wash the combined solids with water (6 L) and DCM (2×6 L). Suspend the solids in a mixture of water (6 L) and DCM (12 L) and stir for 30 minutes. Filter the solids and wash with water (4×3 L) and DCM (4×3 L) to afford the product, 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid, as a tan solid (4062 g, 93.5% yield). $^1$H NMR (400 MHz, d6-DMSO): 11.32 (s, 1H), 9.50 (bs, 1H), 8.33 (s, 1H), 8.22 (s, 1H), 8.14-8.18 (m, 1H), 7.75-8.12 (m, 1H), 7.76 (t, J=9.2 Hz, 1H), 4.55-4.67 (m, 4H), 3.85 (s, 2H), 3.58-3.65 (m, 3H), 3.16 (t, J=12 Hz, 2H), 2.95 (s, 6H), 2.00-2.07 (m, 2H), 1.80-2.04 (m, 2H); $^{19}$F NMR (400 MHz, d6-DMSO): −60.13 (s, 3F, Aryl-CF$_3$), −77.80 (s, 9F, 3×HOSO$_2$CF$_3$), −114.75 (bs, 1F, Aryl-F).

X-Ray Powder Diffraction: X-ray powder diffraction analysis is performed on a Bruker D4 Endeavor X-ray powder diffractometer, equipped with a CuKa source (λ=1.54056 Å) and a Vantec detector, and operating at 35 kV and 50 mA, with 0.6 mm divergence and detector slits. The analysis is performed at RT. The sample is scanned from 4° to 40° in 2θ, with a step size of 0.009 in 2θ and a scan rate of 0.5 seconds per step.

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid is characterised by an X-ray powder diffraction pattern comprising peaks at 22.6, 21.7, 21.5, 21.1, 20.4, 20.2, 18.6, 18.5, 15.5, 15.0 and 13.2 (±0.1° 2θ).

$^{13}$C Solid-State NMR: $^{13}$C Solid-State NMR is performed as described in Example 87. 4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid is characterised by an SSNMR spectrum comprising resonances at 176.9, 155.4, 150.0, 148.0, 94.6, 57.7, 36.4, 32.0 and 27.4 ppm.

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate Slurry 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one tristrifluoromethanesulfonic acid (4060 g, 4.2 mol, 1 eq) with water (32.5 L, 8 vol). Add 50% aqueous sodium hydroxide solution (1014 g, 3.1 eq) and stir 16 h at RT (pH=7). Add 50% aqueous sodium hydroxide solution (33.6 g, 0.1 eq) and stir 1 h (pH=9-10). Filter the resulting slurry and wash with water (4.06 L, 1 vol). Suspend the solids in water (20.3 L, 5 vol) and stir 1 h. Filter the resulting slurry and wash with water (4.06 L, 1 vol). Suspend the solids in water (20.3 L, 5 vol) and stir 1 h. Filter the resulting slurry and wash with water (4.06 L, 1 vol). Suspend the solids in water (20.3 L, 5 vol) and stir 1 h. Dry the solids under vaccum at 30-35° C. to afford 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate as an off white solid (2087.9 g, 98.1%).
$^{13}$C Solid-State NMR: $^{13}$C Solid-State NMR is performed as described in Example 87. 4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate is characterised by an SSNMR spectrum comprising resonances at 164.9, 150.7, 138.3 and 61.6 ppm.

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one Slurry 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one monohydrate (2056 g, 1 eq) in DCM (25.7 L). Add 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one (14.4 g) as seed to the slurry and heat to reflux for 5 h. Cool the reaction to RT, stir for 30 minutes and filter. Wash the resulting filter cake with DCM (2×4.11 L) and dry the solid under vacuum at 37-42° C. to afford 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one (1840 g, 79.18% yield) as an off white solid. $^1$H NMR (300 MHz, DMSO): 10.96 (bs, 1H), 8.20 (s, 1H), 8.02-7.98 (m, 2H), 7.75 (s, 1H), 7.48-7.41 (m, 1H), 4.55-4.47 (m, 2H), 4.05 (t, J=6.4 Hz, 2H), 3.75 (s, 2H), 3.34-3.35 (m, 2H), 3.21-3.07 (m, 3H), 2.59 (t, J=6.4 Hz, 2H), 2.21 (s, 6H), 1.83-1.73 (m, 2H).

Example 89

4-{4-[1-(2-Dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one hemisuccinate Add 2.5 g of 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one a vial. Add 10 mL of 1M succinic acid in methanol (excess acid) and 2 mL of water. Slurry at ambient temperature for at least 1 hour, remove pink-white slurry and recover solids by vacuum filtration. Repeatedly rinse solids with alternating portions (~5 mL each) of fresh acetone, methanol and follow with a final rinsing of >100 mL (multiple aliquots) of water. To produce the monohydrate, slurry the solids in water at ambient temperature for at least 24 hours and dry in ambient vacuum oven overnight. Yield: 92%.

p70 S6 Kinase In Vitro Enzyme Assay

Compound $IC_{50}$ values against p70 S6 Kinase target are determined using the p70 S6 Transcreener™ Kinase ADP-FP Assay. This assay assesses the activity of p70 S6 kinase in the presence of compound inhibitors by measuring the concentration of adenosine diphosphate (ADP) formed in a kinase reaction. The kinase reactions (25 µL reaction volumes) are performed in 96-well half-area black polystyrene plates. Adenosine triphosphate (ATP) is added to start the reactions. Final reaction conditions are 10 millimolar N-2-hydroxyethyl-piperazine-N'-2-ethanesulfonic acid (HEPES) pH 7.5, 0.005% TRITON™ X-100, 0.082 millimolar ethyleneglycol tetraacetic acid (EGTA), 1 millimolar dithiothreitol, 10 millimolar magnesium chloride, 4 micromolar substrate peptide, 25 micromolar ATP, active p70 S6 Kinase (Human recombinant, amino acids 1-421, T412E, N-terminal histidine-tagged), 4% DMSO and serial dilutions of compound (diluted 1:3 from 20,000 to 1 nanomolar). Following ATP addition, the reactions are incubated at RT for 60 minutes and then quenched with the addition of 25 µL of a quench detection reagent containing 52 millimolar HEPES pH 7.5, 20 millimolar ethylenediamine tetraacetic acid (EDTA), 0.4 molar sodium chloride, 0.02% BRIJ-35™, 10 µg/mL anti-ADP antibody, and 4 nanomolar ADP Far Red Tracer. Quenched reactions are incubated for 4-16 hours, and then read in a Tecan Ultra Evolution plate reader in Fluorescence Polarization mode using polarizing filters of $Ex_{612nm}$ and $Em_{633nm}$ wavelength. Millipolarization (mP) raw data is converted to micromolar ADP using a prepared ADP/ATP standard curve (Huss et al, Development of a Transcreener™ Kinase Assay for Protein Kinase A and Demonstration of Concordance of Data with a Filter-Binding Assay Format, Journal of Biomolecular Screening, 12(4); 2007, 578-584). The $IC_{50}$ value for each compound is derived using percent inhibition data which is calculated using the micromolar ADP reaction data relative to on-plate controls (active enzyme versus 100 millimolar inhibited enzyme controls). The percent inhibition and ten-point compound concentration data is then fit to a four-parameter logistic equation using ACTIVITYBASE 4.0 (*Assay Guidance Manual Version* 5.0, 2008, Eli Lilly and Company and NIH Chemical Genomics Center).

The exemplified compounds were tested essentially as described above and were found to have $IC_{50}$ values of less than or equal to 0.3 µM. Example 31 was tested essentially as described above and was found to have an $IC_{50}$ of 0.007 µM.

This demonstrates that compounds of the present invention are p70 S6 kinase inhibitors.

AKT1 In Vitro Enzyme Assay

Compound $IC_{50}$ values against AKT1 target are determined using the AKT1 Transcreener™ Kinase ADP-FP Assay. This assay assesses the activity of AKT1 in the presence of compound inhibitors by measuring the concentration of ADP formed in a kinase reaction. The kinase reactions (25 µL reaction volumes) are performed in 96-well half-area black polystyrene plates. ATP is added to start the reactions.

Final reaction conditions are 56 millimolar HEPES pH 7.4, 0.008% TRITON™ X-100, 5 millimolar magnesium chloride, 30 micromolar Crosstide peptide, 20 micromolar ATP, hAKT1 Human Recombiant, V-AKT Murine Thymoma Viral Oncogene Homolog 1, histidine-tagged, expressed in insect cells, 4% DMSO and serial dilutions of compound (diluted 1:3 from 20,000 to 1 nanomolar). Following ATP addition, the reactions are incubated at RT for 60 minutes and then quenched with the addition of 25 μL of a quench detection reagent containing 52 millimolar HEPES pH 7.5, 20 millimolar EDTA, 0.4 molar sodium chloride, 0.02% BRU-35™, 10 microgram/milliliter anti-ADP antibody, and 4 nanomolar ADP Far Red Tracer. Quenched reactions are incubated for 4-16 hours, and then read in a Tecan Ultra Evolution plate reader in Fluorescence Polarization mode using polarizing filters of $Ex_{612nm}$ and $Em_{633nm}$ wavelength. Millipolarization (mP) raw data is converted to micromolar ADP using a prepared ADP/ATP standard curve (Huss et al, Development of a Transcreener™ Kinase Assay for Protein Kinase A and Demonstration of Concordance of Data with a Filter-Binding Assay Format, Journal of Biomolecular Screening, 12(4); 2007, 578-584). The $IC_{50}$ value for each compound is derived using percent inhibition data which is calculated using the micromolar ADP reaction data relative to on-plate controls (active enzyme versus 100 millimolar inhibited enzyme controls). The percent inhibition and ten-point compound concentration data is then fit to a four-parameter logistic equation using ACTIVITYBASE 4.0 (*Assay Guidance Manual Version* 5.0, 2008, Eli Lilly and Company and NIH Chemical Genomics Center).

The exemplified compounds were tested essentially as described above and were found to have $IC_{50}$ values of less than or equal to 0.3 μM. Example 31 was tested essentially as described above and was found to have an $IC_{50}$ of 0.006 μM. This demonstrates that compounds of the present invention are AKT1 inhibitors.

AlphaScreen SureFire Detection of phosphorylated S6 Ribosomal Protein (S240/244) and phosphorylated GSK3β (S9) in U87MG Cells The effect of compounds on the formation of endogenous phosphorylated S6 ribosomal protein serine 240/244 (pS6) and phosphorylated GSK3β serine 9 (pGSK3β) are measured using the AlphaScreen SureFire® for either pS6 (TGR Biosciences, TGRS6P2S10K) or pGSK3β(TGRGBS10K). This is a homogeneous assay format using immuno-sandwich capture of the phosphorylated analyte followed by detection using antibody-coated Alphascreen beads to generate an amplified signal.

U87MG cells are maintained in U87MG growth medium consisting of DMEM supplemented with 10% Fetal bovine serum (FBS), 1% Nonessential amino acids and 1% sodium pyruvate. For the assay, cells are harvested by standard procedures and then counted using Vi-Cell. Cells (50,000/well) are plated in 100 μL of U87MG growth medium into Costar #3596 96 well plates. Plates are incubated overnight at 37° C., 5% $CO_2$.

On the day of the assay, cells are treated with 20 μL/well compound diluted in media containing 6% DMSO. After 1 hour at 37° C., the medium is removed and 50 μL of SureFire Lysis Buffer (TGR Biosciences SureFire® Kit component) is added per well and incubation continued at RT for 10 minutes with gentle shaking. The lysate (6.0 μL) is transferred to a 384 well ProxiPlate™ (Perkin Elmer #6006280). For the pS6 assay, a mixture containing 1.3 μL activation buffer, 0.15 μL each donor and acceptor beads (Perkin Elmer AlphaScreen IgG detection Kit 6760617R) and 8.3 μL Reaction Buffer for pS6 detection (TGR Biosciences, TGRS6P2S10K) is added to each well. For the pGSK3β assay, a mixture containing 0.96 μL activation buffer, 0.19 μL each donor and acceptor beads, and 8.7 μL Reaction Buffer for pGSK3β assay (TGR Biosciences, TGRGBS10K) is added to each well. The plate is sealed with foil, incubated at RT for 4 hours with gentle shaking and then read on Perkin Elmer EnVision equipped with a TurboModule using standard AlphaScreen® settings ($Ex_{680nm}$ and $Em_{520-620nm}$). The percent inhibition determined from controls on each plate and ten-point compound concentration data are then fit to a four-parameter logistic equation using ACTIVITYBASE 4.0 (*Assay Guidance Manual Version* 5.0, 2008, Eli Lilly and Company and NIH Chemical Genomics Center).

The following compound was tested essentially as described above and was found to have the following activity:

| EXAMPLE | pS6 - $IC_{50}$(μM) | pGSK3β - $IC_{50}$(μM) |
| --- | --- | --- |
| 31 | 0.065 | 0.331 |

This demonstrates the ability of compounds of the present invention to inhibit p70 S6 activity and AKT activity.

Cell Proliferation Assay

The proliferation assay uses the CellTiter-Glo Luminescent Cell Viability Assay System (commercially available from Promega) to determine the cell number of viable cells in culture based on quantitation of the ATP present, which signals the presence of metabolically active cells.

The cells are plated in 96-well plate at 2000 cells/well in volume of 50 μL medium (DMEM, 10% FBS, 25 mM HEPES, 1.0 mM Sodium Pyruvate, and 0.1 mM Non Essential Amino Acids) except column 1 with medium only as blank control. The plates are incubated overnight at 37° C. and 5% $CO_2$. On the next day, compound stocks are prepared at 40 mM in DMSO (500×) and serially diluted in DMSO in a 96-well round bottom polypropylene plate. Compounds are assayed at 10 concentrations in duplicate, 4 compounds per plate.

4 μL of the serial DMSO dilutions are transferred to a 96 deep-well plate and 1 mL complete culture medium is added to create 2× stock for dosing. 50 μL of each 2× dosing stock is gently transferred to the corresponding well of the cell plate resulting in a 0.2% DMSO concentration and a 100 μL final volume. 50 mL medium are added to the Control columns (Column 12) and background columns (Column 1). Cells are incubated with compound for at 37° C., 5% $CO_2$ for 72 hr.

After incubation, 100 μL of the pre-prepared CellTiter-Glo reagent (Promega, Cat: G7571) is added in each well and then the cells are homogenized by mixing on an orbital shaker for 2 min and incubated at RT for 10 minutes to allow luminescent signal stabilization Luminescent raw data is recorded on Wallac Victor V plate reader and the $IC_{50}$ value for each compound is generated using percent inhibition data. A four-parameter logistic curve is fit to each dose response.

The following compound was tested in the following cell lines essentially as described above:

| EXAMPLE | A2780 $IC_{50}$ (μM) | H1155 $IC_{50}$ (μM) | OPM-2 $IC_{50}$ (μM) | U87MG $IC_{50}$ (μM) | BT474 $IC_{50}$ (μM) |
| --- | --- | --- | --- | --- | --- |
| 45 | 5.9 | 4.9 | 2.3 | >10 | 7.9 |

-continued

| EXAMPLE | HCT116 IC$_{50}$ (μM) | PC3 IC$_{50}$ (μM) | H69 IC$_{50}$ (μM) | 69AR IC$_{50}$ (μM) | 786-O IC$_{50}$ (μM) |
|---|---|---|---|---|---|
| 45 | 7.5 | 6.2 | 6.3 | 9.4 | 3.4 |

This indicates that compounds of the present invention are useful in inhibiting the proliferation of these cell lines via a mechanism involving p70 S6 kinase and/or AKT.

Combination Studies:

The combination studies use the fixed ratio method, where the compound of the present invention and the other therapeutic agent are present in fixed ratios of concentrations corresponding to the IC50 equivalents of single agents. The readout for the combination studies is cell proliferation in respective cell lines using Cell Titer Glo reagents. Controls are processed similarly but without the compound of the present invention or the other therapeutic agent. Analysis of the data is done according to the method described in Zhao et. al., Clinical Cancer Research, 10, 7994-8004 (2004) utilizing a web based tool. A combination index is calculated for a range of cell proliferation inhibition activity levels according to the equation below.

Combination Index at activity level $x$=[Concentration of other therapeutic agent in the combination at the activity level $x$/ICx of the other therapeutic agent]+[Concentration of the compound of the present invention in the combination at the activity level $x$/ICx of the compound of the present invention]

For clarity, Combination index values at 50% inhibition are summarized below.

| EXAMPLE | OTHER THERAPEUTIC AGENT | CELL LINE | COMBINATION INDEX AT 50% INHIBITION | 95% CONFIDENCE INTERVAL |
|---|---|---|---|---|
| 45 | Rapamycin | CAKI-1 | 0.33 | 0.096-0.97 |
| 45 | Rapamycin | ACHN | 0.12 | 0.029-0.50 |
| 45 | Rapamycin | 786-0 | 0.41 | 0.23-0.79 |
| 45 | Erlotinib | H1155 | 0.43 | 0.32-0.55 |
| 45 | Gemcitabine | H1155 | 0.87 | 0.72-1.03 |
| 45 | Cisplatin | H1155 | 0.58 | 0.48-0.69 |
| 45 | Erlotinib | Calu6 | 0.10 | 0.074-.014 |
| 45 | Cisplatin | Calu6 | 0.57 | 0.44-0.73 |
| 45 | Gemcitabine | Calu6 | 1.13 | 0.58-2.14 |
| 45 | Tasisulam | Calu6 | 1.19 | 0.83-1.69 |
| 45 | Pemetrexed | Calu6 | 1.96 | 0.99-6.67 |
| 45 | Pemetrexed | Calu6 | 0.91 | 0.67-1.21 |
| 45 | Docetaxel | Calu6 | 0.94 | 0.67-1.32 |
| 45 | Pemetrexed | NCIH460 | 0.97 | 0.65-1.45 |
| 45 | Cisplatin | NCIH460 | 0.56 | 0.48-0.67 |
| 45 | Docetaxel | NCIH460 | 0.67 | 0.61-0.73 |
| 45 | Gemcitabine | NCIH460 | 0.86 | 0.76-0.97 |
| 45 | Erlotinib | NCIH460 | 0.38 | 0.34-0.43 |
| 45 | Cisplatin | A2780 | 1.04 | 0.75-1.46 |
| 45 | Cisplatin | A2780 | 0.64 | 0.50-0.83 |
| 45 | Doxorubicin•HCl | A2780 | 0.65 | 0.51-0.84 |
| 45 | Doxorubicin•HCl | A2780 | 0.96 | 0.61-1.60 |
| 45 | Cetuximab | HCT116 | 2.02 | 0.23-14.72 |
| 45 | Irinotecan | HCT116 | 0.82 | 0.58-1.15 |

Determination of p70 S6K/AKT In Vivo Target Inhibition

U87MG human glioblastoma cells (5×10$^6$) are subcutaneously implanted into the flank of athymic nude mice in 0.2 mL of matrigel. Two weeks post-implantation, mice are dosed orally or parenterally according to a time course, single dose/single time point, or dose response protocol for the determination of TMED$_{50}$ (threshold minimum effective dose). Tumors are flash frozen at harvest and blood is collected for the determination of parent compound plasma exposure and the calculation of TMEC$_{50}$ (threshold minimum effective concentration) in the case of dose response studies. Tumors or tissues are pulverized in liquid N$_2$ and lysed in 400 μL of XY Lysis Buffer (10 μg/mL Leupeptin, 10 μg/mL Trypsin-Chymotrypsin Inhibitor, 10 μg/mL Tosyl phenyl-alanyl chloromethyl ketone, 10 μg/mL Aprotinin, 60 mM Beta-Glycerol Phosphate, 1% Triton X100, 25 mM Tris pH 7.5, 2.5 mM Pyrophosphate, 150 mM NaCl, 2 mM p-tosyl-L-arginine methyl ester, 15 mM para-nitrophenyl phosphate, 5 mM Benzamidine, 1 mM NaVanadate, 10 mM NaF, 50 μg/mL phenylmethane sulfonyl fluoride, 1 mM 1,4-Dithiothreitol (DTT), 15 mM EDTA pH 8.0, 5 mM EGTA pH 8.0, 1 μM Microcystin, 1 μM Okadaic Acid, and 1 Roche Complete protease inhibitor mini-tablet per 10 mL) using Lysing Matrix D tubes (MP Biomedicals, Solon, Ohio, cat#6913-500) and a BIO101 Thermo Savant Fast Prep FP12. Lysates are aliquoted and either assayed immediately or stored at −80° C. for later testing. In Vivo Target Inhibition of p70 S6K and AKT is measured utilizing Meso Scale Discovery (Gaithersburg, Md.) ELISA technology to assess effects on phosphorylation of the serine 240/244 site of the downstream effector S6RP. Phosphorylation of p70 S6K(T389), AKT(S473) and GSK3β (S9) is also assessed using this technology in a multiplex format. In summary, 20 μg of lysate is added to carbon electrode containing 96-well plates pre-spotted with the appropriate capture antibodies. The protein of interest is probed using a ruthenium labeled detection antibody. Upon the passage of current over the electrode in the presence of read buffer containing the co-reactant TPA, electro-chemiluminescence results in the generation of light which is quantified and recorded using the MSD Sector 6000 instrument. For each study, percent inhibitions are calculated relative to the vehicle control group and ANOVA analysis is performed using the JMP software package for the determination of statistical significance.

Example 31 was tested essentially as described above in the in-vivo target inhibition assay and was found to have the following activity:

| IV Dose (mpk) | Post IV Dose (hr) | p(S240) S6 - % inhibition | p(T389) p70 - % inhibition | p(S9)GSK 3β - % inhibition | pAKT S473 - % inhibition |
|---|---|---|---|---|---|
| 12.5 | 1 | 79.2 | 77.3 | 48.4 | 4.0 |
| 12.5 | 2 | 87.6 | 76.1 | 12.6 | −22.3 |
| 12.5 | 4 | 94.9 | 76.1 | 20.5 | −19.2 |
| 12.5 | 6 | 91.7 | 76.1 | 51.7 | −26.3 |
| 12.5 | 8 | 96.4 | 70.7 | 20.1 | −9.4 |
| 12.5 | 24 | 45.0 | 61.6 | 6.0 | 22.6 |

This demonstrates the ability of compounds of the present invention to inhibit p70 S6 kinase and AKT in vivo.

HERG Assay

Evaluation of the affinity of compounds for the human HERG K$^+$ channel in transfected HEK-293 cells is determined in a radioligand binding assay. Cell membrane homogenates (40 μg protein) are incubated for 75 min at 22° C. with 2 nM [$^3$H]astemizole in the absence or presence of the test compound in a buffer containing 50 mM Tris-HCl (pH 7.4), 10 mM KCl, 1.2 mM MgCl$_2$ and 0.1% Bovine serum albumin (BSA). Nonspecific binding is determined in the presence of 10 μM astemizole. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is astemizole, which is tested in each experiment at several concentrations to obtain a competition curve from which its $IC_{50}$ is calculated. (Finalayson et al, [$^3$H]dofetilide binding in SHSYSY and HEK293 cells expressing a HERG-like K$^+$ channels, Eur. J. Pharmacol., 412: 203 (2001)).

Example 37 was tested essentially as described above and was found to have an $IC_{50}$ of 13.9 μM.

Preferred compounds of the present invention have low hERG activity.

We claim:

1. A compound of the formula:

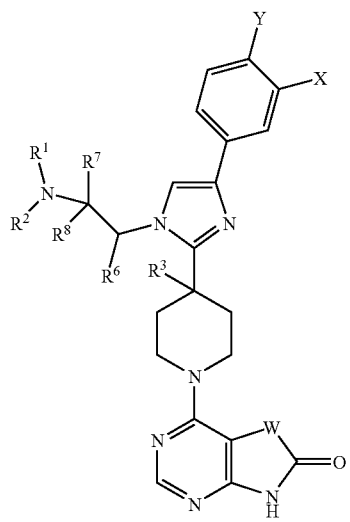

wherein:
X is F, Cl, $CF_3$, CN or H;
Y is F, H or Cl;
$R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position, or an azetidine ring substituted with hydroxy at the 3-position;
$R^3$ is H or OH;
$R^6$ is H; or $R^6$ and $R^2$ together with the nitrogen atom to which $R^2$ is attached form a piperidine ring;
$R^2$ and $R^8$ are independently H or $CH_3$; or $R^7$ and $R^1$ together with the nitrogen atom to which $R^1$ is attached form a pyrrolidine ring;
W is $CR^4R^5$, $NR^{10}$, C=O or C=CH—$R^9$;
$R^4$ and $R^5$ are independently H, $CH_3$, or $CH_2CH_3$; $R^4$ and $R^5$ together with the carbon atom to which they are attached form a cyclopentane ring; or one of $R^4$ or $R^5$ is benzyl and the other is H;
$R^9$ is 2-thiazolyl, 4-pyridyl, 2-methyl-4-thiazolyl, 2-imidazolyl, 5-thiazolyl, or 4-imidazolyl; and
$R^{10}$ is H or $C_1$-$C_3$ alkyl; or a pharmaceutically acceptable salt thereof.

2. The compound according to claim 1, or a pharmaceutically acceptable salt thereof, wherein Y is F.

3. The compound according to claim 2, or a pharmaceutically acceptable salt thereof, wherein X is Cl, $CF_3$, or F.

4. The compound according to claim 3, or a pharmaceutically acceptable salt thereof, wherein W is $CR^4R^5$.

5. The compound according to claim 4, or a pharmaceutically acceptable salt thereof, wherein $R^4$ and $R^5$ are independently H or $CH_3$, or $R^4$ and $R^5$ together with the carbon atom to which they are attached form a cyclopentane ring.

6. The compound according to claim 3, or a pharmaceutically acceptable salt thereof, wherein W is $NR^{10}$.

7. The compound according to claim 3, or a pharmaceutically acceptable salt thereof, wherein W is C=CH—$R^9$.

8. The compound according to claim 7, or a pharmaceutically acceptable salt thereof, wherein $R^9$ is 5-thiazolyl.

9. The compound according to claim 5, or a pharmaceutically acceptable salt thereof, wherein $R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position.

10. The compound according to claim 9, or a pharmaceutically acceptable salt thereof, wherein $R^3$ is H.

11. The compound according to claim 6, or a pharmaceutically acceptable salt thereof, wherein $R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position.

12. The compound according to claim 11, or a pharmaceutically acceptable salt thereof, wherein $R^3$ is H.

13. The compound according to claim 8, or a pharmaceutically acceptable salt thereof, wherein $R^1$ and $R^2$ are independently H, $C_1$-$C_4$ alkyl or $CH_2CH_2OH$; or $R^1$ and $R^2$ together with the nitrogen atom to which they are attached form a pyrrolidine ring optionally substituted with hydroxymethyl at the 2-position or hydroxy at the 3-position.

14. The compound according to claim 13, or a pharmaceutically acceptable salt thereof, wherein $R^3$ is H.

15. 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one, or a pharmaceutically acceptable salt thereof.

16. 4-{4-[1-(2-dimethylamino-ethyl)-4-(4-fluoro-3-trifluoromethyl-phenyl)-1H-imidazol-2-yl]piperidin-1-yl}-5,7-dihydro-pyrrolo[2,3-d]-pyrimidin-6-one.

17. A pharmaceutical formulation comprising a compound according to claim 1, or a pharmaceutically acceptable salt thereof, and a pharmaceutically acceptable carrier, diluent or excipient.

* * * * *

UNITED STATES PATENT AND TRADEMARK OFFICE
CERTIFICATE OF CORRECTION

| | |
|---|---|
| PATENT NO. | : 8,148,387 B2 |
| APPLICATION NO. | : 12/611139 |
| DATED | : April 3, 2012 |
| INVENTOR(S) | : Robert Dean Dally et al. |

Page 1 of 1

It is certified that error appears in the above-identified patent and that said Letters Patent is hereby corrected as shown below:

Column 125, Line 57, in Claim 1, delete "R2" and insert -- R7 --, therefor.

Signed and Sealed this
Twenty-ninth Day of May, 2012

David J. Kappos
*Director of the United States Patent and Trademark Office*